(12) United States Patent
Minshull

(10) Patent No.: US 11,566,262 B2
(45) Date of Patent: Jan. 31, 2023

(54) TETRACYCLINE-INDUCIBLE EXPRESSION SYSTEMS

(71) Applicant: DNA TWOPOINTO INC., Newark, CA (US)

(72) Inventor: Jeremy Minshull, Los Altos, CA (US)

(73) Assignee: DNA TWOPOINTO INC., Newark, CA (US)

( * ) Notice: Subject to any disclaimer, the term of this patent is extended or adjusted under 35 U.S.C. 154(b) by 0 days.

(21) Appl. No.: 17/700,405

(22) Filed: Mar. 21, 2022

(65) Prior Publication Data

US 2022/0307056 A1    Sep. 29, 2022

Related U.S. Application Data

(60) Provisional application No. 63/165,484, filed on Mar. 24, 2021.

(51) Int. Cl.
| | |
|---|---|
| *C12N 15/86* | (2006.01) |
| *A61K 48/00* | (2006.01) |
| *C12N 5/071* | (2010.01) |
| *C12N 15/85* | (2006.01) |
| *A01K 67/027* | (2006.01) |

(52) U.S. Cl.
CPC .......... *C12N 15/86* (2013.01); *A01K 67/0275* (2013.01); *A61K 48/0066* (2013.01); *C12N 5/0682* (2013.01); *C12N 15/8509* (2013.01); *A01K 2217/05* (2013.01); *A01K 2217/203* (2013.01); *A01K 2227/105* (2013.01); *C12N 2710/16142* (2013.01); *C12N 2800/90* (2013.01); *C12N 2830/003* (2013.01); *C12N 2830/50* (2013.01)

(58) Field of Classification Search
CPC .............. C12N 15/86; C12N 2830/003; A01K 2217/05
See application file for complete search history.

(56) References Cited

U.S. PATENT DOCUMENTS

| | | | |
|---|---|---|---|
| 4,736,866 | A | 4/1988 | Leder et al. |
| 4,870,009 | A | 9/1989 | Evans et al. |
| 5,464,758 | A | 11/1995 | Gossen et al. |
| 5,654,168 | A | 8/1997 | Bujard et al. |
| 5,789,156 | A | 8/1998 | Bujard et al. |
| 5,814,618 | A | 9/1998 | Bujard et al. |
| 5,854,310 | A | 12/1998 | Maxson |
| 5,866,755 | A | 2/1999 | Bujard et al. |
| 5,888,981 | A | 3/1999 | Bujard et al. |
| 5,891,665 | A | 4/1999 | Wilson |
| 5,912,411 | A | 6/1999 | Bujard et al. |
| 6,004,941 | A | 12/1999 | Bujard et al. |
| 6,087,166 | A | 7/2000 | Baron et al. |
| 6,136,954 | A | 10/2000 | Bujard et al. |
| 6,242,667 | B1 | 6/2001 | Bujard et al. |
| 6,252,136 | B1 | 6/2001 | Bujard et al. |
| 6,271,341 | B1 | 8/2001 | Baron et al. |
| 6,271,348 | B1 | 8/2001 | Bujard et al. |
| 6,914,124 | B2 | 7/2005 | Bujard et al. |
| 7,541,446 | B2 | 6/2009 | Hillen et al. |
| 7,745,592 | B2 | 6/2010 | Massie et al. |
| 7,935,788 | B2 | 5/2011 | Malenfant et al. |
| 8,728,759 | B2 | 5/2014 | Xu et al. |
| 9,181,556 | B2 | 11/2015 | Bujard et al. |
| 11,060,086 | B2 * | 7/2021 | Minshull ............... C12N 9/1241 |
| 11,060,098 | B2 * | 7/2021 | Minshull ........ C12Y 603/01002 |
| 11,060,109 | B2 * | 7/2021 | Minshull ............... C12N 15/85 |
| 2017/0101629 | A1 | 4/2017 | Minshull et al. |
| 2017/0101647 | A1 * | 4/2017 | Minshull ............... C12N 15/63 |
| 2018/0223314 | A1 * | 8/2018 | Wunderlich ........... A61P 43/00 |
| 2019/0055580 | A1 | 2/2019 | McGrew et al. |

FOREIGN PATENT DOCUMENTS

| | | |
|---|---|---|
| EP | 2352833 B1 | 3/2013 |
| WO | WO 2012/099540 A1 | 7/2012 |

OTHER PUBLICATIONS

Backman et al., "Tetracyciine-inducible expression systems for the generation of transgenic animals; a comparison of various inducible systems carried in a single vector." Journal of Neuroscience Methods, vol. 139, pp. 257-262, (2004).

Barin et al., "Tetracycline-controlled transcription in eukaryotes: novel transactivators with graded transactivation potential," Nucleic Acids Research, 25(14), 2723-2729, (1997).

Cowell, "Repression versus activation in the control of gene transcription," Trends in Biochemical Sciences, 19:1, 38-42, (1994).

Deuschle et al., "Tetracycline-reversible silencing of eukaryotic promoters," Mol. Cell. Biol., 15:4, 1907-1914, (1995).

Fukushige et al., "Genomic targeting with a positive-selection lox, integration vector allows highly reproducible gene expression in mammalian cells." Proc. Natl. Acad. Sci., vol. 89, pp. 7905-7909, (1992).

Gossen et al., "Tight control of gene expression in mammalian cells by tetracycline-responsive promoters." Proc. Natl. Acad. Sci., vol. 89. pp. 5547-5551, (1992).

Gossen et al., "Transcriptional activation by tetracyclines in mammalian cells," Science, 268:5218, 1766-1769, (1995).

Gossen, M., et al., Control of gene activity in higher eukaryotic cells by prokaryotic regulatory elements', TIBS, vol. 18, No. 12, pp. 471-475 (1993).

Hillen et al., "Nucleotide sequence of the Tn 10 encoded tetracycline resistance gene." vol. 11, No. 2, Nucleic Acids Res., pp. 525-539 (1983).

(Continued)

*Primary Examiner* — Brian Whiteman
(74) *Attorney, Agent, or Firm* — Alston & Bird LLP

(57) ABSTRACT

The invention provides inducible promoter systems and their components incorporating components of a tetracycline operon. By coordinating expression of different transcriptional units in these systems as a result of selection of promoters and/or linking the units into the same DNA molecule, these systems can achieve higher levels of expression of coding segments of interest, increased differential levels of expression between on- and off-states, and/or greater responsiveness to inducing agents than conventional systems.

33 Claims, 7 Drawing Sheets

Specification includes a Sequence Listing.

(56) References Cited

OTHER PUBLICATIONS

Hoffman et al., "A novel tetracycline-dependent expression vector with low basal expression and potent regulatory properties in various mammalian cell lines." Nucleic Acids Res., vol. 25, No. 5, pp. 1078 1079, (1997).

Lee et al., "Glucocorticoids regulate expression of dihydrofolate reductase cDNA in mouse mammary tumour virus chimaeric plasmids," Nature (London), 294:228-232, (1981).

Loew et al. Improved Tet-responsive promoters with minimized background expression. BMC Biotechnology 10: 1-13, (2010).

Mullick et al., "The cumate gene-switch: a system for regulated expression in mammalian cells," BMC Biotechnology doi:10.1186/1472-6750-6-43, (2006).

No et al., "Ecdysone-Inducible Gene Expression in Mammalian Cells and Transgenic Mice," Proc. Natl. Acad. Sci. USA, vol. 93, No. 8, pp. 3346-3351, (Apr. 1996).

Rivera et al., "A humanized system for pharmacologic control of gene expression," Nat Med, 2:1028-1032, (1996).

Saenger et al., "The Tetracycline Repressor—A Paradigm for a Biological Switch," Angew. Chem. Int. Ed., 39, 2042-2052, (2000).

Stieger et al., "In vivo gene regulation using tetracycline-regulatable systems." Advanced Drug Delivery Reviews 61, pp. 527-541, (2009).

Tovar et al., "Identification and nucleotide sequence at the class E tet regulatory elements and operator and inducer binding of the encoded purified Tet repressor." Mol. Gen. Genet., vol. 215, pp. 76-80, (1988).

Urlinger et al., "Exploring the sequence space for tetracycline-dependent transcriptional activators: Novel mutations yield expanded range and sensitivity," PNAS, vol. 97, No. 14, pp. 7963-7968, (2000).

Vigna et al., "Robust and Efficient Regulation of Transgene Expression in Vivo by Improved Tetracycline-Dependent Lentiviral Vectors." Molecular Therapy, vol. 5, No. 3, pp. 252-261, (2002).

Weidenfeld et al., "Inducible expression of coding and inhibitory RNAs from retargetable genomic loci." Nucleic Acids Res., pp. 1-11, (2009).

Yao et al., "Tetracycline Repressor, tetR, rather than the tetR Mammalian Cell Transcription Factor Fusion Derivatives, Regulates Inducible Gene Expression in Mammalian Cells," Human Gene Therapy, No. 9. pp. 1939-1950, (1998).

Moritz, et al., "CMV promoter mutants with a reduced propensity to productivity loss in CHO cells," Sci Rep, vol. 5, No. 16952, pp. 1-8, (Nov. 19, 2015).

WIPO Application No. PCT/US/2022/021219, PCT International Search Report and Written Opinion of the International Searching Authority dated Aug. 18, 2022.

* cited by examiner

```
Human CMV    ------------------------------------------------------------TGCT
Hybrid       AGTCATTGGGTTTTTCCAGCCAATTTATAAAACGCCATGTACTTTCCCACCATTGACGTC
Murine CMV   AGTCATTGGGTTTTTCCAGCCAATTTATAAAACGCCATGTACTTTCCCACCATTGACGTC
                                                                        *
                                                    CpG-179
Human CMV    GATGCGGTTTTGGCAGTACACCAATGGG---CGTGGATAGCGGTTT---------GACTC
Hybrid       AATGGGCTATTGAAACTAATGCAACGTGACCTTTAAACGGTACTTTCCCATAGCTGATTA
Murine CMV   AATGGGCTATTGAAACTAATGCAACGTGACCTTTAAACGGTACTTTCCCATAGCTGATTA
              *** * * ***   * **    *** * *      *   *   *   ***       ** *

Human CMV    ACGGGGATTTCCAAGTCTCCACCCCATTGACGTCAATGGGAGTTTGTTTTGGCACCAAAA
Hybrid       ATGGGAAAGTACCGTTCTCGAGCCAATACACGTCAATGGGAGTTTGTTTTGGCACCAAAA
Murine CMV   ATGGGAAAGTACCGTTCTCGAGCCAATACACGTCAATGGGAAGTGAAAGGGCAGCCAAAA
             * *** *  *  *  **** *  ** **  ************  *      *  ******

Human CMV    TCAACGGGACTTTCCAAAATGTCGTAATAACCCCGCCCCGTTGACGCAAATGGGCGGTAG
Hybrid       TCAACGGGACTTTCCAAAATGTCGTAATAACCCCGCCCCGTTGACGCAAATGGGCGGTAG
Murine CMV   CGTAACACCGCCCCGGTTTTCCCCTGGAAATTCCATATTGGC-ACGCATTCTATTGGCTG
                     *         *    * *   **   **      *   *****    ** *
                                        TATA                     +1
Human CMV    GCGTGTACGGTGGGAGGTCTATATAAGCAGAGCTCGTTTAGTGAACCG
Hybrid       GCGTGTACGGTGGGAGGTCTATATAAGCAGAGCTCGTTTAGTGAACCG
Murine CMV   AGCTGCGTTCTACGTGGGTATAAGAGGCGCGACCAGCGTCG-GTACCG
              * **    *  * **     * ***   *  *  * *  * * ****
```

Fig. 1

TETRACYCLINE-INDUCIBLE EXPRESSION SYSTEMS

CROSS-REFERENCE TO RELATED APPLICATION

The present application claims the benefit of 63/165,484 filed Mar. 24, 2021 incorporated by reference in its entirety for all purposes.

REFERENCE TO A SEQUENCE LISTING

The application refers to sequences disclosed in a txt file named 574547SEQTXT.TXT, of 395,981 bytes, created Mar. 21, 2022, incorporated by reference.

BACKGROUND

The tet operon confers tetracycline resistance in bacteria. The operon includes tet-operator sites, a promoter, and a bicistronic transcriptional unit encoding a tet-repressor and a tetracycline-resistance protein. In the absence of tetracycline, the tet-repressor binds to the tet-operator sites inhibiting expression from the promoter of both the tet-repressor and tetracycline-resistance protein. When tetracycline is present it binds to the tet-repressor inhibiting its own binding to the tet-operators. Tetracycline-resistance protein is then expressed as is more tet-repressor, which again shuts downs expression of the tet operon when the tetracycline has been exhausted.

The components of the tet operon have been incorporated into various inducible expression systems for regulating expression of a coding segment of interest (see, e.g., U.S. Pat. Nos. 5,814,618, 5,654,168, 5,650,298 and 5,464,758 and 9,181,556). Generally, such systems have two components. A first construct includes one or more tet-operators, a promoter and a coding segment of interest. A second construct includes a promoter and a tet-repressor (or modified form thereof), sometimes fused to a transcriptional activation domain. The presence of tetracycline controls binding of the tet-repressor to the tet-operators, and consequently expression of the coding segment.

SUMMARY OF THE CLAIMED INVENTION

A hybrid mouse-human CMV promoter effective for transcriptional initiation comprising a segment of a mouse CMV promoter of SEQ ID NO:16 upstream from a segment of a human CMV promoter of SEQ ID NO:13 or 14, wherein the hybrid promoter lacks a CG motif at positions corresponding to positions 42 and 43 of SEQ ID NO:13 (human CMV). Optionally, the hybrid promoter comprises a contiguous segment of the mouse CMV promoter of SEQ ID NO:16 and a contiguous segment of the human CMV promoter of SEQ ID NO:13, wherein the junction between contiguous segments is within the sequence ACGT-CAATGGGA, which is common to the mouse and human CMV promoter sequences. Optionally, the hybrid promoter of claim 2 having a sequence comprising SEQ ID NO:10. Optionally, the hybrid mouse-human-CMV promoter of claim 3 in operable linkage with first and second tet-operators. Optionally the hybrid mouse-human CMV promoter in in operable linkage with at least one cumate operator. Optionally, each cumate operator has a sequence selected independently from any of SEQ ID NOS: 156-158. Optionally, the hybrid mouse-human CMV promoter is in operable linkage with a coding segment to be expressed, optionally wherein the coding segment comprises an open reading frame encoding a polypeptide. Optionally, at least first and second tet-operators are situated between the promoter and coding segment. Optionally, the coding segment encodes a protein. Optionally, the protein is a membrane protein. Optionally, the protein is a therapeutic protein.

The invention further provides a nucleic acid comprising (a) the hybrid mouse-human CMV promoter as described above and (b) a promoter operably linked to a segment encoding a tet-repressor or cumate repressor. Optionally, the promoter of the second transcriptional unit is a weaker promoter than a human CMV promoter, for example, the promoter of the second construct is selected from SEQ ID NOS: 17-21, 33 or 34.

The invention further provides a transposon comprising a nucleic acid as described above flanked by inverted repeats of the transposon. Optionally, the transposon further comprises target sites flanking the inverted repeats. Optionally, the transposon is a piggyBac or piggyBac-like transposon.

The invention further provides a mouse-human-CMV promoter having a sequence comprising SEQ ID NO:12. Optionally, the hybrid mouse-human CMV promoter is in operable linkage with a coding segment to be expressed, optionally wherein the coding segment comprises an open reading frame encoding a polypeptide. Optionally, the coding segment encodes a protein, for example, a therapeutic protein.

The invention further provides a cell transformed with any of the nucleic acids or transposons described above. Optionally, the cell is mammalian.

The invention further provides a non-human animal transformed with any of the nucleic acids or transposons described above. Optionally, the non-human animal is transgenic.

The invention further provides a cell or nonhuman transgenic animal having a genome comprising (a) a hybrid mouse-human CMV promoter operably linked to at least two tet-operators and a coding segment, and (b) a promoter operably linked to a tet-repressor, wherein expression of the coding segment can be regulated by supplying tetracycline or doxycycline to the cell or nonhuman transgenic animal.

The invention further provides a cell or nonhuman transgenic animal having a genome comprising (a) a hybrid mouse-human CMV promoter operably linked to at least one cumate operators and a coding segment, and (b) a promoter operably linked to a cumate repressor, wherein expression of the coding segment can be regulated by supplying cumate or an analog to the cell or nonhuman transgenic animal.

The invention further provides a method for inducible expression of a coding segment comprising, providing a first transcriptional unit comprising in operable linkage a hybrid mouse-human CMV promoter comprising a segment of a mouse CMV promoter of SEQ ID NO: 16 upstream from a segment of a human CMV promoter of SEQ ID NO: 13, wherein the hybrid promoter lacks a CG motif at positions corresponding to positions 42 and 43 of SEQ ID NO:13 (human CMV), at least two tet-operators and a coding segment to be expressed, and a second transcriptional unit comprising in operable linkage a promoter and a segment encoding a tet-repressor, wherein the tet-repressor is expressed and in the absence of tetracycline or doxycycline, the tet-repressor binds to the tet-operators inhibiting expression of the coding segment, and in the presence of tetracycline or doxycycline, the tet-repressor binds to the tetracycline or doxycycline, which inhibits its binding to the tet-operators and thereby increasing expression of the open-reading frame.

The invention further provides a method for inducible expression of a coding segment comprising, providing a first transcriptional unit comprising in operable linkage a hybrid mouse-human CMV promoter comprising a segment of a mouse CMV promoter of SEQ ID NO: 16 upstream from a segment of a human CMV promoter of SEQ ID NO: 13, wherein the hybrid promoter lacks a CG motif at positions corresponding to positions 42 and 43 of SEQ ID NO:13 (human CMV), at least one cumate-operator(s) and a coding segment to be expressed, and a second transcriptional unit comprising in operable linkage a promoter and a segment encoding a cumate-repressor, wherein the cumate-repressor is expressed and in the absence of cumate, the cumate-repressor binds to the cumate-operator(s) inhibiting expression of the coding segment, and in the presence of cumate, the cumate-repressor binds to the cumate, which inhibits its binding to the cumate-operator(s) and thereby increasing expression of the open-reading frame.

Optionally, the first and second transcriptional units are components of the same contiguous DNA molecule. Optionally, the first and second transcriptional units are components of a transposon. Optionally, the transposon is a piggyBac or piggyBac-like transposon. Optionally, the method further comprises introducing the contiguous DNA molecule into a cell.

Optionally, the cell is mammalian. Optionally, the first and second transcriptional units integrate into the genome of the cell. Optionally, the method further comprises culturing the cell. Optionally, the method further comprises supplying tetracycline or doxycycline, or analog thereof, or cumate or an analog thereof to culture media of the cell.

The invention further provides a nucleic acid comprising a transcriptional unit comprising a promoter having a sequence comprising SEQ ID NO:24 in operable linkage with a heterologous coding segment.

Optionally, the promoter lacks a 5' flanking sequence from a natural chimpanzee CMV promoter with which it is naturally associated. Optionally, the nucleic acid further comprises at least first and second tet-operators in operable linkage with the promoter. Optionally, the first and second tet-operators are 5' to the promoter. Optionally, the nucleic acid comprises three, six or eight tet-operators 5' to the promoter. Optionally, the nucleic acid further comprises at least one cumate operator in operable linkage with the promoter. Optionally, the at least one cumate operators is 5' to the promoter. Optionally, the nucleic acid comprises three, six or eight cumate-operator 5' to the promoter.

Optionally, the nucleic acid comprises any of SEQ ID NOS: 164-166 providing the promoter and cumate operators. Optionally, the nucleic acid comprises any of SEQ ID NOS: 167-169 providing the promoter, the operators and a 5' UTR. Optionally, the three, six or eight tet-operators are separated by spacers of 10-25 nucleotides. Optionally, at least some of the spacers differ from one another. Optionally, the nucleic acid further comprises a segment encoding a 5' UTR, for example a 5' UTR having a sequence comprising SEQ ID NO:29. Optionally, the nucleic acid further comprises a second transcriptional unit comprising a second promoter operably linked to a segment encoding a tet-repressor effective to bind a tet-operator in the absence of tetracycline or doxycycline or modified-tet-repressor effective to bind a tet-operator in the presence of tetracycline or doxycycline, wherein the tet-repressor or modified tet-repressor is fused to a transcriptional activator. Optionally, the nucleic acid further comprises a second transcriptional unit comprising a second promoter operably linked to a segment encoding a cumate-repressor effective to bind a cumate-operator in the absence of cumate or modified-cumate-repressor effective to bind a cumate-operator in the presence of cumate, wherein the cumate-repressor or modified cumate-repressor is fused to a transcriptional activator. Optionally, the second transcriptional unit further comprises a polyadenylation sequence. Optionally, the tet-repressor has an amino acid sequence comprising SEQ ID NO:5. Optionally, the modified tet-repressor has an amino acid sequence comprising SEQ ID NO: 6. Optionally, the cumate repressor has an amino acid sequence comprising SEQ ID NO:170. Optionally, the modified cumate-repressor linked to the transcriptional activator has an amino acid sequence comprising SEQ ID NO:172. Optionally, the coding segment encodes a protein, for example a membrane protein, or a therapeutic protein.

The invention further provides a transposon comprising a nucleic acid as described above flanked by inverted repeats of the transposon. Optionally, the transposon further comprises target sites flanking the inverted repeats. Optionally, the transposon is a piggyBac or piggyBac-like transposon.

The invention further provides a cell transformed with the nucleic acid or transposon as described above. Optionally, the cell is mammalian.

The invention further provides a non-human animal transformed with a nucleic acid or transposon as described above. Optionally, the non-human animal is transgenic.

The invention further provides a cell or nonhuman transgenic animal having a genome comprising (a) a promoter having a sequence comprising SEQ ID NO:24 operably linked to at least two tet operons and a coding segment, and (b) a promoter operably linked to a tet-repressor or modified tet-repressor fused to transcriptional activation domain, wherein expression of the coding segment can be regulated by supplying tetracycline or doxycycline to the cell or nonhuman transgenic animal. The invention further provides a cell or nonhuman transgenic animal having a genome comprising (a) a promoter having a sequence comprising SEQ ID NO:24 operably linked to at least two cumate operators and a coding segment, and (b) a promoter operably linked to a cumate-repressor or modified cumate-repressor fused to transcriptional activation domain, wherein expression of the coding segment can be regulated by supplying cumate to the cell or nonhuman transgenic animal.

The invention further provides a method for inducible expression of a coding segment comprising; providing a first transcriptional unit comprising in operable linkage with a least two tet-operators, a promoter having a nucleotide sequence comprising SEQ ID NO: 24 and a coding segment, and a second transcriptional unit comprising in operable linkage a promoter, and a segment encoding a tet-repressor or modified tet-repressor fused to a transcriptional activator, wherein the tet-repressor fused to the transcriptional activator is expressed and in the absence of tetracycline or doxycycline the tet-repressor binds to the at least two tet-operators and expression of the coding segment is increased, or the modified tet-repressor fused to the transcriptional activator is expressed and in the presence of tetracycline or doxycycline the modified tet-repressor binds to the at least two tet-operators and expression of the coding segment is increased. The invention further provides a method for inducible expression of a coding segment comprising; providing a first transcriptional unit comprising in operable linkage with a least two cumate-operators, a promoter having a nucleotide sequence comprising SEQ ID NO: 24 and a coding segment, and a second transcriptional unit comprising in operable linkage a promoter, and a segment encoding a cumate-repressor or modified cumate-repressor fused to a transcriptional activator, wherein the cumate-repressor fused to the transcriptional activator is expressed and in the absence of cumate the cumate-repressor binds to the at least two tet-operators and expression of the coding segment is increased, or the modified cumate-repressor fused to the transcriptional activator is expressed and in the presence of tetracycline or doxycycline the modified cumate-repressor binds to the at least two cumate-operators and expression of the coding segment is increased. Optionally, the first and second transcriptional units are components of the same contiguous DNA molecule. Optionally, the first and second transcriptional units are components of a transposon. Optionally, the transposon is a piggyBac or piggyBac-like transposon. Optionally, the method further comprises comprising introducing the contiguous DNA molecule into a cell. Optionally, the cell is a mammalian cell. Optionally, the first and second transcriptional units integrate into the genome of the cell. Optionally, the method further comprises culturing the cell.

Optionally, the method further comprises supplying tetracycline or doxycycline or analog thereof, or cumate or an analog thereof to culture media of the cell.

BRIEF DESCRIPTION OF THE FIGURES

FIG. 1 shows alignments of mouse (SEQ ID NO:16), human (SEQ ID NO:13) and hybrid (SEQ ID NO:12) CMV promoters. The transcriptional start site is indicated as the underlined G labelled +1. The methylation-sensitive CG dinucleotide in the human sequence is underlined and labelled CpG-179. The TATA boxes of each promoter is underlined.

DEFINITIONS

Figure 2:
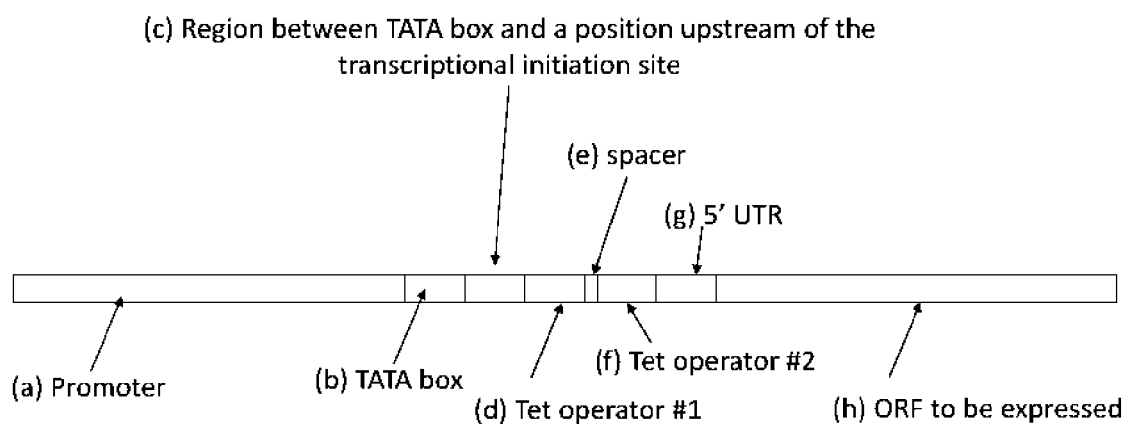
FIGS. 2 and 3 show first and second transcriptional units respectively for a system for tet-inducible expression of an open reading frame ("tet-off").

The singular forms "a," "an," and "the" include plural references unless the context clearly dictates otherwise. Thus, for example, reference to "a nucleic acid" includes a plurality of nucleic acids, reference to "a substrate" includes a plurality of such substrates, reference to "a variant" includes a plurality of variants, and the like.

Terms such as "connected," "attached," "linked," and "conjugated" are used interchangeably to encompass direct as well as indirect connection, attachment, linkage or conjugation unless the context indicates otherwise.

When a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. When a value being discussed has inherent limits, for example where a component can be present at a concentration of from 0 to 100%, or where the pH of an aqueous solution can range from 1 to 14, those inherent limits are specifically disclosed. When a value is explicitly recited, it is to be understood that values which are about the same quantity or amount as the recited value are also within the scope of the invention. When a combination is disclosed, each sub combination of the elements of that combination is also specifically disclosed and is within the scope of the invention. Conversely, when different elements or groups of elements are individually disclosed, combinations thereof are also disclosed. When any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise, all technical and scientific terms used have their ordinary meaning. Singleton, et. al., Dictionary of Microbiology and Molecular Biology, 2nd Ed., John Wiley and Sons, New York (1994), and Hale & Marham, The Harper Collins Dictionary of Biology, Harper Perennial, NY, 1991 provide guidance as to ordinary meaning.

Unless otherwise indicated, nucleic acids are written left to right in 5' to 3' orientation; amino acid sequences are written left to right in amino to carboxy orientation, respectively.

If a DNA sequence is provided, the specification should be understood as additional disclosing the sequence of the RNA, which will be the same with the exception that thymine (T) is replaced with uracil (U), and vice versa.

Nucleic acids are preferably provided with codon preferences for a cell in which expression is intended. The term "codon usage" or "codon bias" refers to the relative frequencies with which different synonymous codons are used to encode an amino acid within an open reading frame. A nucleic acid sequence having codon preferences for a particular target cell has a balance of synonymous codon choices that result in efficient translation in that cell type. This balance is often not calculable from observed genomic codon frequencies, but must be empirically determined, for example as described in U.S. Pat. Nos. 7,561,972 and 7,561,973 and 8,401,798 and in Welch et. al. (2009) "Design Parameters to Control Synthetic Gene Expression in *Escherichia coli*". PLoS ONE 4(9): e7002. https://doi.org/10.1371/journal.pone.0007002. A nucleic acid originally isolated from one cell type to be introduced into a target cell of another type can undergo selection of codon preferences for the target site cell such that at least 1 and sometimes, 5, 20, 15, 20, 50, 100 or more choices among synonymous codons differ between the nucleic acid introduced into the target cell from the original nucleic acid.

Two nucleic acids are "complementary" if the bases of one hydrogen bond to the bases of the other. For perfect complementarity, adenine (A) in the first nucleic acid must correspond with thymine (T) (or uracil for RNA) in the second (and vice versa), and cytosine (C) in the first nucleic acid must correspond with guanine (G) in the second (and vice versa). The two nucleic acid s must also be antiparallel. If two nucleic acid are complementary, one may be described as the "reverse complement" of the other to indicate that their bases are complementary when one is in the 5' to 3' direction and the other is in the 3' to 5' direction. When one nucleic acid sequence is described as complementary to another, it is intended to indicate that the sequences are antiparallel and able to base-pair with one another.

The "configuration" of a nucleic acid refers to the presence, order and direction of functional segments with the nucleic acid.

A 'transposase' is a polypeptide that catalyzes the excision of a corresponding transposon from a donor nucleic acid, for example a vector, and (providing the transposase is not integration-deficient) the subsequent integration of the transposon into a target nucleic acid.

"Transposition" refers to action of a transposase in excising a transposon from one nucleic acid and then integrating it, either into a different site in the same nucleic acid, or into a second nucleic acid.

A "transposon" means a nucleic acid that can be excised from a first nucleic acid, for instance, a vector, and be integrated into a second position in the same nucleic acid, or into a second nucleic acid, for instance, the genomic or extrachromosomal DNA of a cell, by the action of a corresponding trans-acting transposase. A transposon comprises a first transposon end and a second transposon end, which are nucleic acid sequences recognized by and transposed by a transposase. The first and second transposon ends include inverted terminal repeats. Two copies of a transposon target site are usually present on the outside of the transposon ends (one on each side). A transposon usually further comprises a nucleic acid between the two transposon ends, which along with the two transposon ends is transposed by the action of the transposase. In natural transposons, the nucleic acid between the transposon ends is typically a corresponding transposase. Transposons of the present invention are "synthetic transposons" comprising a heterologous nucleic acid, which is transposable by virtue of its juxtaposition between two transposon ends. Synthetic transposons may or may not further comprise flanking nucleic acid sequence(s) outside the transposon ends, such as a sequence encoding a transposase, a vector sequence or sequence encoding a selectable marker.

A "transposon end" means the cis-acting nucleotide sequences that are sufficient for recognition by and transposition by a corresponding transposase. Transposon ends of piggyBac-like transposons comprise perfect or imperfect repeats such that the respective repeats in the two transposon ends are reverse complements of each other. These are referred to as inverted terminal repeats (ITR) or terminal inverted repeats (TIR). A transposon end may or may not include additional sequence proximal to the ITR that promotes or augments transposition.

The terms "corresponding transposon" and "corresponding transposase" are used to indicate an activity relationship between a transposase and a transposon. A transposase transposes its corresponding transposon. Many transposases correspond with a single transposon, and many transposons correspond with a single transposase. The term "orthogonal" refers to a lack of interaction between two systems. A first transposon and its corresponding first transposase and a second transposon and its corresponding second transposase are orthogonal if the first transposase does not excise or transpose the second transposon and the second transposase does not excise or transpose the first transposon.

A "target site" for a transposase is a site or sequence in a molecule into which a transposon can be inserted by a transposase. The piggyBac transposase from *Trichoplusia ni* inserts its transposon predominantly into the target sequence 5'-TTAA-3'. Other useable target sequences for piggyBac transposons are 5'-CTAA-3', 5'-TTAG-3', 5'-ATAA-3', 5'-TCAA-3', 5'-AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-GTAA-3', 5'-AGGT-3', 5'-ATCA-3', 5'-CTCC-3', 5'-TAAA-3', 5'-TCTC-3', 5'-TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-CTGA-3', 5'-GTCC-3', 5'-TAAG-3', 5'-TCTA-3', 5'-TGAG-3', 5'-TGTT-3', 5'-TTCA-3', 5'-TTCT-3' and 5'-TTTT-3' (Li et al., 2013. Proc. Natl. Acad. Sci vol. 110, no. 6, E478-487) and 5'-TTAT. PiggyBac-like transposases transpose their transposons using a cut-and-paste mechanism, which results in duplication of their 4 base pair target sequence on insertion into a DNA molecule. The target sequence is thus found on each side of an integrated piggyBac-like transposon.

A "coupling element" or "translational coupling element" means a DNA sequence that allows the expression of a first polypeptide to be linked to the expression of a second polypeptide. Internal ribosome entry site elements (IRES elements) and cis-acting hydrolase elements (CHYSEL elements) are examples of coupling elements.

A DNA sequence, segment of DNA, RNA sequence or RNA sequence means a contiguous nucleic acid sequence, which can be an oligonucleotide of 2 to 20 nucleotides in length to a full-length genomic sequence of thousands or hundreds of thousands of base pairs.

A vector is a nucleic acid that facilitates any of transfection, integration, replication or expression of a coding segment incorporated into the vector. An expression vector is a vector comprising a promoter which has been or can be operably linked to a coding segment to be expressed. Transfection of the expression vector into a cell allows the cell to express the coding segment. An expression vector can be a genetically engineered plasmid, virus, recombinant virus, or an artificial chromosome derived from, for example, a bacteriophage, adenovirus, adeno-associated virus, retrovirus, lentivirus, poxvirus, or herpesvirus. Such expression vectors can include sequences from bacteria, viruses or phages. Such vectors include chromosomal, episomal and virus-derived vectors, for example, vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids.

A "gene" refers to a transcriptional unit including a promoter and sequence to be expressed from it as an RNA or polypeptide. The sequence to be expressed can be genomic or cDNA or one or more non-coding RNAs including siRNAs or microRNAs among other possibilities. Other elements, such as introns, and other regulatory sequences may or may not be present.

A gene transfer system refers to an expression vector and optionally one or more other features to facilitate gene transfer. For example, a gene transfer system may comprise an expression vector and a lipid or viral packaging mix for enabling a first nucleic acid to enter a cell, or it may comprise a nucleic acid that includes a transposon and a second nucleic acid encoding a corresponding transposase for genomic integration of the transposon. A transposase and transposon of a gene transfer system may be on the same nucleic acid molecule or on different nucleic acid molecules.

Two elements are "heterologous" to one another if not naturally associated. For example, a coding segment linked to a heterologous promoter means a promoter other than that which naturally drives expression of the coding segment. A heterologous nucleic acid flanked by transposon ends or ITRs means a heterologous nucleic acid not naturally flanked by those transposon ends or ITRs, such as a nucleic acid encoding a polypeptide other than a transposase, including an antibody heavy or light chain. A nucleic acid is heterologous to a cell if not naturally found in the cell or if naturally found in the cell but in a different location (e.g., episomal or different genomic location) than the location described.

A "hyperactive" transposase is a transposase that is more active than the naturally occurring transposase from which it is derived. "Hyperactive" transposases are thus not naturally occurring sequences.

An "IRES" or "internal ribosome entry site" means a specialized sequence that directly promotes ribosome binding, independent of a cap structure.

An 'isolated' object, such as a polypeptide or nucleic acid, means the object has been either removed from its natural environment, produced using recombinant techniques, or chemically or enzymatically synthesized. Objects can also be purified, that is, provided at least 90%, 95% or 99% free w/w of other materials with which they are naturally associated or are used in their production or purification. The terms isolated and purified do not exclude presence of other components not naturally associated with the object that facilitate its use, such as a heterologous promoter for a coding segment, or pharmaceutical excipient.

Unless otherwise apparent from the context, the terms "nucleoside" and "nucleotide" include those moieties which contain not only the standard purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, for example, where one or more of the hydroxyl groups are replaced with halogen, aliphatic groups, or is functionalized as ethers, amines, or the like. The term "nucleotidic unit" encompasses nucleosides and nucleotides.

An "Open Reading Frame" or "ORF" means a portion of a nucleic acid that, when translated into amino acids, contains no stop codons. An open reading frame presumptively encodes a polypeptide. The genetic code reads DNA sequences in groups of three base pairs, which means that a double-stranded DNA molecule can read in any of six possible reading frames-three in the forward direction and three in the reverse. An ORF typically also includes an initiation codon at which translation may start.

The term "operably linked" refers to functional linkage between two sequences such that one sequence operationally modifies the behavior of the other. For example, a promoter is operably linked to a coding segment when the promoter can initiate transcription of the coding segment, optionally with subsequent translation of the transcript. A promoter is operably linked to one or more tet-operators, when initiation of transcription by the promoter can be regulated by binding of a tet-repressor or modified tet-repressor to the tet-operon. A mature polypeptide and signal peptide are operably linked when the signal peptide regulates secretion or subcellular location of the mature polypeptide.

The term "overhang" or "DNA overhang" means the single-stranded portion at the end of a double-stranded DNA molecule. Complementary overhangs are those which will base-pair with each other.

A "piggyBac-like transposase" means a transposase with at least 20% amino acid sequence identity as identified using the TBLASTP algorithm to the piggyBac transposase from *Trichoplusia ni* (SEQ ID NO:116), and as more fully described in Sakar, A. et. al., 2003. Mol. Gen. Genomics 270: 173-180. "Molecular evolutionary analysis of the widespread piggyBac transposon family and related 'domesticated' species", and further characterized by a DDE-like DDD motif, with aspartate residues at positions corresponding to D268, D346, and D447 of *Trichoplusia ni* piggyBac transposase on maximal alignment. PiggyBac-like transposases are also characterized by their ability to excise their transposons precisely with a high frequency. A "piggyBac-like transposon" means a transposon having transposon ends which are the same or at least 80% and preferably at least 90, 95, 96, 97, 98, 99% or 100% identical to the nucleotide sequences of the transposon ends of a naturally occurring transposon that encodes a piggyBac-like transposase. A piggyBac-like transposon includes an inverted terminal repeat (ITR) sequence of approximately 12-16 bases at each end. These repeats may be identical at the two ends, or the repeats at the two ends may differ at 1 or 2 or 3 or 4 positions in the two ITRs. The transposon is flanked on each side by a 4 base sequence corresponding to the integration target sequence which is duplicated on transposon integration (the Target Site Duplication or Target Sequence Duplication or TSD). PiggyBac-like transposons and transposases occur naturally in a wide range of organisms including *Argyrogramma agnate* (GU477713), *Anopheles gambiae* (XP_312615; XP_320414; XP_310729), *Aphis gossypii* (GU329918), *Acyrthosiphon pisum* (XP_001948139), *Agrotis ypsilon* (GU477714), *Bombyx mori* (BAD11135), *Ciona intestinalis* (XP_002123602), *Chilo suppressalis* (JX294476), *Drosophila melanogaster* (AAL39784), *Daphnia pulicaria* (AAM76342), *Helicoverpa armigera* (ABS18391), *Homo sapiens* (NP_689808), *Heliothis virescens* (ABD76335), *Macdunnoughia crassisigna* (EU287451), *Macaca fascicularis* (AB179012), *Mus musculus* (NP_741958), *Pectinophora gossypiella* (GU270322), *Rattus norvegicus* (XP_220453), *Tribolium castaneum* (XP_001814566) and *Trichoplusia ni* (AAA87375) and *Xenopus tropicalis* (BAF82026), although transposition activity has been described for almost none of these.

A regulatory element such as promoter is active in a specified target cell, such as a mammalian cell, means a regulatory element configurable to result in a level of expression of at least 1 transcript and optionally at least ten, 100 or 1000 transcripts per cell in a mammalian cell into which the regulatory element has been introduced.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the longer of (a) entire length of the shorter of the two sequences being compared, or (b) at least 25 contiguous nucleotides. Matched positions in maximally aligned sequences can be referred to as corresponding to one another.

Specific binding between two entities refers to binding detectably higher in magnitude and distinguishable from non-specific binding of each of the entities to at least one unrelated target. Specific binding can be the result of formation of bonds between particular functional groups or particular spatial fit (e.g., lock and key type) whereas nonspecific binding is usually the result of van der Waals forces. Exemplary specific binding affinity can be at least $10^7$, $10^8$, $10^9$, or $10^{10}$ M$^{-1}$.

Preferential binding between two entities refers to a substantial difference in binding affinity between two different conditions, such as presence or absence of tetracycline. For example, the affinities can differ by a factor of a least 5, 10, 25, 50 or 100. Preferential expression in one condition compared with another likewise refers to variation in expression by a factor of at least 5, 10, 25, 50 or 100 between the conditions.

A polypeptide refers to any polymer of amino acids natural or synthetic regardless of length and thus includes full length proteins, fragments thereof, and peptides.

A promoter can be represented by a single-stranded sequence of nucleotides present on a transcribed strand or a double-stranded sequence of nucleotide formed of the single-stranded sequence of nucleotides just described duplexed with its complement. Depending on the context, reference to a promoter may refer to either single- or double-stranded forms or both.

Transfection is used generically for any process for introducing a nucleic into cells.

The term "comprising" indicates that other features besides those recited may or may not be present. Thus, for example, reference to a nucleic acid comprising a tet-operator comprising SEQ ID NO:5 means that additional flanking residues can be present on either or both sides of SEQ ID NO:5. The term "consisting essentially of" is used in accordance with convention to refer to the basic and novel features of an invention.

DETAILED DESCRIPTION

I. General

The invention provides inducible promoter systems and their components incorporating components of a tetracycline operon. By coordinating expression of different transcriptional units in these systems as a result of selection of promoters and/or linking the units into the same DNA molecule, these systems can achieve higher levels of expression of coding segments of interest, increased differential levels of expression between on- and off-states, and/or greater responsiveness to inducing agents than conventional systems.

II. Promoters

The invention provides a hybrid mouse-human CMV promoter. The sequences of mouse and human CMV promoters are set out aligned in FIG. 1 with the transcriptional start site (first transcribed nucleotide) indicated as the underlined G annotated as +1. The human CMV promoter is a constitutive promoter often used for expression in mammalian cells. However, this promoter contains several CG dinucleotide motifs, which may reduce transcriptional efficiency, particularly a CG motif occupying positions -178 and -179 counted from the transcriptional start site of human CMV promoter (corresponding to positions 42 and 43 of SEQ ID NO:13, or corresponding positions of any mouse-human chimeric promoter sequence maximally aligned with SEQ ID NO:13). CG motifs can be eliminated by replacing sequence from the human CMV promoter with aligned sequence from the mouse CMV promoter lacking one or more of the CG motifs, particularly the CG motif occupying positions -178 and -179 of the human CMV promoter sequence (SEQ ID NO:13). Among other possibilities, replacement can be effected by combining an upstream segment of a mouse CMV promoter of SEQ ID NO:16 and a downstream segment of a human CMV promoter of SEQ ID NO:13 or 14. The junction between the segments is preferably within a segment of nucleotides ACGT-CAATGGGA, which is common to the human and mouse CMV promoter sequences. One hybrid comprises 149 bp of the mouse CMV sequence of SEQ ID NO:16 upstream of 114 bp of the human CMV sequence of SEQ ID NO:13. Preferred promoters have sequences comprising, consisting of or consisting essentially of the sequence of SEQ ID NO:10. SEQ ID NO:10 lacks a 13 nucleotide sequence (SEQ ID NO:35) immediately upstream of the human CMV transcription initiation site. The omitted sequence can be replaced by regulatory elements, such as tet operons as further described below. Another preferred promoter sequence comprises, consists essentially of or consists of SEQ ID NO:12. SEQ ID NO:12 includes the 13 nucleotide sequence of SEQ ID NO:35 omitted in SEQ ID NO:10. Although exemplified for a combination of human and mouse CMV promoters, the same principles can be applied in forming a hybrid promoter between a human CMV promoter and CMV promoters of other species, particularly rodent species, such as rat CMV. Hybrid promoters, as described above, preferably confer enhanced transcription compared with either or both of the component promoters forming the hybrid.

The invention also provides a minimal chimpanzee CMV promoter. A minimal promoter is a promoter that by itself shows no or minimal transcription (e.g., a mean of <1, 5 or 10 transcripts per cell), but which can show substantially enhanced transcription (e.g., at least 10-fold, 50-fold or 100-fold), when combined with an upstream regulatory sequence, which serves to recruit a polymerase and transcriptional factors. A minimal promoter sequence is typically a contiguous sequence of nucleotides starting at or near the first nucleotide upstream of the transcriptional initiation site and including a TATA box. An exemplary minimal chimpanzee CMV promoter has a sequence comprising, consisting of or consisting essentially of SEQ ID NO:24. Optionally, up to 1, 2, 3, 4 or 5 nucleotides can be deleted from either end. Optionally, a few, e.g., up to 1, 2, 3, 4, 5, 6, 7, 8, 9, or 10 nucleotides from the chimpanzee CMV promoter can be included upstream from the minimal promoter sequence, but inclusion of additional nucleotides is not preferred because this may reduce the differential levels of expression in the presence and absence of upstream activation.

The invention also uses intermediate strength promoters. Such promoters have reduced transcriptional activity relative to the hybrid promoters described above or their component promoters but greater activity than a minimal promoter. For example, the transcriptional activity can be reduced by 2-20 fold relative to the hybrid promoters described above or their components. Examples of such promoters have sequences comprising, consisting of or consisting essentially of any of SEQ ID NOS:17-21.

The invention can also make use of other strong promoters besides the hybrid promoters and their components described above. Such promoters are preferably active in eukaryotic cells, more preferably in mammalian cells. Examples of such strong promoters are CMV, EF1a (human elongation factor 1-alpha), SV40, PGK1 (phosphoglycerate kinase), human ubiquitin C, and human beta actin.

The promoters described above can be incorporated into transcriptional units, which in addition to the promoter include a coding segment, and sometimes other regulatory sequences, such as tet-operators as described further below or an enhancer, among other components. The heterologous coding segment can encode a polypeptide or RNA and can include a 5'UTR and/or a 3' UTR and a polyadenylation sequence among other components. Such transcriptional units can be transformed into cells for expression.

Promoters can be compared by forming otherwise identical transcriptional units between promoters to be compared, transforming into the same cell type, e.g., CHO, HeLa, 293, COS, U2OS, 3T3, or other mammalian cell and comparing transcription levels.

III. Components of Tet Regulatory Systems

Some of the components of the present systems can be the same as those of conventional tet-dependent regulatory systems. Such components include tet-operators, tet-repressors, which bind tet-operators in the absence of tetracycline or other analogs thereof, modified tet-repressors, which bind tet-operators in the presence of tetracycline or other analogs thereof, and inducers, such as tetracycline and analogs thereof.

An exemplary tet-operator comprises, consists of, or consists essentially of the sequence of SEQ ID NO:1 Other tet-operators can have up to 1, 2, 3 or 4 substitutions, deletions or additions and/or have at least 90, 95, 97, 98 or 99% identity relative to the exemplified sequence and retain the ability of the exemplified sequence for preferential binding of a tet-repressor in the absence of tetracycline and preferential binding of a modified tet-repressor in the presence of tetracycline. Examples of other tet-operator sequences include 5'-TCGCTATCAGTGATAGAGA-3' and 5'-ACTCTATCATTGATAGAGT-3' (Wissmann et al, 1986, Nucl. Acids Res. 14: 4253-4266). Tet-operators are typically used in tandem arrays (i.e, including at least two tet operator sequences). Some arrays include 2 to 10 tet-operator sequences. Some such arrays include 2, 3, 4, 5, 6, 7, 8, 9 or 10 operator sequences. Some arrays have at least 2, 3, 4, 5, 6, 7, 8, 9 or 10 operator sequences. Some arrays have more than 10 operator sequences. The multiple operator sequences in such a tandem array are typically the same sequence. The operators are typically separated by spacers of e.g., 1-25 nucleotides. The identity and length of spacers can vary between different operators in an array. The number of operators and length of spacer can vary depending on the location of the operators relative to other components of a transcriptional unit as further described below.

An exemplary tet-repressor polypeptide comprises or consists of the amino acid sequence SEQ ID NO:5. Other tet-repressor polypeptides can have up to 1, 2, 3, 4, 5, 6, 7, 8, 9 or 10 substitutions, deletions or additions and/or have at least 90, 95, 97, 98 or 99% identity relative to this sequence. Examples of variants include those described in Gossen and Bujard, Proc. Natl. Acad. Sci. USA Vol. 89, pp. 5547-5551, 1992 and a T40A substitution described by Altschmied et al., EMBO J. 7:4011-4017, (1988). Substitutions are numbered according to position in SEQ ID NO:5 or if present in a sequence with a different number of residues than SEQ ID NO:5, the position of SEQ ID NO:5 corresponding to the substitution when the sequences are maximally aligned. A tet-repressor polypeptide has the property of specifically binding to a tet-operator or an array thereof in the absence of tetracycline. A tet-repressor shows at least preferential binding to a tet-operator or array thereof in the absence of tetracycline compared with the presence of tetracycline.

An exemplary modified tet-repressor polypeptide comprises or consists of the amino acid sequence SEQ ID NO:6. Other modified tet-repressor polypeptides can have up to 1, 2, 3, 4, 5, 6, 7, 8, 9 or 10 substitutions, deletions or additions and/or have at least 90, 95, 97, 98 or 99% identity relative to this sequence. Examples of variants include those described in Das et al. Current Gene Therapy, 2016, 16, 156-167, including tTA (E71K D95N L101S G102D), S2 (E19G A56P D148E H179R), M2 (S12G E19G A56P D148E H179R), $2^s$-S2 (E19G A56P D148E H179R), $2^s$-M2 (S12G E19G A56P D148E H179R), V1 (E19G A56P F86Y D148E H179R), rtTA3 (S12G E19G A56P F86Y D148E H179R), V10 (E19G A56P F67S F86Y D148E R171K H179R), V16 (V9I E19G A56P F67S F86Y D148E R171K H179R). Substitutions are numbered according to position in SEQ ID NO:6 or if present in a sequence with a different number of residues than SEQ ID NO:6, the position of SEQ ID NO:6 corresponding to the substitution when the sequences are maximally aligned. In contrast to a tet-repressor polypeptide, a modified tet-repressor polypeptide has the property of specifically binding to a tet-operator or an array thereof in the presence of tetracycline. A modified tet-repressor shows at least preferential binding to a tet-operator or array thereof in the presence of tetracycline compared with the absence of tetracycline.

Inducers of expression used in the present system include tetracycline itself, doxycycline and other tetracycline analogs. Unless otherwise apparent from the context, reference to tetracycline should be understood as alternatively disclosing that tetracycline analogs can be used. A tetracycline analog is a compound structurally related to tetracycline and which specifically binds to a tet-repressor or modified tet-repressor as described herein. Examples of tetracycline analogs are anhydrotetracycline (atc), chlorotetracycline, oxytetracycline, or deoxytetracycline and minocycline. Further analogs are disclosed by Hlavka and Boothe, "The Tetracyclines," in Handbook of Experimental Pharmacology 78, R. K. Blackwood et al. (eds.), Springer-Verlag, Berlin, N.Y., 1985; Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; Evans, "The Technology of the Tetracyclines," Biochemical Reference Series 1, Quadrangle Press, New York, 1968; and Dowling, "Tetracycline," Antibiotic Monographs, no. 3, Medical Encyclopedia, N.Y., 1955 and WO2007/133797 and WO2007/133798.

III. Components of Cumate Regulatory Systems

A cumulate regulatory system has analogous compounds and mode of operation to a tetracycline regulatory system. These include cumate operators, cumate repressors, which bind a cumate operator in the absence of cumate and modified cumate repressors, which bind cumate operators in the presence of cumate. The description in relation to tetracycline regulatory sequences applies mutatis mutandis to cumate operator systems.

An exemplary cumate operator comprises, consists of, or consists essentially of the sequence of any of SEQ ID NOS:156-158. Other cumate operators can have up to 1, 2, 3 or 4 substitutions, deletions or additions and/or have at least 90, 95, 97, 98 or 99% identity relative to the exemplified sequence and retain the ability of the exemplified sequence for preferential binding of a cumate repressor in the absence of cumate and preferential binding of a modified cumate repressor in the presence of cumate. Cumate operators can be used individually or in tandem arrays (i.e., including at least two cumate operators). Some arrays include 2 to 10 cumate operators. Some such arrays include 2, 3, 4, 5, 6, 7, 8, 9 or 10 operator sequences. Some arrays have at least 2, 3, 4, 5, 6, 7, 8, 9 or 10 operator sequences. Some arrays have more than 10 operator sequences. The multiple operators in such a tandem array can have the same or different sequences. The operators may be separated by spacers of e.g., 1-25 nucleotides. The identity and length of spacers can vary between different operators in an array. The number of operators and length of spacer can vary depending on the location of the operators relative to other components of a transcriptional unit as further described below.

An exemplary cumate repressor polypeptide comprises or consists of the amino acid sequence SEQ ID NO:170. Other cumate-repressor polypeptides can have up to 1, 2, 3, 4, 5, 6, 7, 8, 9 or 10 substitutions, deletions or additions and/or have at least 90, 95, 97, 98 or 99% identity relative to this sequence. A cumate repressor polypeptide has the property of specifically binding to a cumate operator or an array thereof in the absence of cumate. A cumate-repressor shows at least preferential binding to a cumate operator or array thereof in the absence of cumate compared with the presence of tetracycline.

An exemplary modified cumate repressor polypeptide comprises or consists of the amino acid sequence SEQ ID NO:171. Other modified cumate repressor polypeptides can have up to 1, 2, 3, 4, 5, 6, 7, 8, 9 or 10 substitutions, deletions or additions and/or have at least 90, 95, 97, 98 or 99% identity relative to this sequence. SEQ ID NO:171 includes three mutations relative to SEQ ID NO:170: E142G, I144M and V125A In contrast to a cumate repressor polypeptide, a modified cumate repressor polypeptide has the property of specifically binding to a cumate-operator or an array thereof in the presence of cumate. A modified cumate repressor shows at least preferential binding to a tet-operator or array thereof in the presence of tetracycline compared with the absence of tetracycline.

Inducers of expression used in the present system include cumate itself and analogs. An analog is a compound structurally related to cumate and which specifically binds to a cumate-repressor or modified cumate-repressor as described herein. Examples of cumate analogs include di-methyl p-aminobenzoic acid (DM PABA), trimethyl cumate, and ethylbenzoate, or a salt thereof, mainly para- or 4-substituted benzoate consisting of a bulky group of heteroatom, such as those selected from the group consisting of 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allytoluene, 4-fluoro-p-toluate, 3-chloro-p-toluate, and 4-bromo-m-toluate, an analogue of cumate such as Benzoic acid, p-methylbenzoic acid, p-ethylbenzoic acid, p-Propylbenzoic acid, cumic acid, p-isobutylbenzoic acid, p-tert-butylbenzoic acid, ibuprofen, p-aminobenzoic acid, p-N-methylaminobenzoic acid, p-N-dimethylaminobenzoic acid, p-N-methyl-N-ethylaminobenzoic acid and p-N-ethylaminobenzoic acid.

IV. Transcriptional Activation Domains

Some of the present systems include a transcriptional activation domain. Such a domain is expression as a fusion protein with a tet-repressor polypeptide or modified tet-repressor polypeptide. Fusion is preferably between the C-terminus of the tet-repressor or modified-tet-repressor and the N-terminus of the transcriptional activation domain. More than one transcriptional domain can be included as a tandem array of such domains in a fusion protein. Examples of transcriptional activations domains include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)). Other transcriptional activation domains include VP64, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15, 348-15, 353. Exemplary VP16 activation domains comprises or consists of a sequence selected from SEQ ID NOS:7 or 40. Exemplary fusions of a modified tet-repressor to a VP16 activation domain comprises or consists of a sequence selected from SEQ ID NOS:8 or 9.

V. Coding Segments

Coding segments can encode any polypeptide or RNA of interest. Coding segments can include an open reading frame encoding a polypeptide. Coding segments can also include a segment encoding a 5' UTR, 3' UTR or polyadenylation region. Examples of polypeptides includes therapeutic proteins, proteins associated with a disease phenotype, enzymes, proteins used as selection markers or counter-selection markers, or suicide proteins. Examples of RNA include mRNA, tRNA, rRNA as well as various RNA molecules used for interference of expression, such as anti-sense, siRNA, shRNA or micro-RNA including artificial micro-RNA. Some examples of therapeutic proteins include antibodies or their component heavy and light chains, or heavy and light chain fused to one another as a single-chain antibody, antibodies engineered to produce heteromeric multi-chain molecules capable of binding more than one target protein (e.g. bispecific or multi-specific antibodies), T cell engagers, chimeric antigen receptors combining an antigen binding region with transmembrane and T cell signalling domains, Fc fusion proteins, antigens from pathogens (e.g. for use in vaccines), anticoagulants, blood factors, bone morphogenetic proteins, enzymes, growth factor hormones, interferons, interleukins and thrombolytics. Proteins associated with disease are often mutated forms of human proteins. Some examples of such proteins are huntingtin, cystic fibrosis trans-membrane regulator, hemoglobin, alpha-1 antitrypsin, phenylalanine hydroxylase, beta-hexosaminidase, amyloid precursor protein, alpha-synuclein prion protein, transthyretin, crystallin and p53. It is particularly useful to be able to control the timing of expression of coding segments whose expression can be toxic for the cell that expresses them, for example so that the growth phase of an expression host can be decoupled from the expression phase. Examples of potentially toxic coding segments include open reading frames encoding membrane proteins such as ion channels, G-protein coupled receptors (GPCRs) and viral membrane proteins (such as the coronavirus spike proteins). Other examples of potentially toxic coding segments include open reading frames encoding proteins normally targeted to the lysozome, kinases and cytokines.

A selection marker is a nucleic acid or expression product that allows for selection of a molecule or cell containing the marker often under particular conditions. These markers can encode an activity, such as, production of RNA, peptide, or protein, or can provide a binding site for RNA, peptides, proteins, inorganic and organic compounds or compositions. Examples of selectable markers include: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds. Some examples of selection markers include glutamine synthetase, dihydrofolate reductase, blasticidin-resistance, neo-resistance, hygromycin-resistance, puromycin-resistance and zeocin-resistance.

The term "counter-selectable marker" means a polynucleotide sequence that confers a selective disadvantage on a host cell. Examples of counter-selectable markers include sacB, rpsL, tetAR, pheS, thyA, gata-1, ccdB, kid and barnase (Bernard, 1995, Journal/Gene, 162: 159-160; Bernard et. al., 1994. Journal/Gene, 148: 71-74; Gabant et. al., 1997, Journal/Biotechniques, 23: 938-941; Gababt et. al., 1998, Journal/Gene, 207: 87-92; Gababt et. al., 2000, Journal/Biotechniques, 28: 784-788; Galvao and de Lorenzo, 2005, Journal/Appl Environ Microbiol, 71: 883-892; Hartzog et. al., 2005, Journal/Yeat, 22:789-798; Knipfer et. al., 1997, Journal/Plasmid, 37: 129-140; Reyrat et. al., 1998, Journal/Infect Immun, 66: 4011-4017; Soderholm et. al., 2001, Journal/Biotechniques, 31: 306-310, 312; Tamura et. al., 2005, Journal/Appl Environ Microbiol, 71: 587-590; Yazynin et. al., 1999, Journal/FEBS Lett, 452: 351-354).

A suicide gene is a gene that causes a cell to kill itself e.g., by inducing apoptosis or by metabolizing a pro-drug into a drug that is toxic to a cell, e.g., caspase-9 (see Yagyu et al., Mol. Ther. 23: 1475-85 (2015)). The present systems are particularly useful for regulated expression of coding segments whose expression is detrimental or lethal to a cell.

VI. Gene Transfer Systems

The present transcription units can be incorporated into one or more gene transfer systems. For inducible control systems including two transcriptional units, both are preferably included in the same gene transfer system as part of the same contiguous nucleic acid.

A gene transfer systems comprises a nucleic acid to be transferred into a host cell and one or more other elements to facilitate uptake, integration, expression or election of the nucleic acid. A gene transfer system can include a transposon and corresponding transposase. Although transposons are preferred gene transfer systems because of their large cargo sizes and because multiple different coding segments with all of their associated regulatory elements can be incorporated without compromising packaging and delivery of the gene transfer system, other genes transfer systems including a lentiviral system, an adenoviral system or an adeno-associated viral system, or other expression vector can be used.

A gene transfer system or one or more if its components can be transfected into one or more cells by techniques such as particle bombardment, electroporation, microinjection, combining the components with lipid-containing vesicles, such as cationic lipid vesicles, DNA condensing reagents (example, calcium phosphate, polyline or polyethyleneimine)

After transfection, introduced nucleic acids can remain the cytoplasm (e.g., as an episome) or can be integrated into the genome. Integration of a nucleic acid into the genome of a host cell generally makes it stably heritable, by subjecting it to the same mechanisms that ensure the replication and division of genomic DNA. Such stable heritability is desirable for achieving good and consistent expression over long growth periods.

Nucleic acid can be efficiently integrated into nucleic acids, such as a genome, by a transposase system. The nucleic acid into which a transposed nucleic acid is integrated is sometimes referred to as a target nucleic acid. A transposase system includes a transposon and a corresponding transposase. The transposon includes a heterologous nucleic acid to be transposed flanked by inverted transposon repeats (ITRs). The ITR on one side of the heterologous nucleic acid is a perfect or substantial (e.g., one or two mismatched nucleotides) reverse complement of the ITR on the other side. Between the ITRs and heterologous nucleic acids, additional transposon sequences may be present. Outside the ITRs (distal to the heterologous nucleic acid) are two copies, one for each side, of a target site, typically of four nucleotides. A benefit of a transposon is that the entire nucleic acid between transposon inverted terminal repeats (ITRs) can be integrated. There are several different classes of transposon. piggyBac and piggyBac-like transposons include the piggyBac transposon from the looper moth *Trichoplusia ni, Xenopus* piggyBac-like transposons,

*Bombyx* piggyBac-like transposons, *Heliothis* piggyBac-like transposons, *Helicoverpa* piggyBac-like transposons, *Agrotis* piggyBac-like transposons, *Amyelois* piggyBac-like transposons, piggyBat piggyBac-like transposons and *Oryzias* piggyBac-like transposons. hAT transposons include TcBuster. Mariner transposons include Sleeping Beauty. Each of these transposons can be integrated into the genome of a mammalian cell by a corresponding transposase. A transposase can be provided as a protein or encoded by a nucleic acid. A transposon comprising a heterologous nucleic acid and its corresponding transposase can be transfected into a cell at the same time, or sequentially. For example, a transposase protein or its encoding nucleic acid may be transfected into a cell prior to, simultaneously with or subsequently to transfection of a corresponding transposon. Additionally, administration of either component of the gene transfer system may occur repeatedly, for example, by administering at least two doses of this component.

A nucleic acid encoding a transposase protein can be transfected into a cell as a nucleic acid vector such as a plasmid, a viral vector or as an mRNA molecule. The nucleic acid can be circular or linear. The nucleic acid encoding the transposase protein can be stably inserted into the genome of the cell or can remain in the cytoplasm. The transposase can be expressed constitutively or from an inducible system. DNA encoding a transposase is preferably linked to a promoter. A variety of promoters can be used including constitutive promoters, tissue-specific promoters, inducible promoters, species-specific promoters, cell-type specific promoters and the like. Alternatively, a transposase can be introduced into a cell directly as protein, for example using cell-penetrating peptides (e.g. as described in Ramsey and Flynn, 2015. Pharmacol. Ther. 154: 78-86 "Cell-penetrating peptides transport therapeutics into cells"); using small molecules including salt plus propane betaine (e.g. as described in Astolfo et. al., 2015. Cell 161: 674-690); or electroporation (e.g. as described in Morgan and Day, 1995. Methods in Molecular Biology 48: 63-71 "The introduction of proteins into mammalian cells by electroporation").

Transposase proteins can be introduced into cells encoded as an mRNA molecule. RNA molecules can include substitutions to reduce toxicity effects on the cell, for example substitution of uridine with pseudouridine, and substitution of cytosine with 5-methyl cytosine. mRNA encoding the transposase can be prepared with a 5'-cap structure to improve expression in a target cell. Exemplary cap structures are a cap analog (G(5')ppp(5')G), an anti-reverse cap analog (3'-O-Me-m.sup.7G(5')ppp(5')G, a clean cap(m7G(5')ppp(5')(2'OMeA)pG), an mCap (m7G(5')ppp(5)G). mRNA encoding the transposase may be prepared such that some bases are partially or fully substituted, for example uridine may be substituted with pseudo-uridine, cytosine may be substituted with 5-methyl-cytosine. Any combinations of these caps and substitutions may be made. Similarly, a nucleic acid encoding a transposase protein or the transposon of this invention can be transfected into the cell as a linear fragment or as a circularized fragment, either as a plasmid or as recombinant viral DNA. If the transposase is introduced as a DNA sequence encoding the transposase, then the coding segment encoding the transposase is preferably operably linked to a promoter suitable for use in the intended target cell.

An exemplary piggyBac-like transposon for modifying the genome of a mammalian cell is a *Xenopus* transposon which comprises an ITR with the with sequence given by SEQ ID NO:41, a heterologous nucleic acid to be transposed and a second ITR with sequence given by SEQ ID NO:42.

The transposon may further be flanked by a copy of the tetranucleotide5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:43 or 44 on one side of the heterologous nucleic acid, preferably the left side, and a sequence immediately adjacent to the ITR and proximal to the heterologous nucleic acid that is at least 95% or 100% identical to SEQ ID NO:45 or 46 on the other side of the heterologous nucleic acid, preferably the right side. This transposon may be transposed by a corresponding *Xenopus* transposase comprising a sequence at least 90% or 100% identical to the sequence given by SEQ ID NO:47 or 48, for example, any of SEQ ID NOS:47-79. Preferably the transposase is a hyperactive variant of a naturally occurring transposase. Preferably the hyperactive variant transposase comprises one or more of the following amino acid changes, relative to the sequence of SEQ ID NO:47: Y6L, Y6H, Y6V, Y6I, Y6C, Y6G, Y6A, Y6S, Y6F, Y6R, Y6P, Y6D, Y6N, S7G, S7V, S7D, E9W, E9D, E9E, M16E, M16N, M16D, M16S, M16Q, M16T, M16A, M16L, M16H, M16F, M16I, S18C, 518Y, S18M, S18L, S18Q, S18G, S18P, S18A, S18W, S18H, S18K, S18I, S18V, S19C, S19V, S19L, S19F, S19K, S19E, S19D, S19G, S19N, S19A, S19M, S19P, 519Y, S19R, S19T, S19Q, S20G, 520M, S20L, S20V, S20H, S20W, S20A, S20C, S20Q, S20D, S20F, S20N, S20R, E21N, E21W, E21G, E21Q, E21L, E21D, E21A, E21P, E21T, E21S, E21Y, E21V, E21F, E21M, E22C, E22H, E22R, E22L, E22K, E22S, E22G, E22M, E22V, E22Q, E22A, E22Y, E22W, E22D, E22T, F23Q, F23A, F23D, F23W, F23K, F23T, F23V, F23M, F23N, F23P, F23H, F23E, F23C, F23R, F23Y, S24L, S24W, 524H, S24V, S24P, S24I, S24F, S24K, 524Y, S24D, S24C, 524N, 524G, S24A, S26F, S26H, S26V, S26Q, S26Y, S26W, S28K, S28Y, S28C, S28M, S28L, S28H, S28T, S28Q, V31L, V31T, V31I, V31Q, V31K, A34L, A34E, L67A, L67T, L67M, L67V, L67C, L67H, L67E, L67Y, G73H, G73N, G73K, G73F, G73V, G73D, G735, G73W, G73L, A76L, A76R, A76E, A76I, A76V, D77N, D77Q, D77Y, D77L, D77T, P88A, P88E, P88N, P88H, P88D, P88L, N91D, N91R, N91A, N91L, N91H, N91V, Y141I, Y141M, Y141Q, Y141S, Y141E, Y141W, Y141V, Y141F, Y141A, Y141C, Y141K, Y141L, Y141H, Y141R, N145C, N145M, N145A, N145Q, N145I, N145F, N145G, N145D, N145E, N145V, N145H, N145W, N145Y, N145L, N145R, N145S, P146V, P146T, P146W, P146C, P146Q, P146L, P146Y, P146K, P146N, P146F, P146E, P148M, P148R, P148V, P148F, P148T, P148C, P148Q, P148H, Y150W, Y150A, Y150F, Y150H, Y150S, Y150V, Y150C, Y150M, Y150N, Y150D, Y150E, Y150Q, Y150K, H157Y, H157F, H157T, H157S, H157W, A162L, A162V, A162C, A162K, A162T, A162G, A162M, A162S, A162I, A162Y, A162Q, A179T, A179K, A179S, A179V, A179R, L182V, L182I, L182Q, L182T, L182W, L182R, L182S, T189C, T189N, T189L, T189K, T189Q, T189V, T189A, T189W, T189Y, T189G, T189F, T189S, T189H, L192V, L192C, L192H, L192M, L192I, S193P, S193T, S193R, S193K, S193G, S193D, S193N, S193F, S193H, S193Q, S193Y, V196L, V196S, V196W, V196A, V196F, V196M, V196I, S198G, S198R, S198A, S198K, T200C, T200I, T200M, T200L, T200N, T200W, T200V, T200Q, T200Y, T200H, T200R, S202A, S202P, L210H, L210A, F212Y, F212N, F212M, F212C, F212A, N218V, N218R, N218T, N218C, N218G, N218I, N218P, N218D, N218E, A248S, A248L, A248H, A248C, A248N, A248I, A248Q, A248Y, A248M, A248D, L263V, L263A, L263M, L263R, L263D, Q270V, Q270K, Q270A, Q270C, Q270P, Q270L, Q270I, Q270E, Q270G, Q270Y, Q270N, Q270T, Q270W, Q270H, S294R, S294N, S294G, S294T, S294C, T297C, T297P, T297V, T297M, T297L, T297D, E304D, E304H, E304S, E304C, S308R, S308G, L310R, L310I, L310V, L333M, L333W, L333F, Q336Y, Q336N, Q336M, Q336A, Q336T, Q336L, Q336I, Q336G, Q336F, Q336E, Q336V, Q336C, Q336H, A354V, A354W, A354D, A354C, A354R, A354E, A354K, A354H, A354G, C357Q, C357H, C357W, C357N, C357I, C357V, C357M, C357R, C357F, C357D, L358A, L358F, L358E, L358R, L358Q, L358V, L358H, L358C, L358M, L358Y, L358K, L358N, L358I, D359N, D359A, D359L, D359H, D359R, D359S, D359Q, D359E, D359M, L377V, L377I, V423N, V423P, V423T, V423F, V423H, V423C, V423S, V423G, V423A, V423R, V423L, P426L, P426K, P426Y, P426F, P426T, P426W, P426V, P426C, P426S, P426Q, P426H, P426N, K428R, K428Q, K428N, K428T, K428F, S434A, S434T, S438Q, S438A, S438M, T447S, T447A, T447C, T447Q, T447N, T447G, L450M, L450V, L450A, L450I, L450E, A462M, A462T, A462Y, A462F, A462K, A462R, A462Q, A462H, A462E, A462N, A462C, V467T, V467C, V467A, V467K, I469V, I469N, I472V, I472L, I472W, I472M, I472F, L476I, L476V, L476N, L476F, L476M, L476C, L476Q, P488E, P488H, P488K, P488Q, P488F, P488M, P488L, P488N, P488D, Q498V, Q498L, Q498G, Q498H, Q498T, Q498C, Q498E, Q498M, L502I, L502M, L502V, L502G, L502F, E517M, E517V, E517A, E517K, E517L, E517G, E517S, E517I, P520W, P520R, P520M, P520F, P520Q, P520V, P520G, P520D, P520K, P520Y, P520E, P520L, P520T, S521A, S521H, S521C, S521V, S521W, S521T, S521K, S521F, S521G, N523W, N523A, N523G, N523S, N523P, N523M, N523Q, N523L, N523K, N523D, N523H, N523F, N523C, I533M, I533V, I533T, I533S, I533F, I533G, I533E, D534E, D534Q, D534L, D534R, D534V, D534C, D534M, D534N, D534A, D534G, D534F, D534T, D534H, D534K, D534S, F576L, F576K, F576V, F576D, F576W, F576M, F576C, F576R, F576Q, F576A, F576Y, F576N, F576G, F576I, F576E, K577L, K577G, K577D, K577R, K577H, K577Y, K577I, K577E, K577V, K577N, I582V, I582K, I582R, I582M, I582G, I582N, I582E, I582A, I582Q, Y583L, Y583C, Y583F, Y583D, Y583Q, L587F, L587D, L587R, L587I, L587P, L587N, L587E, L587S, L587Y, L587M, L587Q, L587G, L587W, L587K or L587T.

Another exemplary piggyBac-like transposon for modifying the genome of a cell is a *Bombyx* transposon which comprises an ITR with the sequence of SEQ ID NO:80, a heterologous nucleic acid to be transposed and a second ITR with the sequence of SEQ ID NO:81. The transposon may further be flanked by a copy of the tetranucleotide 5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:82 on one side of the heterologous nucleic acid, preferably the left side, and a sequence immediately adjacent to the ITR and proximal to the heterologous nucleic acid that is at least 95% or 100% identical to SEQ ID NO:83 on the other side of the heterologous nucleic acid, preferably the right side. This transposon may be transposed by a corresponding *Bombyx* transposase comprising a sequence at least 90% or 100% identical to SEQ ID NO:84, for example. any of SEQ ID NOS:84-106. Preferably the transposase is a hyperactive variant of a naturally occurring transposase of SEQ ID NO:84 including one or more of the following mutations: Q92A, Q92P, Q92N, Q92I, Q92Y, Q92H, Q92F, Q92R, Q92D, Q92M, Q92W, Q92C, Q92G, Q92L, Q92V, Q92T, V93P, V93K, V93M, V93F, V93W, V93L, V93A, V93I, V93Q, P96A, P96T, P96M, P96R, P96G, P96V, P96E, P96Q, P96C, F97Q, F97K, F97H, F97T, F97C, F97W, F97V, F97E, F97P, F97D, F97A, F97R, F97G, F97N, F97Y, H165E, H165G, H165Q, H165T, H165M, H165V, H165L, H165C, H165N, H165D, H165K, H165W, H165A, E178S, E178H, E178Y, E178F, E178C, E178A, E178Q, E178G, E178V, E178D, E178L, E178P, E178W, C189D, C189Y, C189I, C189W, C189T, C189K, C189M, C189F, C189P, C189Q, C189V, A196G, L200I, L200F, L200C, L200M, L200Y, A201Q, A201L, A201M, L203V, L203D, L203G, L203E, L203C, L203T, L203M, L203A, L203Y, N207G, N207A, L211G, L211M, L211C, L211T, L211V, L211A, W215Y, T217V, T217A, T217I, T217P, T217C, T217Q, T217M, T217F, T217D, T217K, G219S, G219A, G219C, G219H, G219Q, Q235C, Q235N, Q235H, Q235G, Q235W, Q235Y, Q235A, Q235T, Q235E, Q235M, Q235F, Q238C, Q238M, Q238H, Q238V, Q238L, Q238T, Q238I, R242Q, K246I, K253V, M258V, F261L, S263K, C271S, N303C, N303R, N303G, N303A, N303D, N303S, N303H, N303E, N303R, N303K, N303L, N303Q, I312F, I312C, I312A, I312L, I312T, I312V, I312G, I312M, F321H, F321R, F321N, F321Y, F321W, F321D, F321G, F321E, F321M, F321K, F321A, F321Q, V323I, V323L, V323T, V323M, V323A, V324N, V324A, V324C, V324I, V324L, V324T, V324K, V324Y, V324H, V324F, V324S, V324Q, V324M, V324G, A330K, A330V, A330P, A330S, A330C, A330T, A330L, Q333P, Q333T, Q333M, Q333H, Q333S, P337W, P337E, P337H, P337I, P337A, P337M, P337N, P337D, P337K, P337Q, P337G, P337S, P337C, P337L, P337V, F368Y, L373C, L373V, L373I, L373S, L373T, V389I, V389M, V389T, V389L, V389A, R394H, R394K, R394T, R394P, R394M, R394A, Q395F, Q395E, Q395C, Q395V, Q395A, Q395H, Q395S, Q395Y, S399N, S399E, S399K, S399H, S399D, S399Y, S399G, S399Q, S399R, S399T, S399A, S399V, S399M, R402Y, R402K, R402D, R402F, R402G, R402N, R402E, R402M, R402S, R402Q, R402T, R402C, R402L, R402V, T403W, T403A, T403V, T403F, T403L, T403Y, T403N, T403G, T403C, T403I, T403S, T403M, T403Q, T403K, T403E, D404I, D404S, D404E, D404N, D404H, D404C, D404M, D404G, D404A, D404Q, D404L, D404P, D404V, D404W, D404F, N408F, N408I, N408A, N408E, N408M, N408S, N408D, N408Y, N408H, N408C, N408Q, N408V, N408W, N408L, N408P, N408K, S409H, S409Y, S409N, S409I, S409D, S409F, S409T, S409C, S409Q, N441F, N441R, N441M, N441G, N441C, N441D, N441L, N441A, N441V, N441W, G448W, G448Y, G448H, G448C, G448T, G448V, G448N, G448Q, E449A, E449P, E449T, E449L, E449H, E449G, E449C, E449I, V469T, V469A, V469H, V469C, V469L, L472K, L472Q, L472M, C473G, C473Q, C473T, C473I, C473M, R484H, R484K, T507R, T507D, T507S, T507G, T507K, T507I, T507M, T507E, T507C, T507L, T507V, G523Q, G523T, G523A, G523M, G523S, G523C, G523I, G523L, I527M, I527V, Y528N, Y528W, Y528M, Y528Q, Y528K, Y528V, Y528I, Y528G, Y528D, Y528A, Y528E, Y528R, Y543C, Y543W, Y543I, Y543M, Y543Q, Y543A, Y543R, Y543H, E549K, E549C, E549I, E549Q, E549A, E549H, E549C, E549M, E549S, E549F, E549L, K550R, K550M, K550Q, S556G, S556V, S556I, P557W, P557T, P557S, P557A, P557Q, P557K, P557D, P557G, P557N, P557L, P557V, H559K, H559S, H559C, H559I, H559W, V560F, V560P, V560I, V560H, V560Y, V560K, N561P, N561Q, N561G, N561A, V562Y, V562I, V562S, V562M, V567I, V567H, V567N, S583M, E601V, E601F, E601Q, E601W, E605R, E605W, E605K, E605M, E605P, E605Y, E605C, E605H, E605A, E605Q, E605S, E605V, E605I, E605G, D607V, D607Y, D607C, D607N, D607W, D607T, D607A, D607H, D607Q, D607E, D607L, D607K, D607G, S609R, S609W, S609H, S609V, S609Q, S609G, S609T, S609K, S609N, S609Y, L610T, L610I, L610K, L610G, L610A, L610W, L610D, L610Q, L610S, L610F or L610N.

Another exemplary piggyBac-like transposon for modifying the genome of a cell is a piggyBat transposon which comprises an ITR with the sequence of SEQ ID NO:107, a heterologous nucleic acid to be transposed and a second ITR with the sequence of SEQ ID NO:108. The transposon may further be flanked by a copy of the tetranucleotide5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:109 on one side of the heterologous nucleic acid, preferably the left side, and a sequence immediately adjacent to the ITR and proximal to the heterologous nucleic acid that is at least 95% or 100% identical to SEQ ID NO:110 on the other side of the heterologous nucleic acid, preferably the right side. This transposon may be transposed by a corresponding piggyBat transposase comprising a sequence at least 90% or 100% identical to SEQ ID NO:111. Preferably the transposase is a hyperactive variant of a naturally occurring transposase. Preferably the hyperactive variant transposase comprises one or more of the following amino acid changes, relative to the sequence of SEQ ID NO:111: A14V, D475G, P491Q, A561T, T546T, T300A, T294A, A520T, G239S, S5P, S8F, S54N, D9N, D9G, I345V. M481V, EI1G, K130T, G9G, R427H, S8P, S36G, D1OG, S36G.

Another exemplary piggyBac-like transposon for modifying the genome of a cell comprises an ITR with the sequence of SEQ ID NO:112, a heterologous nucleic acid to be transposed and a second ITR with the sequence of SEQ ID NO:113. The transposon may further be flanked by a copy of the tetranucleotide5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:114 on one side of the heterologous nucleic acid, preferably the left side, and a sequence immediately adjacent to the ITR and proximal to the heterologous nucleic acid that is at least 95% or 100% identical to SEQ ID NO:115 on the other side of the heterologous nucleic acid preferably the right side. This transposon may be transposed by a corresponding piggyBac transposase comprising a sequence at least 90% or 100% identical to SEQ ID NO:116. Preferably the transposase is a hyperactive variant of a naturally occurring transposase. Preferably the hyperactive variant transposase comprises one or more of the following amino acid changes, relative to the sequence of SEQ ID NO:116: G2C, Q40R, I30V, G1655, T43A, S61R, S103P, S103T, M194V, R281G, M282V, G316E, I426V, Q497L, N505D, Q573L, S509G, N570S, N538K, Q591P, Q591R, F594L, M194V, I30V, S103P, G165S, M282V, S509G, N538K, N571S, C41T, A1424G, C1472A, G1681A, T150C, A351G, A279G, T1638C, A898G, A880G, G1558A, A687G, G715A, T13C, C23T, G161A, G25A, T1050C, A1356G, A26G, A1033G, A1441G, A32G, A389C, A32G, A389C, A32G, T1572A, G456A, T1641C, TI 155C, G1280A, T22C, A106G, A29G, C137T, A14V, D475G, P491Q, A561T, T546T, T300A, T294A, A520T, G239S, SSP, SBF, S54N, D9N, D9G, I345V, M481V, EI1G, K130T, G9G, R427H, S8P, S36G, DI0G, S36G, A51T, C153A, C277T, G201A, G202A, T236A, A103T, A104C, T140C, G138T, T118A, C74T, A179C, S3N, I30V, A46S, A46T, I82W, S103P, R119P, C125A, C125L, G165S, Y177K, Y177H, F180L, F180I, F180V, M185L, A187G, F200W, V207P, V209F, M226F, L235R, V240K, F241L, P243K, N258S, M282Q, L296W, L296Y, L296F, M298V, M298A, M298L, P311V, P311I, R315K, T319G, Y327R, Y328V, C340G, C340L, D421H, V436I, M456Y, L470F, S486K, M503I, M503L, V552K, A570T, Q591P, Q591R, R65A, R65E, R95A, R95E, R97A, R97E, R135A, R135E, R161A, R161E, R192A, R192E, R208A, R208E, K176A, K176E, K195A, K195E, S171E, M14V, D270N, 130V, G165S, M282L, M282I, M282V or M282A.

Another example of a piggyBac-like transposon for modifying the genome of a cell is an *Amyelois* transposon comprising an ITR with the sequence of SEQ ID NO:117, a heterologous nucleic acid, and a second ITR with the sequence of SEQ ID NO:118. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:119 on one side of the heterologous nucleic acid, and a sequence that is at least 95% or 100%identical to SEQ ID NO:120 on the other side of the heterologous nucleic acid. This transposon may be transposed by a corresponding *Amyelois* transposase comprising a sequence at least 90% identical to SEQ ID NO:121. Preferably the transposase is a hyperactive variant of a naturally occurring transposase. Preferably the hyperactive variant transposase comprises one or more of the following amino acid changes, relative to the sequence of SEQ ID NO:121: P65E, P65D, R95S, R95T, V100I, V100L, V100M, L115D, L115E, E116P, H121Q, H121N, K139E, K139D, T159N, T159Q, V166F, V166Y, V166W, G179N, G179Q, W187F, W187Y, P198R, P198K, L203R, L203K, I209L, 1209V, 1209M, N211R, N211K, E238D, T273I, L273V, L273M, D304K, D304R, I323L, I323M, I323V, Q329G, Q329R, Q329K, T345L, T345I, T345V, T345M, K362R, T366R, T366K, T380S, L408M, L408I, L408V, E413S, E413T, S416E, S416D, I426M, I426L, I426V, S435G, L458M, L458I, L458V, A472S, A472T, V475I, V475L, V475M, N483K, N483R, I491M, I491V, I491L, A529P, K540R, S560K, S560R, T562K, T562R, S563K, S563R.

Another exemplary piggyBac-like transposon for modifying the genome of a cell is a *Heliothis* transposon comprising an ITR with the sequence of SEQ ID NO:122, a heterologous nucleic acid and a second ITR with the sequence of SEQ ID NO:123. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:124 on one side of the heterologous nucleic acid, and a sequence that is at least 95% or 100% identical to SEQ ID NO: 125 on the other side of the heterologous nucleic acid. This transposon may be transposed by a corresponding *Heliothis* transposase comprising a sequence at least 90% or 100% identical to SEQ ID NO:126. Preferably the transposase is a hyperactive variant of a naturally occurring transposase. Preferably the hyperactive variant transposase comprises one or more of the following amino acid changes, relative to the sequence of SEQ ID NO:126: S41V, 54II, S41L, L43S, L43T, V81E, V81D, D83S, D83T, V85L, V85I, V85M, P125S, P125T, Q126S, Q126T, Q131H, Q131K, Q131T, Q131S, S136V, S136I, S136L, S136M, E140C, E140A, N151Q, K169E, K169D, N212S, I239L, I239V, I239M, H241N, H241Q, T268D, T268E, T297C, M300R, M300K, M305N, M305Q, L312I, C316A, C316M, L321V, L321M, N322T, N322S, P351G, H357R, H357K, H357D, H357E, K360Q, K360N, E379P, K397S, K397T, Y421F, Y421W, V450I, V450L, V450M, Y495F, Y495W, A447N, A447D, A449S, A449V, K476L, V492A, I500M, L585K and T595K.

An advantageous piggyBac-like transposon for modifying the genome of a cultured mammalian cell is an *Oryzias* transposon comprising an ITR with the sequence of SEQ ID NO:127, a heterologous nucleic acid and a second ITR with the sequence of SEQ ID NO:128. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:129 on one side of the heterologous nucleic acid, and a sequence that is at least 95% or 100% identical to SEQ ID NO:130 on the other side of the heterologous nucleic acid. This transposon may be transposed by a corresponding *Oryzias* transposase comprising a sequence at least 90% or 100% identical to SEQ ID NO:131. Preferably the transposase is a hyperactive variant of a naturally occurring transposase. Preferably the hyperactive variant transposase comprises one or more of the following amino acid changes, relative to the sequence of SEQ ID NO:131: E22D, A124C, Q131D, Q131E, L138V, L138I, L138M, D160E, Y164F, Y164W, I167L, I167V, I167M, T202R, T202K, I206L, I206V, I206M, I210L, I210V, I210M, N214D, N214E, V253I, V253L, V253M, V258L, V258I, V258M, A284L, A284I, A284M, A284V, V386I, V386M, V386L, M400L, M400I, M400V, S408E, S408D, L409I, L409V, L409M, V458L, V458M, V458I, V467I, V467M, V467L, L468I, L468V, L468M, A514R, A514K, V515I, V515M, V515L, R548K, D549K, D549R, D550R, D550K, S551K and S551R Another exemplary piggyBac-like transposon for modifying the genome of a cell is an *Agrotis* transposon comprising an ITR with the sequence of SEQ ID NO:132, a heterologous nucleic acid, and a second ITR with the sequence of SEQ ID NO:133. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:134 on one side of the heterologous nucleic acid, and a sequence that is at least 95% or 100% identical to SEQ ID NO:135 on the other side of the heterologous nucleic acid. This transposon may be transposed by a corresponding *Agrotis* transposase comprising a sequence at least 90% or 100% identical to SEQ ID NO:136. Preferably the transposase is a hyperactive variant of a naturally occurring transposase.

Another piggyBac-like transposon for modifying the genome of a cell is a *Helicoverpa* transposon comprising an ITR with the sequence of SEQ ID NO:137, a heterologous nucleic acid and a second ITR with the sequence of SEQ ID NO:138. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:139 on one side of the heterologous nucleic acid, and a sequence that is at least 95% or 100% identical to SEQ ID NO:140 on the other side of the heterologous nucleic acid. This transposon may be transposed by a corresponding *Helicoverpa* transposase comprising a sequence at least 90% or 100% identical to SEQ ID NO:141. Preferably the transposase is a hyperactive variant of a naturally occurring transposase.

Another exemplary transposon for modifying the genome of cell is a Sleeping Beauty transposon from the Mariner family of transposons, for example one that comprises an ITR with the sequence of SEQ ID NO:142, a heterologous nucleic acid and a second ITR with the sequence of SEQ ID NO:143. Such a transposon can comprise a first transposon end with at least 90% or 100% sequence identity to SEQ ID NO:144, and a second transposon end with at least 90% or 100% sequence identity to SEQ ID NO:145. This transposon may be transposed by a corresponding Sleeping Beauty transposase comprising a sequence at least 90% or 100% identical to SEQ ID NO:146, including hyperactive variants thereof.

Another example transposon for modifying the genome of a mammalian cell is a TcBuster transposon, from the hAT family of transposons, for example one that comprises an ITR with the sequence of SEQ ID NO:147, a heterologous nucleic acid and a second ITR with the sequence of SEQ ID NO:148. Such a transposon can comprise a first transposon end with at least 90% or 100% sequence identity to SEQ ID NO:149, and a second transposon end with at least 90% or 100% sequence identity to SEQ ID NO:150. This transposon may be transposed by a corresponding TcBuster transposase comprising a sequence at least 90% or 100% identical to SEQ ID NO:151, including hyperactive variants thereof.

VII. Cells and Transgenic Animals

Nucleic acids comprising one or more transcriptional units as further described herein and gene transfer systems including the nucleic acids can be introduced into various cells and transgenic non-human animals. Cells into which nucleic acids are introduced are sometimes referred to as host cells or target cells or target host cells. Cells can be prokaryotic or eukaryotic. Mammalian cells, such as human, primate, or rodent are preferred. Insect cells can also be used. Cells can be a cell line of substantially identical cells obtained by expansion of a single cell or a mixed population of cells. Cells can be an immortal cell line or cells of finite life span. Some exemplary cell lines include CHO cell lines, various COS cell lines, HeLa cells, COS cells, 293 cells, U20S, HEK293 cells, L cells, and non-antibody-producing myelomas including Sp2/0 and NS0. Examples of cell types include hepatocytes, neural cells, muscle cells, blood cells, lymphocytes (B cells, natural killer cells and T cells), embryonic stem cells, somatic stem cells, hematopoietic cells, embryos, zygotes and sperm cells (some of which are open to be manipulated in an in vitro setting). Cells can be totipotent (i.e., a cell whose descendants can become any cell type in an organism, e.g., embryonic stem cells), pluripotent (cells whose descendants can differentiate into several restricted cell types, such as hematopoietic stem cells or other stem cells). Nucleic acid introduced into cells can also be used to generate transgenic nonhuman animals, e.g., rodents, such as mice, rats and rabbits, insects, fish, farm animals, such as goats, sheep, pigs, and cattle and non-human primates. Such transgenic animals typically incorporate an introduced heterologous nucleic acid into the genome of their germline and other cells. Such cells and transgenic animals can be used for production of proteins, e.g., therapeutic proteins or enzymes. Cells and transgenic animals can also be used for analyzing phenotypes conferred by expressed proteins, e.g., disease-associated phenotypes, and screening compounds for activity against such disease. Introduced nucleic acids can also be used to modify expression of genes of cells and transgenic animals, as for example, when the introduced nucleic acid encodes an inhibitor RNA to suppress expression of an endogenous gene. Suitable cells into which a nucleic acid has been introduced, particularly stem cells, can also be used for gene therapy. In some such application, the introduced nucleic acid includes a coding segment under inducible control, such that the coding segment encodes a polypeptide, which when expressed is lethal to the cell. Such a system allows an introduced cell to be eliminated by supplying an inducer of expression should the cell start undergoing inappropriate growth (e.g., becoming cancerous). After introduction of transcriptional units into cells, cells can be cultured and tetracycline or an analog be introduced into the culture medium to turn on or off expression of a coding segment. Likewise animals into which transcriptional units have been introduced can be contacted with tetracycline or an analog when a developmental stage is reached at which induction or suppression of expression of the coding segment on the first transcriptional unit is desired. Contacting can be by any conventional route including intravenous, intraperitoneal, subcutaneous, oral, transdermal, and intramuscular. Nucleic acid encoding one or more transcriptional units as described below can also be used in a coupled in vitro transcription and translation systems kits for which are commercially available from e.g., Thermo Fisher Scientific or New England Biolabs.

VIII. Inducible Systems

The invention provides several systems for placing a coding segment of interest under inducible control depending on the presence or absence of tetracycline, doxycycline or other analog. Such systems typically include two transcriptional units, one for expressing a coding segment of interest, the other for expressing a tet-repressor or modified tet-repressor to make expression of the first transcriptional unit dependent on the presence or absence of tetracycline or an analog thereof.

One expression system has a first transcriptional unit including in operable linkage and in order from 5' to 3', a promoter, one or more tet-operator sites, and a coding segment to be expressed. An exemplary transcriptional unit is shown in FIG. 2, which includes a promoter with a TATA box, and adjacent segment ending at a position upstream from the transcriptional start site, first and second tet-operators separated by a spacer, and a coding segment encoding a 5' UTR and an open reading frame to be expressed. The second tet-operator can be immediately adjacent to the first nucleotide of the 5' UTR as shown. When the first and second tet-operators replace a segment of the promoter immediately upstream from the transcription initiation site, transcription may initiate downstream of the remaining promoter within the first or second tet-operator or the 5' UTR. As shown, the promoter includes DNA between the TATA box and a position upstream of the promoter's normal transcriptional start site (the first transcribed nucleotide). It is preferred that the first tet operator sequence replaces a contiguous segment of the promoter including at least the first base pair upstream of the transcriptional start site. More preferably the first tet operator sequence replaces a contiguous segment of 1, 2, 3, 4, 5, 6, 7, 8, 9, 10, 11, 12, 13, 14 or 15 bp 5' of the promoter starting at the nucleotide immediately upstream of the transcriptional start site. Most preferably the first tet operator sequence replaces at least 6-bp 5' of the promoter starting at the nucleotide immediately upstream of the transcriptional start site. A preferred 5' UTR comprises the *Xenopus* globin UTR (SEQ ID NO:29).

Figure 3:
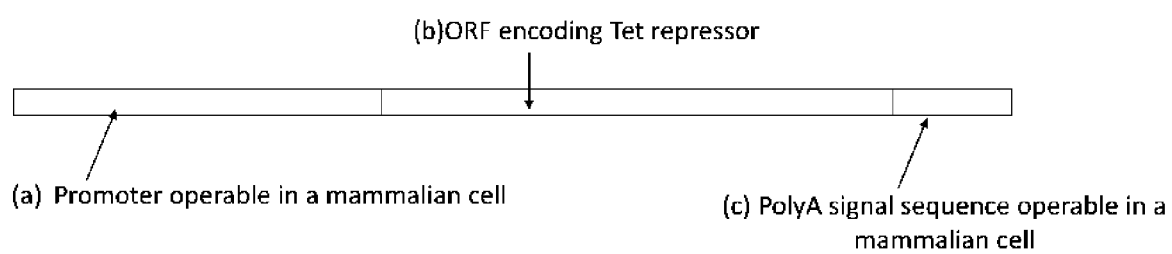

A second transcriptional unit includes a promoter operably linked to a segment encoding a tet-repressor. An exemplary transcriptional unit is shown in FIG. 3. In the system shown a promoter operable in a mammalian cell is operably linked to a coding segment including an open reading frame encoding a tet-repressor followed by a segment encoding a polyA tail. In the absence of tetracycline, doxycycline or other analog, expressed tet-repressor binds to the operator sites in the first transcriptional unit, hindering initiation of transcription and thereby inhibiting or eliminating expression of the coding segment. In the presence of tetracycline, doxycycline or other analog, the tet-repressor binds to the tetracycline or analog, inhibiting or eliminating binding of the tet-repressor to tet-operator(s) in the first transcriptional unit and removing inhibition of the coding segment. Thus, the coding segment is expressed in the presence of tetracycline or analog and not in the absence or at least expression in the presence is much greater than in the absence (e.g., by a factor of at least 2, 5, 10, 20, 50 or 100).

The invention further provides several systems for placing a coding segment of interest under inducible control depending on the presence or absence of cumate or other analog. Such systems typically include two transcriptional units, one for expressing a coding segment of interest, the other for expressing a cumate repressor or modified cumate repressor to make expression of the first transcriptional unit dependent on the presence or absence of cumate or an analog thereof.

Figure 5:
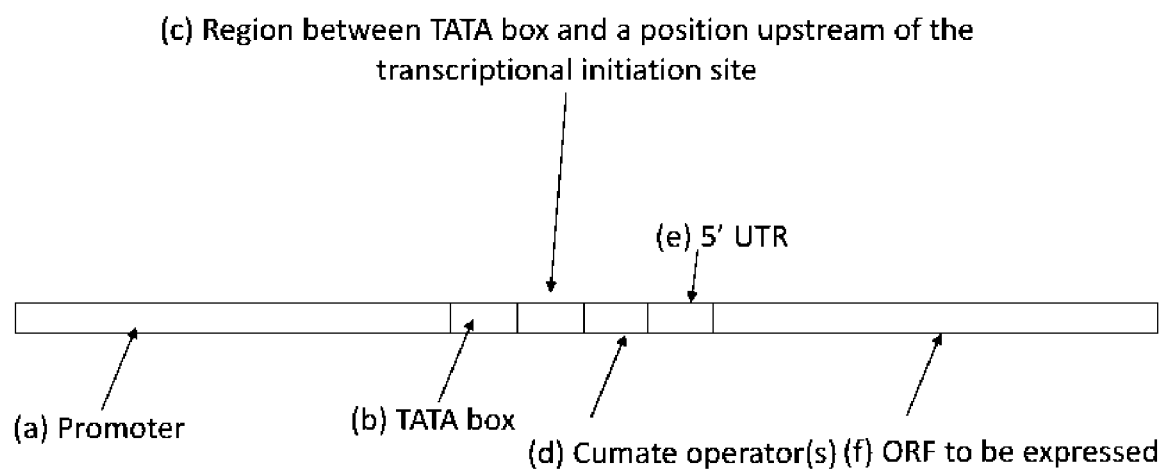
FIGS. 5 and 6 show first and second transcriptional units respectively for a system for cumate-inducible expression of an open reading frame ("cumate-off").

One expression system has a first transcriptional unit including in operable linkage and in order from 5' to 3', a promoter, one or more cumate operators, and a coding segment to be expressed. An exemplary transcriptional unit is shown in FIG. 5, which includes a promoter with a TATA box at least one cumate operator a coding segment encoding a 5' UTR and an open reading frame to be expressed. When the cumate operator(s) replace a segment of the promoter immediately upstream from the transcription initiation site, transcription may initiate downstream of the remaining promoter within the first or second cumate operator or the 5' UTR. Sequence of exemplary promoter-cumate operator fusions are provided as SEQ ID NOS:161-163. A preferred 5' UTR comprises the *Xenopus* globin UTR (SEQ ID NO:29).

Figure 6:
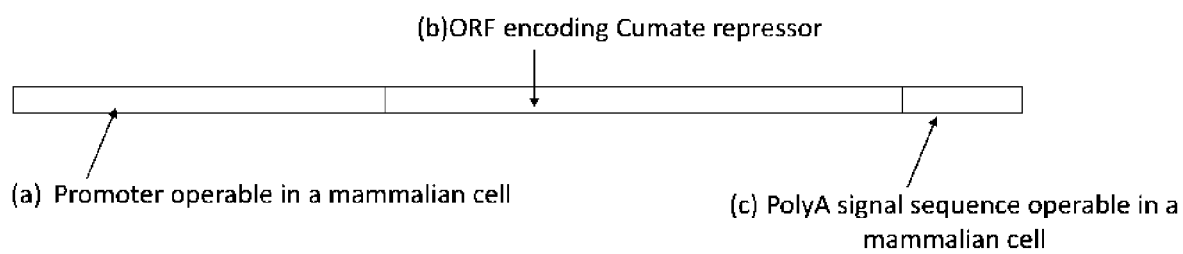

A second transcriptional unit includes a promoter operably linked to a segment encoding a cumate repressor. An exemplary transcriptional unit is shown in FIG. 6. In the system shown a promoter operable in a mammalian cell is operably linked to a coding segment including an open reading frame encoding a cumate repressor followed by a segment encoding a polyA tail. In the absence of cumate or other analog, expressed cumate repressor binds to the operator sites in the first transcriptional unit, hindering initiation of transcription and thereby inhibiting or eliminating expression of the coding segment. In the presence of cumate or analog, the cumate-repressor binds to the cumate or analog, inhibiting or eliminating binding of the cumate repressor to cumate operator(s) in the first transcriptional unit and removing inhibition of the coding segment. Thus, the coding segment is expressed in the presence of cumate or analog and not in the absence or at least expression in the presence is much greater than in the absence (e.g., by a factor of at least 2, 5, 10, 20, 50 or 100).

The promoter of the first transcriptional unit (tet and cumate systems) is preferably a strong promoter to increase expression of the coding sequence after induction. The promoter is preferably a chimeric mouse-human CMV promoter as described above. Such a promoter is a preferred promoter to a human CMV promoter, which has been used for tetracycline-inducible expression previously. This is because elimination of one or more CpG sites from the human CMV promoter reduces the silencing effects of CpG methylation.

The promoter for the second transcriptional unit (tet and cumate systems) is preferably a promoter of reduced strength compared with the chimeric mouse-human CMV promoter described above or even with the human CMV promoter used in some conventional systems. Use of a reduced strength promoter reduces the expression of the tet repressor and thus allows induction of expression from the first transcriptional unit at lower levels of tetracycline or analog than when the same or similar strength promoters are used for both transcriptional units.

The first and second transcriptional units of this system (tet and cumate systems) are preferably combined on the same contiguous nucleic acid for introduction into cells. The nucleic acid can then be part of a transposon or other vector or gene delivery system as described above. Incorporating both transcriptional units on the same nucleic acid facilitates introduction of both units into cells because only one transfection and identification of transformed cells is necessary, but also contributes to cells integrating the same number of copies of each of the transcriptional units. The presence of equal numbers of both transcriptional units allows reproducible control of the ratio of tet-repressor to the number of copies of the first transcriptional unit. This reproducible control, preferably in combination with appropriate promoter selection as described above, can result in any of high levels of inducible expression, greater differentiation between levels of expression in presence and absence of inducer and inducible expression using lower levels of inducer.

Figure 4:
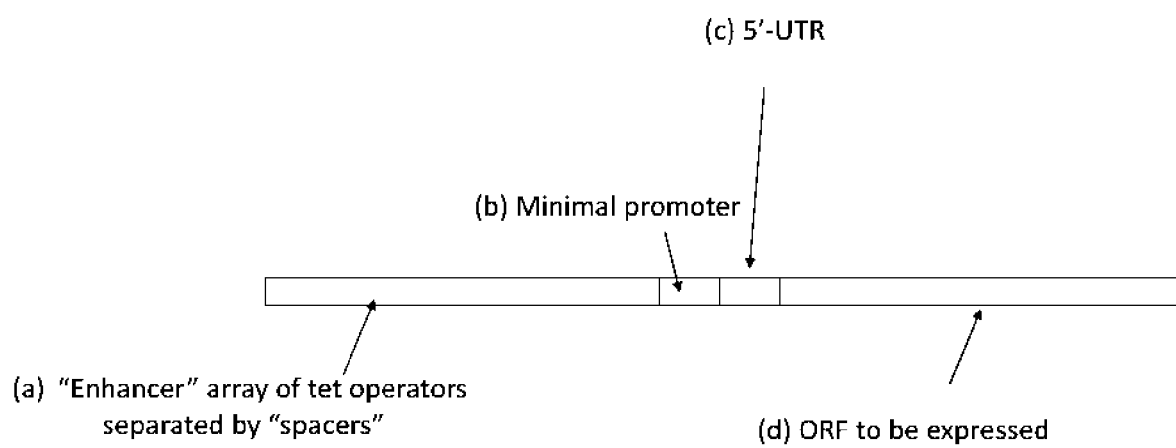
FIG. 4 shows a first transcriptional unit of a different system for tet-inducible expression of an open reading frame ("tet-on"}.

A second tet system for inducible expression has a first transcriptional unit comprising in operable linkage and in order from 5' to 3', one or more tet-operators, a minimal promoter and a coding segment to be expressed. FIG. 4 shows an exemplary form of this transcriptional unit with an array of tet-operators separated by spacers upstream of a minimal promoter, operably linked to a coding segment encoding a 5' UTR and open reading frame to be expressed. The 5' UTR preferably comprises *Xenopus* globin UTR of SEQ ID NO:29. Preferably 2-10 or 3-8, e.g., 2, 3, 4, 5, 6, 7, 9, or 10 operators are present in the array separated by spacers of 10-25 bp, optionally 15-20 bp. A second transcriptional unit includes in operable linkage a promoter and a segment encoding either a tet-repressor or a modified tet-repressor fused to a transcriptional activation domain, such as VP16. When the tet-repressor fused to the transcriptional activation domain is expressed from the second transcriptional unit, it binds to the array of tet-operators in the absence of tetracycline or analog. The transcriptional activation domain recruits polymerase and other transcription factors resulting in transcription from the minimal promoter and expression of the coding segment. In the presence of tetracycline or analog, the tet-repressor can no longer bind the tet-operator array or does so to a much-reduced extent, inhibiting or eliminating expression of the coding segment. Thus, the coding segment is placed under tetracycline or analog inducible control being expressed in the absence of tetracycline or analog.

The reverse form of induction occurs when the tet-repressor is replaced with a modified form of tet-repressor, which binds to tet-operators in the presence of tetracycline or analog. Here, in the absence of tetracycline or analog, the modified tet-repressor linked to transcriptional activation domain is expressed but does not bind significantly if at all to the tet-operators resulting in little or no recruitment of polymerase and other transcription factors, and little if any expression from the minimal promoter. When tetracycline or analog is supplied, the tetracycline or analog binds to the modified tet-repressor, which in turn binds to the tet-operators. The linked transcriptional activation domain then recruits polymerase and other transcriptional factor resulting in transcription of the coding segment from the minimal promoter. The coding segment is thus placed under inducible control of tetracycline or analog, being expressed in the presence of tetracycline and not expressed or expressed at much lower levels in the absence of tetracycline (e.g., least 2-, 5-, 10-, 20-, 50- or 100-fold increased expression on inductions).

Exemplary tet operator arrays can have a nucleotide sequence selected from SEQ ID NOS:8 and 9. An exemplary minimal human CMV promoter has SEQ ID NO:22. Exemplary 5' UTRs comprising the *Xenopus* globin 5' UTR can have a nucleotide sequence selected from SEQ ID NOS:29, 30 and 31. The exemplary arrays are linked in the order from 5' to 3': tet operator array, minimal human CMV promoter, 5' UTR. Any of the exemplified tet operator arrays, can be used with any exemplified minimal human CMV promoter, and any exemplified 5' UTR in the order specified. An exemplary tet operator array fused to the 5' end of a chimpanzee minimal CMV promoter has a nucleotide sequence SEQ ID NO:26. Preferably the 3' end of the minimal chimpanzee CMV promoter is joined to a 5' UTR comprising the *Xenopus* globin 5' UTR with nucleotide sequence SEQ ID NO:29. An exemplary sequence comprising the minimal chimpanzee CMV promoter joined to a 5' UTR comprising the *Xenopus* globin 5' UTR has nucleotide sequence SEQ ID NO:25. An exemplary sequence comprising a tet operator array fused to the minimal chimpanzee CMV promoter joined to a 5' UTR comprising the *Xenopus* globin 5' UTR has nucleotide sequence SEQ ID NO:27.

Figure 7:
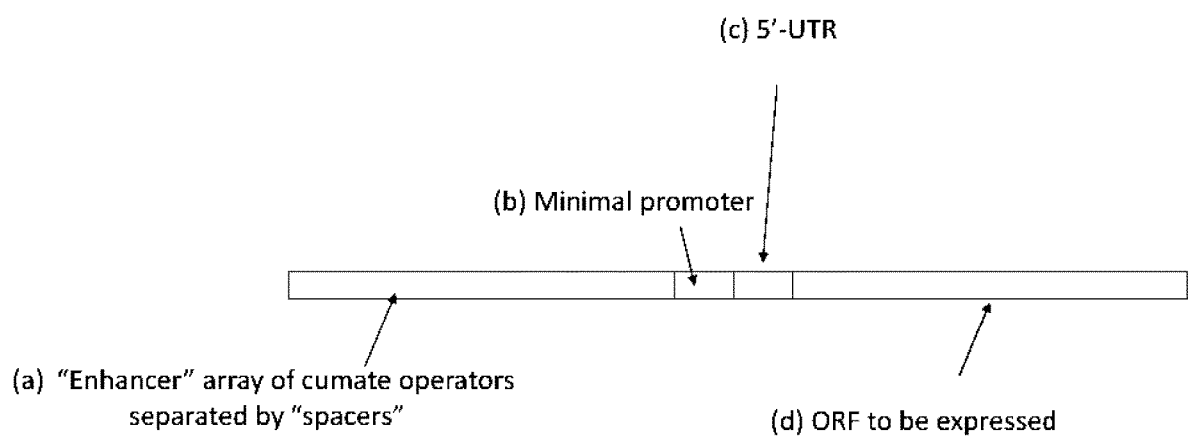
FIG. 7 shows a first transcriptional unit of a different system for cumate-inducible expression of an open reading frame ("cumate on").

A second cumate system for inducible expression has a first transcriptional unit comprising in operable linkage and in order from 5' to 3', one or more cumate-operators, a minimal promoter and a coding segment to be expressed. FIG. 7_shows an exemplary form of this transcriptional unit with an array of cumate operators separated by spacers upstream of a minimal promoter, operably linked to a coding segment encoding a 5' UTR and open reading frame to be expressed. The 5' UTR preferably comprises *Xenopus* globin UTR of SEQ ID NO:29. Preferably 2-10 or 3-8, e.g., 2, 3, 4, 5, 6, 7, 9, or 10 operators are present in the array, optionally separated by spacers of 1-25 bp. A second transcriptional unit includes in operable linkage a promoter and a segment encoding either a cumate repressor or a modified cumate repressor fused to a transcriptional activation domain, such as VP16. When the cumate repressor fused to the transcriptional activation domain is expressed from the second transcriptional unit, it binds to the array of cumate operators in the absence of cumate or analog. The transcriptional activation domain recruits polymerase and other transcription factors resulting in transcription from the minimal promoter and expression of the coding segment. In the presence of cumate or analog, the cumate repressor can no longer bind the cumate operator array or does so to a much-reduced extent, inhibiting or eliminating expression of the coding segment. Thus, the coding segment is placed under cumate or analog inducible control being expressed in the absence of cumate or analog.

The reverse form of induction occurs when the cumate repressor is replaced with a modified form of cumate repressor, which binds to cumate-operators in the presence of cumate or analog. Here, in the absence of cumate or analog, the modified cumate repressor linked to transcriptional activation domain is expressed but does not bind significantly if at all to the cumate operators resulting in little or no recruitment of polymerase and other transcription factors, and little if any expression from the minimal promoter. When cumate or analog is supplied, the cumate or analog binds to the modified cumate repressor, which in turn binds to the cumate operators. The linked transcriptional activation domain then recruits polymerase and other transcriptional factor resulting in transcription of the coding segment from the minimal promoter. The coding segment is thus placed under inducible control of cumate or analog, being expressed in the presence of cumate and not expressed or expressed at much lower levels in the absence of cumate (e.g., least 2-, 5-, 10-, 20-, 50- or 100-fold increased expression on inductions).

Exemplary cumate operator array-promoter fusions are SEQ ID NOS:164-166. Exemplary cumate operator promoter fusions including a 5' UTR are SEQ ID NOS:167-169.

Again (tet and cumate systems), selection of promoters for the first and second transcriptional units and combination of the units into the same contiguous molecule can improve the efficiency and reproducibility of inducible control. As already mentioned, the promoter for the first transcriptional unit is a minimal promoter. A preferred promoter is the minimal chimp CMV promoter described above, which results in higher level expression of a coding segment in the present systems than a minimal human CMV promoter used in conventional systems. The minimal chimp promoter, when activated by binding of a transcriptional activation domain as described above, is more active than a minimal human CMV promoter used in conventional tetracycline-inducible vectors. Preferred promoters for the second transcriptional unit are the intermediate strength promoters described above, although other promoters can also be used. Again, incorporation of both transcriptional units on the same nucleic acid for introduction into cells is advantageous for obtaining a cell that has integrated both transcription units and coordinating expression of the second transcriptional unit with the number of copies of the first transcriptional unit to be regulated. This reproducible control preferably in combination with appropriate promoter selection as described above can result in any of high levels of inducible expression, greater differentiation between levels of expression in presence and absence of inducer and inducible expression using lower levels of inducer.

IX EXAMPLES

1. Inducible Promoters Comprising Tet Binding Sites Between the Promoter and Transcription Start Site in Transiently Transfected HEK Cells We tested several embodiments of tet-inducible promoters for their ability to respond to increasing concentrations of doxycycline after transient transfection into (human) HEK 293 cells. Two promoters were constructed in which the 12 bp to the 5' of the transcriptional start site were removed and replaced by a pair of tet operators with nucleotide sequence SEQ ID NO:2. The first promoter was constructed by modification of the human CMV promoter with nucleotide sequence SEQ ID NO:14. Removal of the 12 bp to the 5' of the transcriptional start site produced nucleotide sequence SEQ ID NO:36. Addition of 2x tet operators to this truncated promoter produced nucleotide sequence SEQ ID NO:15. The second promoter constructed by modification of a chimeric murine-human CMV promoter comprising the first 161 bp of the murine CMV promoter with nucleotide sequence SEQ ID NO:16 fused to the last 127 bp of the human CMV promoter with nucleotide sequence SEQ ID NO:13: the junction between the two promoters comprised a 12 bp sequence common to both: 5'-ACGTCAATGGGA-3', and the sequence of the resulting chimeric promoter had nucleotide sequence SEQ ID NO:12. Removal of the 12 bp to the 5' of the transcriptional start site produced nucleotide sequence SEQ ID NO:10. Addition of 2x tet operators to this truncated promoter produced nucleotide sequence SEQ ID NO:11.

The 3' end of the second tet operator in each of the two promoters described above, was fused to a 5' UTR with nucleotide sequence SEQ ID NO:31, which comprised a Xenopus globin 5'UTR modified to include a Kozak sequence (the modified Xenopus globin 5'UTR has nucleotide sequence SEQ ID NO:29). The UTR was fused to an open reading frame encoding Dasher GFP with amino acid sequence of SEQ ID NO:32, such that transcription from the promoter would result in expression of the GFP.

Each of the two different tet-inducible promoter-GFP transcriptional units was cloned onto a plasmid comprising a second transcriptional unit. The second transcriptional unit comprised an open reading frame encoding a tet repressor with amino acid sequence of SEQ ID NO:5. The open reading frame encoding the repressor was linked to a promoter operable in mammalian cells. Promoters selected were a PGK promoter with nucleotide sequence SEQ ID NO:18, an EEF2 promoter with nucleotide sequence SEQ ID NO:17, a murine CMV promoter with nucleotide sequence SEQ ID NO:16, and a human CMV promoter with nucleotide sequence SEQ ID NO:13.

HEK293 suspension cells were grown in flasks in Expi293 media at 37° C. with 8% CO2, in an incubator with 25 mm throw at 125 RPM. The cells were passaged at a density of 2.5×106 cells/ml 24 hours prior to transfection. Cells were diluted to 3×106 cells/ml, and 700 ul were aliquoted into 96 deep well plates. Each DNA construct was transfected three independent times using ExpiFectamine™ 293 Transfection Reagent at a 1:2.7 DNA:Transfection reagent ratio. After transfection, the cells were placed in an incubator at 3° C. with 8% CO2, with a 3 mm throw shaking at 1,000 RPM. 24 hours post-transfection, the cultures were fed with ExpiFectamine™ 293 Transfection Enhancer 1 and ExpiFectamine™ 293 Transfection Enhancer 2. After this feeding, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 1.

Row 6 of Table 1 shows the behavior of a construct in which the human CMV promoter was modified by addition of tet operators to serve as the inducible promoter, and where the human CMV promoter was also used as the promoter from which the tet repressor was transcribed. Expression from this construct was induced only at the highest concentration of doxycycline tested (100 ng/ml). Similar performance was observed when the human-murine chimeric CMV promoter was modified by addition of tet operators to serve as the inducible promoter, and where the murine CMV promoter was also used as the promoter from which the tet repressor was transcribed (Table 1 row 5), except that the maximum inducible expression was about twice as high as obtained using the human CMV promoter. When weaker promoters EEF2 or PGK were used to drive expression of the tet repressor, induction of expression was seen at lower levels of doxycycline (rows 4 and 3 respectively). This shows that the threshold for doxycycline induction of expression can be modulated by choice of promoter used to express the tet repressor: weaker promoters express lower levels of tet repressor, so less doxycycline is required to bind to the tet repressor to prevent repressor binding to the operators and remove the block to transcriptional initiation.

2. Inducible Promoters Comprising Tet Binding Sites Between the Promoter and Transcription Start Site in Transiently Transfected CHO-S Cells We tested several embodiments of tet-inducible promoters for their ability to respond to increasing concentrations of doxycycline after transient transfection into CHO cells. The same DNA constructs were used as described in Example 1. CHO-s cells were grown in flasks in ExpiCHO media at 37° C. with 5% CO2, in an incubator with 25 mm throw at 125 RPM. The cells were passaged at a density of 4.5×106 cells/ml 24 hours prior to transfection. Cells were diluted to 6×106 cells/ml, and 800 ul were aliquoted into 96 deep well plates. Each DNA construct was transfected three independent times using ExpiFectamine™ CHO Transfection Reagent at a 1:4 DNA:Transfection reagent ratio. After transfection, the cells were placed in an incubator at 37° C. with 5% CO2, with a 3 mm throw shaking at 1,000 RPM. 24 hours post-transfection, the cultures were fed with Expi-Fectamine™ CHO Enhancer and ExpiCHO Feed. After feeding the cells, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 2.

Table 2 shows a similar pattern to inducible expression in transient HEK cells, except that the human and murine CMV constructs shown in rows 5 and 6 have reversed places. Expression from the construct in which the murine CMV promoter was used as the promoter from which the tet repressor was transcribed (Table 2 row 5) was induced only at the higher concentrations of doxycycline tested (a little at 30 ng/ml, more at 100 ng/ml). In contrast, higher expression at lower doxycycline concentrations was observed when the human CMV promoter was used as the promoter from which the tet repressor was transcribed (Table 2 row 6). This is consistent with the murine CMV promoter being stronger than the human CMV promoter in rodent cells and the human CMV promoter being stronger than the murine CMV promoter human cells. Again, when weaker promoters EEF2 or PGK were used to drive expression of the tet repressor, induction of expression was seen at lower levels of doxycycline (rows 4 and 3 respectively). Inducible expression was higher from the chimeric human murine CMV promoter than from the human CMV promoter. Again the threshold for doxycycline induction of expression can be modulated by choice of promoter used to express the tet repressor: weaker promoters express lower levels of tet repressor, so less doxycycline is required to bind to the tet repressor to prevent repressor binding to the operators and remove the block to transcriptional initiation.

3. Inducible Promoters Comprising Tet Binding Sites Between the Promoter and Transcription Start Site in Stably Transfected CHO-K1 Cells We tested several embodiments of tet-inducible promoters for their ability to respond to increasing concentrations of doxycycline when stably integrated into CHO-K1 cells. DNA constructs were used as described in Example 1. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA3' target integration sequence, immediately followed by a first ITR with nucleotide sequence SEQ ID NO:41 immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ ml, and 800 ul were aliquoted into 96 deep well plates. Cultures were induced by the addition doxycycline at either 10, 30, 100, 300, 1000 or 3000 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 3.

Table 3 shows a similar pattern to inducible expression in transiently transfected CHO cells, except that the overall induction levels were substantially lower. Lowest inducible expression was seen where the tet repressor was transcribed from the very active human or murine CMV promoters (Table 3 rows 5 and 6). The constructs in which tet repressor was transcribed from the more weakly active promoters showed expression that was induced at lower levels of doxycycline (expression started at 30 ng/ml when the tet repressor was transcribed from EEF2 or PGK promoters, while 300 ng/ml doxycycline) and reached 1.7-fold higher levels at high concentrations of doxycycline than constructs where the tet repressor was transcribed from a CMV promoter.

4. Inducible Promoters Comprising Tet Binding Sites Between the Promoter and Transcription Start Site in Stably Transfected CHO-K1 Cells We tested several embodiments of tet-inducible promoters for their ability to respond to increasing concentrations of doxycycline when stably integrated into CHO-K1 cells. DNA transposon constructs were similar to those described in Example 3, except that additional versions were made with other promoters driving expression of the tet repressor. Transposon compositions are indicated in Table 4.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures of each stably selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30, 100, 300 or 1000 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 4.

Table 4 shows a similar pattern to the inducible expression in stably transfected CHO cells shown in Table 3. Most notably, two constructs whose inducible expression is shown in Table 4 differed only in the 6 nucleotides preceding the tet repressor open reading frame (Table 4 rows 6 and 7). The construct shown in row 6 had an optimal Kozak sequence (5'-GCCGCCACC-3'), while the construct shown in row 7 had a de-optimized Kozak (5'-GCCTTTTTT-3'). The de-optimized Kozak results in reduced translational initiation and thus in less tet repressor being present. The consequence of this was that this inducible promoter was induced at only 10 ng/ml doxycycline, and was fully induced at 30 ng/ml doxycycline, whereas the otherwise identical construct with the optimal Kozak initiating translation of the tet repressor did not begin induction until 100 ng/ml doxycycline, and only became fully induced by 1,000 ng/ml doxycycline.

Tables 1, 2, 3 and 4 show that expression levels obtained from tet-inducible promoters, and the amount of inducer required to induce expression, differ depending on the level of expression of the tet repressor. The benefit of combining the transcriptional unit expressing the tet repressor onto the same transposon as the inducible transcriptional unit, is that it minimizes the potential variation in relative expression of tet repressor compared with the number of copies of the inducible promoter in the cell. This improves the predictability of the performance of the system.

5. Inducible Promoters Comprising Tet Binding Sites 5' of the Promoter in Transiently Transfected HEK 293 Cells We tested several embodiments of tet-inducible promoters for their ability to respond to increasing concentrations of doxycycline after transient transfection into HEK 293 cells.

Three different minimal CMV promoters, from human, mouse and chimpanzee CMV (with nucleotide sequences SEQ ID NO:22, 23 and 24 respectively) were each fused, at their 5' ends, to an array of 8 tet operators with nucleotide sequence SEQ ID NO:3, to create 3 tet-inducible promoters. The 3' end of each minimal promoter was fused to a 5'UTR with nucleotide sequence SEQ ID NO:30. A control inducible promoter was also constructed by fusing a previously described array of 7 tet operators with nucleotide sequence SEQ ID NO:4 to the 5' end of a previously described modified minimal human CMV promoter with nucleotide sequence SEQ ID NO:38. The 3' end of this control minimal promoter was fused to a 5'UTR with nucleotide sequence SEQ ID NO:39. The 3' end of each 5'UTR was fused to an open reading frame encoding Dasher GFP with amino acid sequence SEQ ID NO:32.

Each of the different tet-inducible promoter-GFP transcriptional units was cloned onto a plasmid comprising a second transcriptional unit. The second transcriptional unit comprised an open reading frame encoding a transcriptional activator comprising a modified tet repressor with amino acid sequence of SEQ ID NO:6, fused to a VP16 transcriptional activator with amino acid sequence SEQ ID NO:7. In addition the control tet-inducible promoter GFP transcriptional unit was cloned onto a plasmid comprising a second transcriptional unit comprising an open reading frame encoding a transcriptional activator comprising a modified tet repressor with amino acid sequence of SEQ ID NO:6, fused to an alternative VP16 transcriptional activator with amino acid sequence SEQ ID NO:40. In each case the open reading frame encoding the transcriptional activator was linked to an SV40 promoter with nucleotide sequence SEQ ID NO:28, which promoter is operable in mammalian cells.

HEK293 suspension cells were grown in flasks in Expi293 media at 37° C. with 8% CO2, in an incubator with 25 mm throw at 125 RPM. The cells were passaged at a density of 2.5×106 cells/ml 24 hours prior to transfection. Cells were diluted to 3×106 cells/ml, and 700 ul were aliquoted into 96 deep well plates. Each DNA construct was transfected three independent times using ExpiFectamine™ 293 Transfection Reagent at a 1:2.7 DNA:Transfection reagent ratio. After transfection, the cells were placed in an incubator at 37° C. with 8% CO2, with a 3 mm throw shaking at 1,000 RPM. 24 hours post-transfection, the cultures were fed with ExpiFectamine™ 293 Transfection Enhancer 1 and ExpiFectamine™ 293 Transfection Enhancer 2. After this feeding, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 5.

Table 5 (rows 4 and 5) shows that the control tet-inducible minimal human CMV promoter resulted in similar induction profiles using either of the different transcriptional activators (with amino acid sequences SEQ ID NOS:8 and 9, which comprise the VP16-derived activation domains with amino acid sequences SEQ ID NOS:7 and 40 respectively). Table 5 also shows that the array of 8 tet operators joined to minimal human CMV promoter with nucleotide sequence SEQ ID NO:22 performs very comparably to the control tet-inducible minimal human CMV promoter (compare Table 5 row 6 with row 5). The minimal murine CMV promoter showed substantially lower levels of induced gene expression than the human minimal CMV promoter sequences (Table 5 row 7). However the inducible promoter comprising the chimpanzee minimal CMV promoter resulted in consistently higher levels of expression than any of the other inducible promoters (Table 5 row 8).

Thus a tet operator array fused to the 5' end of a chimpanzee minimal CMV promoter with nucleotide sequence SEQ ID NO:24 produces a highly effective tet-inducible promoter.

6. Inducible Promoters Comprising Tet Binding Sites 5' of the Promoter in Transiently Transfected CHO-S Cells We tested several embodiments of tet-inducible promoters for their ability to respond to increasing concentrations of doxycycline after transient transfection into CHO-S cells.

Constructs were as described in Example 5. CHO-s cells were grown in flasks in ExpiCHO media at 37° C. with 5% CO2, in an incubator with 25 mm throw at 125 RPM. The cells were passaged at a density of 4.5×106 cells/ml 24 hours prior to transfection. Cells were diluted to 6×106 cells/ml, and 800 ul were aliquoted into 96 deep well plates. Each DNA construct was transfected three independent times using ExpiFectamine™ CHO Transfection Reagent at a 1:4 DNA:Transfection reagent ratio. After transfection, the cells were placed in an incubator at 37° C. with 5% CO2, with a 3 mm throw shaking at 1,000 RPM. 24 hours post-transfection, the cultures were fed with ExpiFectamine™ CHO Enhancer and ExpiCHO Feed. After feeding the cells, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 6.

Table 6 shows that the tet-inducible promoters performed similarly in transiently transfected CHO cells as they did in transiently transfected HEK 293 cells. The inducible promoter comprising the chimpanzee minimal CMV promoter resulted in consistently higher levels of expression than any of the other inducible promoters (Table 6 row 8).

7. Inducible Promoters Comprising Tet Binding Sites 5' of the Promoter in Stably Transfected CHO-K1 Cells We tested several embodiments of tet-inducible promoters for their ability to respond to increasing concentrations of doxycycline after stable integration into CHO-K1 cells.

DNA constructs were used as described in Example 5. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30 or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 7. Table 7 shows that the minimal chimpanzee CMV tet-inducible promoter shows very good inducible expression when stably integrated into the genome of a host cell.

8. Inducible Promoters Comprising Different Numbers of Tet Binding Sites 5' of the Promoter in Stably Transfected CHO-K1 Cells We tested three embodiments of tet-inducible promoters with different numbers of tet operators for their ability to respond to increasing concentrations of doxycycline after stable integration into CHO-K1 cells.

A minimal CMV promoter from chimpanzee CMV (with nucleotide sequence SEQ ID NO:24) was fused at its 5' end, to an array of 3, 6 or 8 tet operators (with nucleotide sequences SEQ ID NOs: 153, 152 and 3 respectively), to create 3 tet-inducible promoters. The 3' end of each minimal promoter was fused to a 5'UTR with nucleotide sequence SEQ ID NO:30. The 3' end of each 5'UTR was fused to an open reading frame encoding Dasher GFP with amino acid sequence SEQ ID NO:32.

Each of the different tet-inducible promoter-GFP transcriptional units was cloned onto a plasmid comprising a second transcriptional unit. The second transcriptional unit comprised an open reading frame encoding a transcriptional activator comprising a modified tet repressor with amino acid sequence of SEQ ID NO:6, fused to a VP16 transcriptional activator with amino acid sequence SEQ ID NO:7. In each case the open reading frame encoding the transcriptional activator was linked to an SV40 promoter with nucleotide sequence SEQ ID NO:28, which promoter is operable in mammalian cells. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30, 100 or 300 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48 and 72 hours post-induction. The average fluorescence at 525 nm for each set of 3 replicates was divided by optical density at 600 nm for each set of 3 replicates to provide an average measure of fluorescence normalized by cell number. Results are shown in Table 8. Table 8 shows that the minimal chimpanzee CMV tet-inducible promoter, operably linked to 3, 6 or 8 repeats of the tet operator, shows very good inducible expression when stably integrated into the genome of a host cell. It also shows that a smaller number of repeats resulted in a higher level of expression in the absence of doxycycline (compare Table 8 columns B, G, L and Q for row 3 with 8 tet operator repeats, row 4 with 6 tet operator repeats, and row 5 with 3 tet operator repeats. As a control, Table 8 row 6 shows the average fluorescence in cells with no integrated inducible transposon).

9. A Hybrid Human-Mouse CMV Promoter is Advantageous for Expression in Stably Transfected Mammalian Cells We tested a hybrid human-mouse promoter comprising a segment of a mouse CMV promoter of SEQ ID NO:16 upstream from a segment of a human CMV promoter of SEQ ID NO:13, wherein the hybrid promoter lacks a CG motif at positions corresponding to positions 42 and 43 of SEQ ID NO:13. The junction between contiguous segments is within the sequence ACGTCAATGGGA, which is common to the mouse and human CMV promoter sequences. The promoter has nucleotide sequence SEQ ID NO: 12, which comprises SEQ ID NO: 10 plus 13 bases (5'-GTT-TAGTGAACCG-3') immediately 5' of the transcriptional start site.

The hybrid promoter was operably linked to an open reading frame encoding an antibody heavy chain with amino acid sequence SEQ ID NO: 154. The construct further comprised a mouse CMV promoter with nucleotide sequence SEQ ID NO:16 operably linked to an open reading frame with amino acid sequence SEQ ID NO: 155. The construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Two additional transposon constructs were prepared, in which the hybrid promoter operably linked to the antibody heavy chain was replaced by either a murine CMV promoter with nucleotide sequence SEQ ID NO: 16, or by a human CMV promoter with nucleotide sequence SEQ ID NO: 13.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Recovered pools were then grown in a 7-day fed-batch using Sigma Advanced Fed Batch media. Antibody titers were measured in culture supernatant using an Octet. Table 9 shows the titers measured at day 7, and the specific productivities (calculated as the amount of antibody produced per cell per day).

As shown in Table 9, the volumetric (Table 9 column D) and specific (Table 9 column C) productivities obtained using the hybrid promoter with nucleotide sequence comprising SEQ ID NO: 10 operably linked to the heavy chain open reading frame (Table 9 row 1) were higher than those obtained using either of the promoters from which the hybrid promoter was derived (Table 9 rows 2 and 3). We conclude that the hybrid human/murine CMV promoter comprising SEQ ID NO: 10 is advantageous for expression of heterologous proteins in CHO cells.

X TABLES DESCRIPTION

Table 1. DNA constructs comprising two transcriptional units were prepared as described in Example 3. Each construct comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each construct further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Each construct was transfected into HEK 293 cells in 3 independent transfections, induced with doxycycline and cell numbers and fluorescence were measured as described in Example 1. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 2. DNA constructs comprising two transcriptional units were prepared as described in Example 1. Each construct comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each construct further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Each construct was transfected into CHO-s cells in 3 independent transfections, induced with doxycycline and cell numbers and fluorescence were measured as described in Example 2. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 3. DNA transposons comprising two transcriptional units were prepared as described in Example 1. Each transposon comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each transposon further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Transposons were stably transfected into CHO cells and selected, after recovery three separate cultures for each stable cell line were induced with doxycycline and cell numbers and fluorescence were measured as described in Example 3. Fluorescence was measured at 525 nm and cell density was measured as optical density at 600 nm. The average fluorescence at 525 nm for each set of 3 replicates was divided by optical density at 600 nm for each set of 3 replicates to provide an average measure of fluorescence normalized by cell number shown in columns F to Z. Days post-induction are shown in row 1, doxycycline concentrations are shown in row 2.

Table 4. DNA transposons comprising two transcriptional units were prepared as described in Example 4. Each transposon comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each transposon further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. The promoter sequences indicated in column E in rows 6 and 7 also include the 5'UTR including the Kozak sequence immediately before the translational initiation site for the tet repressor. Transposons were stably transfected into CHO cells and selected, after recovery three separate cultures for each stable cell line were induced with doxycycline and cell numbers and fluorescence were measured as described in Example 4. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number and is shown in columns F to W. Days post-induction are shown in row 1, doxycycline concentrations are shown in row 2.

Table 5. DNA constructs comprising two transcriptional units were prepared as described in Example 5. Each construct comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Each construct was transfected into HEK 293 cells in 3 independent transfections, induced with doxycycline and cell numbers and fluorescence were measured as described in Example 5. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 6. DNA constructs comprising two transcriptional units were prepared as described in Example 5. Each construct comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Each construct was transfected into CHO-S cells in 3 independent transfections, induced with doxycycline and cell numbers and fluorescence were measured as described in Example 6. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to Q. Days post-induction are shown in row 1, doxycycline concentrations are shown in row 2.

Table 7. DNA transposons comprising two transcriptional units were prepared as described in Example 7. Each transposon comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Transposons were stably transfected into CHO cells and selected, after recovery three separate cultures for each stable cell line were induced with doxycycline and cell numbers and fluorescence were measured as described in Example 7. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to Q. Days post-induction are shown in row 1, doxycycline concentrations are shown in row 2.

Table 8. DNA transposons comprising two transcriptional units were prepared as described in Example 8. Each transposon comprised a first transcriptional unit comprising a minimal chimpanzee promoter whose 5' end was fused to an array of tet operators with nucleotide sequence given by the SEQ ID NO shown in column A. The promoter was operably linked to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Transposons were stably transfected into CHO cells and selected, after recovery three separate cultures for each stable cell line were induced with doxycycline and cell numbers and fluorescence were measured as described in Example 8. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns B to U. Days post-induction are shown in row 1, doxycycline concentrations are shown in row 2. Control cells with no integrated transposon are shown in row 6.

Table 9. DNA transposons comprising two transcriptional units were prepared as described in Example 9. Each transposon comprised a first transcriptional unit comprising a mouse CMV promoter operably linked to an open reading frame encoding an antibody light chain. Each transposon further comprised a second transcriptional unit comprising a promoter named in column A and with nucleotide given by the SEQ ID NO in column B, operably linked to an open reading frame encoding an antibody heavy chain. Transposons were stably transfected into CHO cells and selected as described in Example 9. The specific productivity of each CHO cell pool is shown in column C, the volumetric productivity is shown in column D.

XI TABLES

TABLE 1

| | A<br>inducible<br>promoter<br>name | B<br>inducible<br>promoter<br>SEQ ID<br>(excluding<br>the operators) | C<br>inducible<br>promoter<br>SEQ ID<br>(including<br>the operators) | D<br>repressor<br>promoter<br>name | E<br>repressor<br>promoter<br>SEQ ID | F | G | H<br>GFP<br>Fluorescence | I | J | K<br>GFP<br>Fluorescence |
|---|---|---|---|---|---|---|---|---|---|---|---|
| 1 | day | | | | | 0 | 0 | 0 | 0 | 1 | 1 |
| 2 | dox<br>concen-<br>tration<br>ng/ml | | | | | 0 | 10 | 30 | 100 | 0 | 10 |

TABLE 1-continued

| | A inducible promoter name | B inducible promoter SEQ ID (excluding the operators) | C inducible promoter SEQ ID (including the operators) | D repressor promoter name | E repressor promoter SEQ ID | F | G | H | I | J | K |
|---|---|---|---|---|---|---|---|---|---|---|---|
| 3 | CMV Mm/Hs | 10 | 11 | PGK | 18 | 945 | 903 | 875 | 1,124 | 849 | 6,482 |
| 4 | CMV Mm/Hs | 10 | 11 | EEF2 | 17 | 835 | 963 | 903 | 944 | 662 | 1,491 |
| 5 | CMV Mm/Hs | 10 | 11 | CMV(Mm) | 16 | 752 | 875 | 877 | 936 | 723 | 864 |
| 6 | CMV(Hs) | 36 | 15 | CMV(Hs) | 13 | 689 | 659 | 650 | 786 | 557 | 734 |

| | L GFP Fluorescence | M | N | O GFP Fluorescence | P | Q | R | S GFP Fluorescence | T | U |
|---|---|---|---|---|---|---|---|---|---|---|
| 1 | 1 | 1 | 2 | 2 | 2 | 2 | 3 | 3 | 3 | 3 |
| 2 | 30 | 100 | 0 | 10 | 30 | 100 | 0 | 10 | 30 | 100 |
| 3 | 9,699 | 8,401 | 854 | 6,622 | 19,504 | 21,008 | 838 | 7,107 | 19,038 | 22,871 |
| 4 | 3,831 | 11,368 | 755 | 1,562 | 4,399 | 17,795 | 699 | 1,400 | 4,199 | 16,295 |
| 5 | 1,532 | 9,319 | 672 | 880 | 1,632 | 22,690 | 685 | 889 | 1,595 | 21,029 |
| 6 | 993 | 12,312 | 510 | 623 | 903 | 11,250 | 517 | 604 | 829 | 11,212 |

TABLE 2

| | A inducible promoter name | B inducible promoter SEQ ID (excluding the operators) | C inducible promoter SEQ ID (including the operators) | D repressor promoter name | E repressor promoter SEQ ID | F | G | H | I GFP Fluorescence | J | K GFP Fluorescence |
|---|---|---|---|---|---|---|---|---|---|---|---|
| 1 | day | | | | | 0 | 0 | 0 | 0 | 1 | 1 |
| 2 | dox concentration ng/ml | | | | | 0 | 10 | 30 | 100 | 0 | 10 |
| 3 | CMV Mm/Hs | 10 | 11 | PGK | 18 | 897 | 1042 | 969 | 1187 | 1198 | 16964 |
| 4 | CMV Mm/Hs | 10 | 11 | EEF2 | 17 | 832 | 945 | 998 | 1096 | 1071 | 15698 |
| 5 | CMV Mm/Hs | 10 | 11 | CMV(Mm) | 16 | 654 | 741 | 701 | 745 | 667 | 890 |
| 6 | CMV(Hs) | 36 | 15 | CMV(Hs) | 13 | 466 | 456 | 523 | 487 | 427 | 6091 |

| | L GFP Fluorescence | M | N | O GFP Fluorescence | P | Q | R | S GFP Fluorescence | T | U |
|---|---|---|---|---|---|---|---|---|---|---|
| 1 | 1 | 1 | 2 | 2 | 2 | 2 | 3 | 3 | 3 | 3 |
| 2 | 30 | 100 | 0 | 10 | 30 | 100 | 0 | 10 | 30 | 100 |
| 3 | 16709 | 17430 | 1341 | 41392 | 41037 | 37035 | 1277 | 54023 | 49654 | 49327 |
| 4 | 17635 | 18772 | 1092 | 32485 | 40988 | 41047 | 1015 | 32201 | 54880 | 55860 |
| 5 | 2413 | 13560 | 631 | 863 | 2267 | 16063 | 614 | 789 | 2038 | 14076 |
| 6 | 9504 | 8985 | 403 | 7373 | 27836 | 27938 | 369 | 6639 | 29770 | 35882 |

TABLE 3

| | A inducible promoter name | B inducible promoter SEQ ID (excluding the operators) | C inducible promoter SEQ ID (including the operators) | D repressor promoter name | E repressor promoter SEQ ID | F | G | H | I | J | K | L |
|---|---|---|---|---|---|---|---|---|---|---|---|---|
| 1 | day | | | | | 0 | 0 | 0 | 0 | 0 | 0 | 0 |
| 2 | dox concentration ng/ml | | | | | 0 | 10 | 30 | 100 | 300 | 1,000 | 3,000 |
| 3 | CMV Mm/Hs | 10 | 11 | PGK | 18 | 932 | 946 | 958 | 936 | 981 | 1,102 | 1,211 |
| 4 | CMV Mm/Hs | 10 | 11 | EEF2 | 17 | 903 | 925 | 916 | 1,048 | 1,138 | 1,126 | 1,183 |
| 5 | CMV Mm/Hs | 10 | 11 | CMV(Mm) | 16 | 923 | 972 | 1,078 | 1,070 | 1,016 | 1,077 | 969 |
| 6 | CMV(Hs) | 36 | 15 | CMV(Hs) | 13 | 943 | 935 | 939 | 1,008 | 1,096 | 1,008 | 1,007 |

TABLE 3-continued

| | | M | N | O | P | Q | R | S | T | U | V | W | X | Y | Z |
|---|---|---|---|---|---|---|---|---|---|---|---|---|---|---|---|
| | | | | | | GFP Fluorescence | | | | | | | GFP Fluorescence | | |
| | 1 | 1 | 1 | 1 | 1 | 1 | 1 | 1 | 2 | 2 | 2 | 2 | 2 | 2 | 2 |
| | 2 | 0 | 10 | 30 | 100 | 300 | 1,000 | 3,000 | 0 | 10 | 30 | 100 | 300 | 1,000 | 3,000 |
| | 3 | 432 | 922 | 3,613 | 3,651 | 4,012 | 3,879 | 3,796 | 234 | 632 | 3,873 | 8,720 | 8,935 | 8,779 | 8,807 |
| | 4 | 435 | 593 | 2,271 | 3,957 | 3,806 | 3,922 | 3,873 | 212 | 344 | 1,704 | 8,143 | 8,866 | 8,521 | 8,363 |
| | 5 | 423 | 429 | 426 | 452 | 1,425 | 2,304 | 2,393 | 212 | 222 | 222 | 250 | 985 | 4,867 | 4,967 |
| | 6 | 448 | 434 | 447 | 665 | 2,633 | 2,971 | 2,894 | 230 | 241 | 254 | 407 | 3,484 | 5,464 | 5,054 |

TABLE 4

| | | A inducible promoter name | B inducible promoter SEQ ID (excluding the operators) | C inducible promoter SEQ ID (including the operators) | D repressor promoter name | E repressor promoter SEQ ID | F | G | H | I | J | K |
|---|---|---|---|---|---|---|---|---|---|---|---|---|
| | | | | | | | | | GFP Fluorescence | | | |
| 1 | day | | | | | | 0 | 0 | 0 | 0 | 0 | 0 |
| 2 | dox concentration ng/ml | | | | | | 0 | 10 | 30 | 100 | 300 | 1,000 |
| 3 | | none | none | none | none | none | 588 | 608 | 593 | 604 | 600 | 670 |
| 4 | | CMV (Hs) | 36 | 15 | EEF2_50 (Rn) | 17 | 775 | 865 | 902 | 886 | 863 | 903 |
| 5 | | CMV (Hs) | 36 | 15 | GADPH (Hs) | 19 | 794 | 822 | 885 | 808 | 870 | 867 |
| 6 | | CMV (Hs) | 36 | 15 | PGK (Hs)_UTR | 37* | 765 | 827 | 842 | 836 | 893 | 949 |
| 7 | | CMV (Hs) | 36 | 15 | PGK (Hs) 6T | 21* | 1,226 | 1,305 | 1,372 | 1,324 | 1,444 | 1,313 |

| | | L | M | N | O | P | Q | R | S | T | U | V | W |
|---|---|---|---|---|---|---|---|---|---|---|---|---|---|
| | | | | GFP Fluorescence | | | | | | | GFP Fluorescence | | |
| | 1 | 1 | 1 | 1 | 1 | 1 | 1 | 1 | 2 | 2 | 2 | 2 | 2 |
| | 2 | 0 | 10 | 30 | 100 | 300 | 1,000 | 0 | 10 | 30 | 100 | 300 | 1,000 |
| | 3 | 303 | 307 | 312 | 330 | 343 | 307 | 234 | 254 | 277 | 289 | 273 | 252 |
| | 4 | 379 | 359 | 384 | 535 | 4,536 | 5,029 | 229 | 233 | 242 | 408 | 5,327 | 10,067 |
| | 5 | 386 | 351 | 384 | 463 | 4,013 | 5,458 | 243 | 262 | 257 | 331 | 4,078 | 13,739 |
| | 6 | 392 | 385 | 422 | 1,733 | 8,857 | 8,473 | 252 | 277 | 311 | 1,373 | 11,539 | 20,350 |
| | 7 | 984 | 10,241 | 11,270 | 11,056 | 11,001 | 11,215 | 917 | 13,449 | 22,540 | 23,087 | 23,294 | 23,032 |

TABLE 5

| | | A minimal promoter name | B tet operator array SEQ ID | C minimal promoter SEQ ID | D 5'UTR SEQ ID | E activator SEQ ID | F | G | H | I | J | K |
|---|---|---|---|---|---|---|---|---|---|---|---|---|
| | | | | | | | | GFP Fluorescence | | | GFP Fluorescence | |
| 1 | day | | | | | | 0 | 0 | 0 | 0 | 1 | 1 |
| 2 | dox concentration ng/ml | | | | | | 0 | 10 | 30 | 100 | 0 | 10 |
| 3 | | none | none | none | -na- | none | 327 | 352 | 336 | 356 | 181 | 171 |
| 4 | | CMV (human) | 4 | 38 | 39 | 9 | 319 | 364 | 405 | 385 | 207 | 2,941 |
| 5 | | CMV (human) | 4 | 38 | 39 | 8 | 347 | 353 | 421 | 381 | 227 | 2,868 |
| 6 | | CMV (human) | 3 | 22 | 30 | 8 | 340 | 405 | 423 | 438 | 227 | 2,832 |
| 7 | | CMV (mouse) | 3 | 23 | 30 | 8 | 366 | 372 | 413 | 445 | 213 | 1,228 |
| 8 | | CMV (chimp) | 3 | 24 | 30 | 8 | 382 | 381 | 455 | 409 | 219 | 5,430 |

TABLE 5-continued

| | L | M | N | O | P | Q | R | S | T | U |
|---|---|---|---|---|---|---|---|---|---|---|
| | GFP Fluorescence | | | GFP Fluorescence | | | | GFP Fluorescence | | |
| 1 | 1 | 1 | 2 | 2 | 2 | 2 | 3 | 3 | 3 | 3 |
| 2 | 30 | 100 | 0 | 10 | 30 | 100 | 0 | 10 | 30 | 100 |
| 3 | 182 | 162 | 162 | 167 | 170 | 147 | 175 | 161 | 165 | 116 |
| 4 | 6,311 | 10,235 | 192 | 7,793 | 19,524 | 29,747 | 186 | 7,144 | 14,532 | 29,358 |
| 5 | 7,021 | 12,696 | 221 | 6,924 | 20,381 | 27,913 | 204 | 7,620 | 23,733 | 31,291 |
| 6 | 5,125 | 11,810 | 208 | 5,840 | 20,094 | 27,444 | 157 | 8,154 | 24,094 | 33,560 |
| 7 | 2,375 | 3,584 | 187 | 3,096 | 6,866 | 12,462 | 165 | 3,765 | 8,315 | 14,273 |
| 8 | 10,049 | 14,957 | 191 | 7,203 | 23,939 | 35,555 | 181 | 10,699 | 24,578 | 40,111 |

TABLE 6

| | A minimal promoter name | B tet operator array SEQ ID | C minimal promoter SEQ ID | D 5'UTR SEQ ID | E activator SEQ ID | F | G | H | I |
|---|---|---|---|---|---|---|---|---|---|
| | | | | | | | GFP Fluorescence | | |
| 1 | day | | | | | 0 | 0 | 0 | 0 |
| 2 | dox concentration ng/ml | | | | | 0 | 10 | 30 | 100 |
| 3 | | none | none | none | -na- | 299 | 324 | 307 | 338 |
| 4 | | CMV (human) | 4 | 38 | 39 | 9 | 321 | 308 | 341 | 377 |
| 5 | | CMV (human) | 4 | 38 | 39 | 8 | 330 | 322 | 354 | 339 |
| 6 | | CMV (human) | 3 | 22 | 30 | 8 | 328 | 350 | 343 | 347 |
| 7 | | CMV (mouse) | 3 | 23 | 30 | 8 | 338 | 338 | 355 | 357 |
| 8 | | CMV (chimp) | 3 | 24 | 30 | 8 | 318 | 350 | 343 | 344 |

| | J | K | L | M | N | O | P | Q |
|---|---|---|---|---|---|---|---|---|
| | GFP Fluorescence | | | | | GFP Fluorescence | | |
| 1 | 1 | 1 | 1 | 1 | 2 | 2 | 2 | 2 |
| 2 | 0 | 10 | 30 | 100 | 0 | 10 | 30 | 100 |
| 3 | 279 | 280 | 285 | 332 | 221 | 250 | 248 | 251 |
| 4 | 329 | 3,309 | 4,478 | 6,296 | 284 | 8,452 | 10,291 | 12,820 |
| 5 | 333 | 3,621 | 5,740 | 8,261 | 305 | 8,336 | 13,034 | 15,582 |
| 6 | 315 | 4,160 | 5,731 | 8,761 | 252 | 10,583 | 14,017 | 18,621 |
| 7 | 325 | 2,015 | 2,258 | 2,426 | 297 | 3,432 | 3,997 | 4,214 |
| 8 | 314 | 6,875 | 11,122 | 12,640 | 265 | 14,610 | 22,281 | 25,388 |

TABLE 7

| | A minimal promoter name | B tet operator array SEQ ID | C minimal promoter SEQ ID | D 5'UTR SEQ ID | E activator SEQ ID | F | G | H | I |
|---|---|---|---|---|---|---|---|---|---|
| | | | | | | | GFP Fluorescence | | |
| 1 | day | | | | | 0 | 0 | 0 | 0 |
| 2 | dox concentration ng/ml | | | | | 0 | 10 | 30 | 100 |
| 3 | | CMV (human) | 4 | 38 | 39 | 9 | 680 | 729 | 771 | 769 |
| 4 | | CMV (human) | 4 | 38 | 39 | 8 | 747 | 830 | 824 | 841 |
| 5 | | CMV (human) | 3 | 22 | 30 | 8 | 696 | 681 | 719 | 772 |
| 6 | | CMV (mouse) | 3 | 23 | 30 | 8 | 667 | 647 | 722 | 698 |
| 7 | | CMV (chimp) | 3 | 24 | 30 | 8 | 616 | 591 | 651 | 680 |

TABLE 7-continued

|   | J | K GFP Fluorescence | L | M | N | O GFP Fluorescence | P | Q |
|---|---|---|---|---|---|---|---|---|
| 1 | 1 | 1 | 1 | 1 | 3 | 3 | 3 | 3 |
| 2 | 0 | 10 | 30 | 100 | 0 | 10 | 30 | 100 |
| 3 | 518 | 5,741 | 21,530 | 32,702 | 455 | 4,950 | 26,641 | 59,550 |
| 4 | 540 | 5,725 | 25,107 | 37,497 | 441 | 4,473 | 28,432 | 73,749 |
| 5 | 443 | 8,913 | 30,944 | 39,670 | 314 | 7,247 | 34,490 | 76,695 |
| 6 | 479 | 4,009 | 15,993 | 20,063 | 364 | 3,060 | 19,759 | 36,385 |
| 7 | 435 | 9,141 | 27,396 | 31,841 | 304 | 7,046 | 38,680 | 75,416 |

TABLE 8

|   | A tet operator array SEQ ID | B | C | D GFP Fluorescence | E | F | G | H | I GFP Fluorescence | J | K |
|---|---|---|---|---|---|---|---|---|---|---|---|
| 1 | day |  | 0 | 0 | 0 | 0 | 0 | 1 | 1 | 1 | 1 | 1 |
| 2 | dox concentration ng/ml |  | 0 | 10 | 30 | 100 | 300 | 0 | 10 | 30 | 100 | 300 |
| 3 |  | 3 | 987 | 1,056 | 1,037 | 1,115 | 1,007 | 587 | 8,625 | 28,451 | 38,463 | 36,978 |
| 4 |  | 152 | 1,184 | 1,229 | 1,179 | 1,147 | 1,227 | 840 | 13,360 | 41,155 | 43,771 | 45,851 |
| 5 |  | 153 | 1,851 | 1,772 | 1,690 | 1,947 | 1,735 | 1,371 | 7,789 | 25,179 | 34,587 | 35,641 |
| 6 | C129 | none | 873 | 884 | 832 | 963 | 894 | 287 | 288 | 294 | 309 | 289 |

|   | L | M | N GFP Fluorescence | O | P | Q | R | S GFP Fluorescence | T | U |
|---|---|---|---|---|---|---|---|---|---|---|
| 1 | 2 | 2 | 2 | 2 | 2 | 3 | 3 | 3 | 3 | 3 |
| 2 | 0 | 10 | 30 | 100 | 300 | 0 | 10 | 30 | 100 | 300 |
| 3 | 454 | 6,811 | 37,624 | 69,761 | 84,619 | 383 | 5,801 | 30,114 | 59,567 | 85,327 |
| 4 | 767 | 11,247 | 43,311 | 83,912 | 94,533 | 714 | 9,075 | 45,019 | 77,306 | 99,674 |
| 5 | 1,384 | 7,076 | 30,440 | 56,861 | 73,496 | 1,397 | 5,778 | 25,860 | 52,691 | 81,195 |
| 6 | 202 | 212 | 227 | 218 | 222 | 162 | 160 | 167 | 170 | 171 |

TABLE 9

|   | A HC promoter name | B HC promoter SEQ ID NO | C specific productivity (pg/cell/day) | D volumetric productivity (g/L) |
|---|---|---|---|---|
| 1 | hybrid | 12 | 23.00 | 1,617 |
| 2 | human | 13 | 19.30 | 1,491 |
| 3 | murine | 16 | 13.68 | 1,312 |

All publications, patents and patent applications, accession numbers, websites and the like mentioned in this specification are incorporated by reference to the same extent as if each individual publication, patent or patent application was so individually denoted. To the extent different content is associated with an accession number or other reference at different times, the content in effect as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A nucleic acid comprising a transcriptional unit comprising a promoter having a sequence comprising SEQ ID NO:24, and no more than ten contiguous nucleotides on the 5' side of SEQ ID NO:24 from a natural chimpanzee CMV promoter with which SEQ ID NO:24 is naturally associated, in operable linkage with a heterologous coding segment.

2. The nucleic acid of claim 1, wherein the promoter lacks a 5' flanking sequence from a natural chimpanzee CMV promoter with which it is naturally associated.

3. The nucleic acid of claim 1, further comprising at least first and second tet-operators in operable linkage with the promoter.

4. The nucleic acid of claim 3, wherein the first and second tet-operators are 5' to the promoter.

5. The nucleic acid of claim 4, comprising three, six or eight tet-operators 5' to the promoter.

6. The nucleic acid of claim 1, further comprising at least one cumate operator in operable linkage with the promoter.

7. The nucleic acid of claim 6 comprising any of SEQ ID NOS:164-166 providing the promoter and cumate operator.

8. The nucleic acid of claim 6 comprising any of SEQ ID NOS:167-169 providing the promoter, the cumate operator and a 5' UTR.

9. The nucleic acid of claim 1, further comprising a segment encoding a 5' UTR.

10. The nucleic acid of claim 9, wherein the segment encoding the 5' UTR has a sequence comprising SEQ ID NO:29.

11. The nucleic acid of claim 1, further comprising a second transcriptional unit comprising a second promoter operably linked to a segment encoding a tet-repressor effective to bind a tet-operator in the absence of tetracycline or doxycycline or modified-tet-repressor effective to bind a tet-operator in the presence of tetracycline or doxycycline, wherein the tet-repressor or modified tet-repressor is fused to a transcriptional activator.

12. The nucleic acid of claim 1, further comprising a second transcriptional unit comprising a second promoter operably linked to a segment encoding a cumate repressor effective to bind a cumate operator in the absence of cumate or modified cumate repressor effective to bind a cumate operator in the presence of cumate, wherein the cumate repressor or modified cumate repressor is fused to a transcriptional activator.

13. The nucleic acid of claim 11, wherein the second transcriptional unit further comprises a polyadenylation sequence.

14. The nucleic acid of claim 11, wherein the tet-repressor has an amino acid sequence comprising SEQ ID NO:5.

15. The nucleic acid of claim 11, wherein the modified tet-repressor has an amino acid sequence comprising SEQ ID NO:6.

16. The nucleic acid of claim 12, wherein the cumate repressor has an amino acid sequence comprising SEQ ID NO:170, or the modified cumate repressor linked to the transcriptional activator has an amino acid sequence comprising SEQ ID NO:172.

17. The nucleic acid of claim 1, wherein the coding segment encodes a protein.

18. A transposon comprising the nucleic acid of claim 1 flanked by inverted repeats of the transposon.

19. The transposon of claim 18, which is a piggyBac or piggyBac-like transposon.

20. The nucleic acid of claim 1, wherein the promoter consists essentially of SEQ ID NO:24.

21. The nucleic acid of claim 1, wherein the promoter consists of SEQ ID NO:24.

22. The nucleic acid of claim 1, wherein the promoter by itself without an enhancer supports transcription of the heterologous coding segment at no more than ten transcripts per cell in CHO cells.

23. An isolated cell transformed with the nucleic acid of claim 1.

24. The cell of claim 23, which is mammalian.

25. A non-human animal transformed with the nucleic acid of claim 1.

26. A cell in vitro or a nonhuman transgenic animal having a genome comprising (a) a promoter having a sequence comprising SEQ ID NO:24, and no more than ten contiguous nucleotides on the 5' side of the SEQ ID NO:24 from a natural chimpanzee CMV promoter with which SEQ ID NO:24 is naturally associated, operably linked to at least two tet operators and a coding segment, and (b) a promoter operably linked to a tet-repressor or modified tet-repressor fused to transcriptional activation domain, wherein expression of the coding segment can be regulated by supplying tetracycline or doxycycline, or other tetracycline analog to the cell or nonhuman transgenic animal, or (a) a promoter having a sequence comprising SEQ ID NO:24, and no more than ten contiguous nucleotides on the 5' side of SEQ ID NO:24 from a natural chimpanzee CMV promoter with which SEQ ID NO:24 is naturally associated, operably linked to at least one cumate operators and a coding segment, and (b) a promoter operably linked to a cumate repressor or modified cumate repressor fused to transcriptional activation domain, wherein expression of the coding segment can be regulated by supplying cumate to the cell or nonhuman transgenic animal.

27. A method for inducible expression of a coding segment comprising; providing a first transcriptional unit comprising in operable linkage with a least two tet-operators, a promoter having a nucleotide sequence comprising SEQ ID NO:24, and no more than ten contiguous nucleotides on the 5' side of SEQ ID NO:24 from a natural chimpanzee CMV promoter with which SEQ ID NO:24 is naturally associated, and a coding segment, and a second transcriptional unit comprising in operable linkage a promoter, and a segment encoding a tet-repressor or modified tet-repressor fused to a transcriptional activator, wherein the tet-repressor fused to the transcriptional activator is expressed and in the absence of tetracycline or doxycycline the tet-repressor binds to the at least two tet-operators and expression of the coding segment is increased, or the modified tet-repressor fused to the transcriptional activator is expressed and in the presence of tetracycline or doxycycline the modified tet-repressor binds to the at least two tet-operators and expression of the coding segment is increased, or providing a first transcriptional unit comprising in operable linkage with a least one cumate operators, a promoter having a nucleotide sequence comprising SEQ ID NO:24, and no more than ten contiguous nucleotides on the 5' side of SEQ ID NO:24 from a natural chimpanzee CMV promoter with which SEQ ID NO:24 is naturally associated, and a coding segment, and a second transcriptional unit comprising in operable linkage a promoter, and a segment encoding a cumate repressor or modified cumate repressor fused to a transcriptional activator, wherein the cumate repressor fused to the transcriptional activator is expressed and in the absence of cumate, the cumate repressor binds to the at least one cumate operator and expression of the coding segment is increased, or the modified cumate repressor fused to the transcriptional activator is expressed and in the presence of cumate the modified cumate repressor binds to the at least one cumate operators and expression of the coding segment is increased.

28. The method of claim 27, wherein the first and second transcriptional units are components of the same contiguous DNA molecule.

29. The method of claim 28, wherein the first and second transcriptional units are components of a transposon.

30. The method of claim 29, wherein the transposon is a piggyBac or piggyBac-like transposon.

31. The method of claim 28, further comprising introducing the contiguous DNA molecule into a cell.

32. The method of claim 31, wherein the cell is a mammalian cell, and wherein the first and second transcriptional units integrate into the genome of the cell.

33. The method of claim 27, further comprising culturing the cell and supplying tetracycline or doxycycline or other tetracycline analog, or cumate or an analog to culture media of the cell.

\* \* \* \* \*

UNITED STATES PATENT AND TRADEMARK OFFICE
CERTIFICATE OF CORRECTION

PATENT NO. : 11,566,262 B2
APPLICATION NO. : 17/700405
DATED : January 31, 2023
INVENTOR(S) : Jeremy Minshull It is certified that error appears in the above-identified patent and that said Letters Patent is hereby corrected as shown below:

In the Claims

In Column 313, Line 9, Claim 26, delete "of the SEQ" and insert -- of SEQ --, therefor.

In Column 313, Line 12, Claim 26, delete "tet operators" and insert -- tet-operators --, therefor.

In Column 313, Line 22, Claim 26, delete "operators" and insert -- operator --, therefor.

In Column 314, Line 8, Claim 27, delete "operators," and insert -- operator, --, therefor.

In Column 314, Line 23, Claim 27, delete "operators" and insert -- operator --, therefor.

Signed and Sealed this
Twenty-sixth Day of September, 2023

Katherine Kelly Vidal
*Director of the United States Patent and Trademark Office*

SEQUENCE LISTING

<160> NUMBER OF SEQ ID NOS: 172

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
tccctatcag tgatagaga                                             19

<210> SEQ ID NO 2

```
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 2
tccctatcag tgatagagan ntccctatca gtgatagaga                              40

<210> SEQ ID NO 3
<211> LENGTH: 283
<212> TYPE: DNA
<213> ORGANISM: Artificial sequence
<220> FEATURE:
<223> OTHER INFORMATION: Synthetic

<400> SEQUENCE: 3
tccctatcag tgatagagat gcttctccac tcactatccc tatcagtgat agagagtaaa        60
ctcttcatag gttccctatc agtgatagag agtctagtct gcataccttc cctatcagtg       120
atagagagac aactccttat aggttcccta tcagtgatag agagtaaact ggtcatacct       180
tccctatcag tgatagagag taaactgtag ataccttccc tatcagtgat agagagtaaa       240
ctggatatag gttccctatc agtgatagag aaagcttata cct                        283

<210> SEQ ID NO 4
<211> LENGTH: 247
<212> TYPE: DNA
<213> ORGANISM: Artificial sequence
<220> FEATURE:
<223> OTHER INFORMATION: Synthetic

<400> SEQUENCE: 4
tccctatcag tgatagagaa cgtatgaaga gtttactccc tatcagtgat agagaacgta        60
tgcagacttt actccctatc agtgatagag aacgtataag gagtttactc cctatcagtg       120
atagagaacg tatgaccagt ttactcccta tcagtgatag agaacgtatc tacagtttac       180
tccctatcag tgatagagaa cgtatatcca gtttactccc tatcagtgat agagaacgta       240
taagctt                                                               247

<210> SEQ ID NO 5
<211> LENGTH: 207
<212> TYPE: PRT
<213> ORGANISM: Artificial sequence
<220> FEATURE:
<223> OTHER INFORMATION: Synthetic

<400> SEQUENCE: 5

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80
```

```
Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205

<210> SEQ ID NO 6
<211> LENGTH: 206
<212> TYPE: PRT
<213> ORGANISM: Artificial sequence
<220> FEATURE:
<223> OTHER INFORMATION: Synthetic

<400> SEQUENCE: 6

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly
            195                 200                 205

<210> SEQ ID NO 7
<211> LENGTH: 66
<212> TYPE: PRT
<213> ORGANISM: Artificial sequence
<220> FEATURE:
```

<223> OTHER INFORMATION: Synthetic

<400> SEQUENCE: 7

```
Ala Tyr Ser Arg Ala Arg Thr Lys Asn Asn Tyr Gly Ser Thr Ile Glu
1               5                   10                  15

Gly Leu Leu Asp Leu Pro Asp Asp Pro Thr Asp Ala Leu Asp Asp
            20                  25                  30

Phe Asp Leu Asp Met Leu Pro Ala Asp Ala Leu Asp Asp Phe Asp Leu
            35                  40                  45

Asp Met Leu Pro Ala Asp Ala Leu Asp Asp Phe Asp Leu Asp Met Leu
        50                  55                  60

Pro Gly
65
```

<210> SEQ ID NO 8
<211> LENGTH: 272
<212> TYPE: PRT
<213> ORGANISM: Artificial sequence
<220> FEATURE:
<223> OTHER INFORMATION: Synthetic

<400> SEQUENCE: 8

```
Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ala Tyr
        195                 200                 205

Ser Arg Ala Arg Thr Lys Asn Asn Tyr Gly Ser Thr Ile Glu Gly Leu
    210                 215                 220

Leu Asp Leu Pro Asp Asp Pro Thr Asp Ala Leu Asp Asp Phe Asp
225                 230                 235                 240

Leu Asp Met Leu Pro Ala Asp Ala Leu Asp Asp Phe Asp Leu Asp Met
                245                 250                 255

Leu Pro Ala Asp Ala Leu Asp Asp Phe Asp Leu Asp Met Leu Pro Gly
            260                 265                 270
```

<210> SEQ ID NO 9
<211> LENGTH: 248
<212> TYPE: PRT
<213> ORGANISM: Artificial sequence
<220> FEATURE:
<223> OTHER INFORMATION: Synthetic

<400> SEQUENCE: 9

```
Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245
```

<210> SEQ ID NO 10
<211> LENGTH: 275
<212> TYPE: DNA
<213> ORGANISM: Artificial sequence
<220> FEATURE:
<223> OTHER INFORMATION: Synthetic

<400> SEQUENCE: 10

```
agtcattggg ttttccagc caatttataa aacgccatgt actttcccac cattgacgtc      60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctc                               275
```

<210> SEQ ID NO 11
<211> LENGTH: 315
<212> TYPE: DNA
<213> ORGANISM: Artificial sequence
<220> FEATURE:
<223> OTHER INFORMATION: Synthetic

<400> SEQUENCE: 11

```
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctctccct atcagtgata gagatctccc   300
tatcagtgat agaga                                                    315
```

<210> SEQ ID NO 12
<211> LENGTH: 288
<212> TYPE: DNA
<213> ORGANISM: Artificial sequence
<220> FEATURE:
<223> OTHER INFORMATION: Synthetic

<400> SEQUENCE: 12

```
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctcgttta gtgaaccg               288
```

<210> SEQ ID NO 13
<211> LENGTH: 220
<212> TYPE: DNA
<213> ORGANISM: Artificial sequence
<220> FEATURE:
<223> OTHER INFORMATION: Synthetic

<400> SEQUENCE: 13

```
tgctgatgcg gttttggcag tacaccaatg ggcgtggata gcggtttgac tcacgggat    60
ttccaagtct ccaccccatt gacgtcaatg ggagtttgtt ttggcaccaa atcaacggg   120
actttccaaa atgtcgtaat aaccccgccc cgttgacgca aatgggcggt aggcgtgtac   180
ggtgggaggt ctatataagc agagctcgtt tagtgaaccg                        220
```

<210> SEQ ID NO 14
<211> LENGTH: 220
<212> TYPE: DNA
<213> ORGANISM: Artificial sequence
<220> FEATURE:
<223> OTHER INFORMATION: Synthetic

<400> SEQUENCE: 14

```
tggtgatgcg gttttggcag tacatcaatg ggcgtggata gcggtttgac tcacgggat    60
ttccaagtct ccaccccatt gacgtcaatg ggagtttgtt ttggcaccaa atcaacggg   120
actttccaaa atgtcgtaac aactccgccc cattgacgca aatgggcggt aggcgtgtac   180
ggtgggaggt ctatataagc agagctcgtt tagtgaaccg                        220
```

```
<210> SEQ ID NO 15
<211> LENGTH: 247
<212> TYPE: DNA
<213> ORGANISM: Artificial sequence
<220> FEATURE:
<223> OTHER INFORMATION: Synthetic

<400> SEQUENCE: 15
tggtgatgcg gttttggcag tacatcaatg ggcgtggata gcggtttgac tcacggggat      60
ttccaagtct ccaccccatt gacgtcaatg ggagtttgtt ttggcaccaa aatcaacggg     120
actttccaaa atgtcgtaac aactccgccc cattgacgca aatgggcggt aggcgtgtac     180
ggtgggaggt ctatataagc agagctctcc ctatcagtga tagagatctc cctatcagtg     240
atagaga                                                               247

<210> SEQ ID NO 16
<211> LENGTH: 286
<212> TYPE: DNA
<213> ORGANISM: Artificial sequence
<220> FEATURE:
<223> OTHER INFORMATION: Synthetic

<400> SEQUENCE: 16
agtcattggg ttttccagc caatttataa aacgccatgt actttcccac cattgacgtc       60
aatgggctat tgaaactaat gcaacgtgac ctttaaacgg tactttccca tagctgatta    120
atgggaaagt accgttctcg agccaataca cgtcaatggg aagtgaaagg gcagccaaaa    180
cgtaacaccg ccccggtttt cccctggaaa ttccatattg gcacgcattc tattggctga    240
gctgcgttct acgtgggtat aagaggcgcg accagcgtcg gtaccg                   286

<210> SEQ ID NO 17
<211> LENGTH: 329
<212> TYPE: DNA
<213> ORGANISM: Artificial sequence
<220> FEATURE:
<223> OTHER INFORMATION: Synthetic

<400> SEQUENCE: 17
cggtccgaat ttcaaagtct ttttcctatt gacctacaag gttttcaaga atcatgttgt       60
aagcaactgt gttctgagga atctatgttt aaaaacccat ccgtggatct tggcccaggg    120
tccagagact gagctagcca cgccccggcc gcgccgcagc cactcccacg gcagttcaag    180
tgttaagtcc caaagaccgc gctctgtgca tgcgcagacc cgtccacagc tggctcctag    240
ccaacccggc cggacgagca cccggcgccg tcacgtgacg cacccaaccg gcgtcgacct    300
ataaaaggcc gggcgttgac gtcagcgtt                                      329

<210> SEQ ID NO 18
<211> LENGTH: 466
<212> TYPE: DNA
<213> ORGANISM: Artificial sequence
<220> FEATURE:
<223> OTHER INFORMATION: Synthetic

<400> SEQUENCE: 18
cggggttggg gttgcgcctt ttccaaggca gccctgggtt tgcgcaggga cgcggctgct      60
ctgggcgtgg ttccgggaaa cgcagcggcg ccgaccctgg gcctcgcaca ttcttcacgt    120
ccgttcgcag cgtcacccgg atcttcgccg ctacccttgt gggccccccg cgacgcttc     180 ctcgtccgcc cctaagtcgg gaaggttcct tgcggttcgc ggcgtgccgg acgtgacaaa    240
```

```
cggaagccgc acgtctcact agtaccctcg cagacggaca gcgccaggga gcaatggcag    300
cgcgccgacc gcgatgggct gtggccaata gcggctgctc agcagggcgc gccgagagca    360
gcggccggga aggggcggtg cgggaggcgg ggtgtggggc ggtagtgtgg gccctgttcc    420
tgcccgcgcg gtgttccgca ttctgcaagc ctccggagcg cacgtc                   466
```

<210> SEQ ID NO 19
<211> LENGTH: 494
<212> TYPE: DNA
<213> ORGANISM: Artificial sequence
<220> FEATURE:
<223> OTHER INFORMATION: Synthetic

<400> SEQUENCE: 19

```
atgacgtcga ggagaagttc cccaactttc ccgcctctca gcctttgaaa gaaagaaagg     60 ggaggggggca ggccgcgtgc agccgcgagc ggtgctgggc tccggctcca attccccatc   120
tcagtcgttc ccaaagtcct cctgtttcat ccaagcgtgt aagggtcccc gtccttgact    180
ccctagtgtc ctgctgccca cagtccagtc tgggaaccag caccgatca cctcccatcg    240 ggccaatctc agtcccttcc cccctacgtc ggggcccaca cgctcggtgc gtgcccagtt    300
gaaccaggcg gctgcggaaa aaaaaaagcg gggagaaagt agggcccggc tactagcggt    360
tttacgggcg cacgtagctc aggcctcaag accttgggct gggactggct gagcctggcg    420
ggaggcgggg tccgagtcac cgcctgccgc cgcgcccccg gtttctataa attgagcccg    480
cagcctcccg cttc                                                      494
```

<210> SEQ ID NO 20
<211> LENGTH: 80
<212> TYPE: DNA
<213> ORGANISM: Artificial sequence
<220> FEATURE:
<223> OTHER INFORMATION: Synthetic

<400> SEQUENCE: 20

```
ggccggagga gcacccgcgc cgtcacgtga cgtgcccaac cggcgtcgac ctataaaagg     60
ccgggcgttg acgtcagcgg                                                 80
```

<210> SEQ ID NO 21
<211> LENGTH: 503
<212> TYPE: DNA
<213> ORGANISM: Artificial sequence
<220> FEATURE:
<223> OTHER INFORMATION: Synthetic

<400> SEQUENCE: 21

```
cggggttggg gttgcgcctt ttccaaggca gccctgggtt tgcgcaggga cgcggctgct     60
ctgggcgtgg ttccgggaaa cgcagcggcg ccgaccctgg gcctcgcaca ttcttcacgt    120
ccgttcgcag cgtcacccgg atcttcgccg ctacccttgt gggcccccg gcgacgcttc     180 ctcgtccgcc cctaagtcgg gaaggttcct tgcggttcgc ggcgtgccgg acgtgacaaa    240
cggaagccgc acgactcact agtaccctcg cagacggaca gcgccaggga gcaatggcag    300
cgcgccgacc gcgatgggct gtggccaata gcggctgctc agcagggcgc gccgagagca    360
gcggccggga aggggcggtg cgggaggcgg ggtgtggggc ggtagtgtgg gccctgttcc    420
tgcccgcgcg gtgttccgca ttctgcaagc ctccggagcg cacgtcctct caggggacac    480
ccaagctgtc tagagccttt ttt                                            503
```

<210> SEQ ID NO 22
<211> LENGTH: 51
<212> TYPE: DNA
<213> ORGANISM: Artificial sequence
<220> FEATURE:
<223> OTHER INFORMATION: Synthetic

<400> SEQUENCE: 22
taggcgtgta cggtgggagg tctatataag cagagctcgt ttagtgaacc g        51

<210> SEQ ID NO 23
<211> LENGTH: 52
<212> TYPE: DNA
<213> ORGANISM: Artificial sequence
<220> FEATURE:
<223> OTHER INFORMATION: Synthetic

<400> SEQUENCE: 23
ggctgagctg cgttctacgt gggtataaga ggcgcgacca gcgtcggtac cg        52

<210> SEQ ID NO 24
<211> LENGTH: 51
<212> TYPE: DNA
<213> ORGANISM: Artificial sequence
<220> FEATURE:
<223> OTHER INFORMATION: Synthetic

<400> SEQUENCE: 24
taggcgtgcc ctatgggcgg tctatataag cagagcccgt ttagtgaacc g        51

<210> SEQ ID NO 25
<211> LENGTH: 151
<212> TYPE: DNA
<213> ORGANISM: Artificial sequence
<220> FEATURE:
<223> OTHER INFORMATION: Synthetic

<400> SEQUENCE: 25
taggcgtgcc ctatgggcgg tctatataag cagagcccgt ttagtgaacc gtcagatcgc        60
ctggagaggc catccaacgt ctctggggtg agacagcttg cttgttcttt ttgcagaagc        120
tcagaataaa cgctcaactt tggccgccac c                                      151

<210> SEQ ID NO 26
<211> LENGTH: 334
<212> TYPE: DNA
<213> ORGANISM: Artificial sequence
<220> FEATURE:
<223> OTHER INFORMATION: Synthetic

<400> SEQUENCE: 26
tccctatcag tgatagagat gcttctccac tcactatccc tatcagtgat agagagtaaa        60
ctcttcatag gttccctatc agtgatagag agtctagtct gcataccttc cctatcagtg        120
atagagagac aactccttat aggttcccta tcagtgatag agagtaaact ggtcatacct        180
tccctatcag tgatagagag taaactgtag ataccttccc tatcagtgat agagagtaaa        240
ctggatatag gttccctatc agtgatagag aaagcttata ccttaggcgt gccctatggg        300
cggtctatat aagcagagcc cgtttagtga accg                                   334

<210> SEQ ID NO 27
<211> LENGTH: 434
<212> TYPE: DNA
<213> ORGANISM: Artificial sequence
<220> FEATURE:

<223> OTHER INFORMATION: Synthetic

<400> SEQUENCE: 27

| tccctatcag tgatagagat gcttctccac tcactatccc tatcagtgat agagagtaaa | 60 |
| ctcttcatag gttccctatc agtgatagag agtctagtct gcataccttc cctatcagtg | 120 |
| atagagagac aactccttat aggttcccta tcagtgatag agagtaaact ggtcatacct | 180 |
| tccctatcag tgatagagag taaactgtag ataccttccc tatcagtgat agagagtaaa | 240 |
| ctggatatag gttccctatc agtgatagag aaagcttata ccttaggcgt gccctatggg | 300 |
| cggtctatat aagcagagcc cgtttagtga accgtcagat cgcctggaga ggccatccaa | 360 |
| cgtctctggg gtgagacagc ttgcttgttc tttttgcaga agctcagaat aaacgctcaa | 420 |
| ctttggccgc cacc | 434 |

<210> SEQ ID NO 28
<211> LENGTH: 173
<212> TYPE: DNA
<213> ORGANISM: Artificial sequence
<220> FEATURE:
<223> OTHER INFORMATION: Synthetic

<400> SEQUENCE: 28

| tagtcccgcc cctaactccg cccatcccgc ccctaactcc gcccagttcc gcccattctc | 60 |
| cgccccatcg ctgactaatt ttttttattt atgcagaggc cgaggccgcc tcggcctctg | 120 |
| agctattcca gaagtagtga ggaggctttt ttggaggcct aggcttttgc aaa | 173 |

<210> SEQ ID NO 29
<211> LENGTH: 57
<212> TYPE: DNA
<213> ORGANISM: Artificial sequence
<220> FEATURE:
<223> OTHER INFORMATION: Synthetic

<400> SEQUENCE: 29

| agcttgcttg ttcttttgc agaagctcag aataaacgct caactttggc cgccacc | 57 |

<210> SEQ ID NO 30
<211> LENGTH: 100
<212> TYPE: DNA
<213> ORGANISM: Artificial sequence
<220> FEATURE:
<223> OTHER INFORMATION: Synthetic

<400> SEQUENCE: 30

| tcagatcgcc tggagaggcc atccaacgtc tctggggtga gacagcttgc ttgttctttt | 60 |
| tgcagaagct cagaataaac gctcaacttt ggccgccacc | 100 |

<210> SEQ ID NO 31
<211> LENGTH: 110
<212> TYPE: DNA
<213> ORGANISM: Artificial sequence
<220> FEATURE:
<223> OTHER INFORMATION: Synthetic

<400> SEQUENCE: 31

| tcgtcgacga gctcgtttag tgaaccgtca gatcgccgtc tctggggtga gacagcttgc | 60 |
| ttgttctttt tgcagaagct cagaataaac gctcaacttt ggccgccacc | 110 |

<210> SEQ ID NO 32
<211> LENGTH: 236

<212> TYPE: PRT
<213> ORGANISM: Artificial sequence
<220> FEATURE:
<223> OTHER INFORMATION: Synthetic

<400> SEQUENCE: 32

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
        35                  40                  45

Tyr Ile Cys Thr Thr Gly Asp Leu Pro Val Pro Trp Ala Thr Leu Val
    50                  55                  60

Ser Thr Leu Ser Tyr Gly Val Gln Cys Phe Ala Lys Tyr Pro Ser His
65                  70                  75                  80

Ile Lys Asp Phe Phe Lys Ser Ala Met Pro Glu Gly Tyr Thr Gln Glu
                85                  90                  95

Arg Thr Ile Ser Phe Glu Gly Asp Gly Val Tyr Lys Thr Arg Ala Met
            100                 105                 110

Val Thr Tyr Glu Arg Gly Ser Ile Tyr Asn Arg Val Thr Leu Thr Gly
        115                 120                 125

Glu Asn Phe Lys Lys Asp Gly His Ile Leu Arg Lys Asn Val Ala Phe
    130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175

Glu Lys Leu Val Thr Lys Cys Ser Gln Met Asn Arg Pro Leu Ala Gly
            180                 185                 190

Ser Ala Ala Val His Ile Pro Arg Tyr His His Ile Thr Tyr His Thr
        195                 200                 205

Lys Leu Ser Lys Asp Arg Asp Glu Arg Arg Asp His Met Cys Leu Val
    210                 215                 220

Glu Val Val Lys Ala Val Asp Leu Asp Thr Tyr Gln
225                 230                 235
```

<210> SEQ ID NO 33
<211> LENGTH: 503
<212> TYPE: DNA
<213> ORGANISM: Artificial sequence
<220> FEATURE:
<223> OTHER INFORMATION: Synthetic

<400> SEQUENCE: 33

```
cggggttggg gttgcgcctt ttccaaggca gccctgggtt tgcgcaggga cgcggctgct      60
ctgggcgtgg ttccgggaaa cgcagcggcg ccgaccctgg gcctcgcaca ttcttcacgt     120
ccgttcgcag cgtcacccgg atcttcgccg ctacccttgt gggcccccg gcgacgcttc      180 ctcgtccgcc cctaagtcgg gaaggttcct tgcggttcgc ggcgtgccgg acgtgacaaa     240
cggaagccgc acgactcact agtaccctcg cagacggaca cgccaggga gcaatggcag     300 cgcgccgacc gcgatgggct gtggccaata gcggctgctc agcagggcgc gccgagagca     360
gcggccggga aggggcggtg cgggaggcgg ggtgtgggc ggtagtgtgg gccctgttcc     420
tgcccgcgcg gtgttccgca ttctgcaagc ctccggagcg cacgtcctct cagggacac      480 ccaagctgtc tagagccttc tat                                              503
```

<210> SEQ ID NO 34
<211> LENGTH: 503
<212> TYPE: DNA
<213> ORGANISM: Artificial sequence
<220> FEATURE:
<223> OTHER INFORMATION: Synthetic

<400> SEQUENCE: 34

```
cggggttggg gttgcgcctt ttccaaggca gccctgggtt tgcgcaggga cgcggctgct     60
ctgggcgtgg ttccgggaaa cgcagcggcg ccgaccctgg gcctcgcaca ttcttcacgt    120
ccgttcgcag cgtcacccgg atcttcgccg ctacccttgt gggcccccccg gcgacgcttc   180 ctcgtccgcc cctaagtcgg gaaggttcct tgcggttcgc ggcgtgccgg acgtgacaaa    240
cggaagccgc acgactcact agtaccctcg cagacggaca gcgccaggga gcaatggcag    300
cgcgccgacc gcgatgggct gtggccaata gcggctgctc agcagggcgc gccgagagca    360
gcggccggga aggggcggtg cgggaggcgg ggtgtgggc ggtagtgtgg gccctgttcc     420
tgcccgcgcg gtgttccgca ttctgcaagc ctccggagcg cacgtcctct caggggacac    480
ccaagctgtc tagagcctcc ttt                                             503
```

<210> SEQ ID NO 35
<211> LENGTH: 13
<212> TYPE: DNA
<213> ORGANISM: Artificial sequence
<220> FEATURE:
<223> OTHER INFORMATION: Synthetic

<400> SEQUENCE: 35

```
gtttagtgaa ccg                                                        13
```

<210> SEQ ID NO 36
<211> LENGTH: 207
<212> TYPE: DNA
<213> ORGANISM: Artificial sequence
<220> FEATURE:
<223> OTHER INFORMATION: Synthetic

<400> SEQUENCE: 36

```
tggtgatgcg gttttggcag tacatcaatg ggcgtggata gcggtttgac tcacggggat     60
ttccaagtct ccaccccatt gacgtcaatg ggagtttgtt ttggcaccaa aatcaacggg    120
actttccaaa atgtcgtaac aactccgccc cattgacgca aatgggcggt aggcgtgtac    180
ggtgggaggt ctatataagc agagctc                                         207
```

<210> SEQ ID NO 37
<211> LENGTH: 503
<212> TYPE: DNA
<213> ORGANISM: Artificial sequence
<220> FEATURE:
<223> OTHER INFORMATION: Synthetic

<400> SEQUENCE: 37

```
cggggttggg gttgcgcctt ttccaaggca gccctgggtt tgcgcaggga cgcggctgct     60
ctgggcgtgg ttccgggaaa cgcagcggcg ccgaccctgg gcctcgcaca ttcttcacgt    120
ccgttcgcag cgtcacccgg atcttcgccg ctacccttgt gggcccccccg gcgacgcttc   180 ctcgtccgcc cctaagtcgg gaaggttcct tgcggttcgc ggcgtgccgg acgtgacaaa    240
cggaagccgc acgtctcact agtaccctcg cagacggaca gcgccaggga gcaatggcag    300
```

```
cgcgccgacc gcgatgggct gtggccaata gcggctgctc agcagggcgc gccgagagca    360
gcggccggga aggggcggtg cgggaggcgg ggtgtggggc ggtagtgtgg gccctgttcc    420
tgcccgcgcg gtgttccgca ttctgcaagc ctccggagcg cacgtcctct cagggacac     480 ccaagctgtc tagagccgcc acc                                            503
```

<210> SEQ ID NO 38
<211> LENGTH: 50
<212> TYPE: DNA
<213> ORGANISM: Artificial sequence
<220> FEATURE:
<223> OTHER INFORMATION: Synthetic

<400> SEQUENCE: 38

```
taggcgtgta cggtgggcgc ctataaaagc agagctcgtt tagtgaaccg                50
```

<210> SEQ ID NO 39
<211> LENGTH: 144
<212> TYPE: DNA
<213> ORGANISM: Artificial sequence
<220> FEATURE:
<223> OTHER INFORMATION: Synthetic

<400> SEQUENCE: 39

```
tcagatcgcc tggagaggcc atccacgctg ttttgacctc catagtggac accgggaccg    60
atccagcctc cgtctctggg gtgagacagc ttgcttgttc tttttgcaga agctcagaat   120
aaacgctcaa ctttggccgc cacc                                          144
```

<210> SEQ ID NO 40
<211> LENGTH: 42
<212> TYPE: PRT
<213> ORGANISM: Artificial sequence
<220> FEATURE:
<223> OTHER INFORMATION: Synthetic

<400> SEQUENCE: 40

Gly Pro Thr Asp Ala Leu Asp Asp Phe Asp Leu Asp Met Leu Pro Ala
1               5                   10                  15

Asp Ala Leu Asp Asp Phe Asp Leu Asp Met Leu Pro Ala Asp Ala Leu
            20                  25                  30

Asp Asp Phe Asp Leu Asp Met Leu Pro Gly
        35                  40

<210> SEQ ID NO 41
<211> LENGTH: 14
<212> TYPE: DNA
<213> ORGANISM: Artificial sequence
<220> FEATURE:
<223> OTHER INFORMATION: Synthetic

<400> SEQUENCE: 41

```
ccytttbmct gcca                                                       14
```

<210> SEQ ID NO 42
<211> LENGTH: 14
<212> TYPE: DNA
<213> ORGANISM: Artificial sequence
<220> FEATURE:
<223> OTHER INFORMATION: Synthetic

<400> SEQUENCE: 42

```
tggcagkvaa argg                                                       14
```

<210> SEQ ID NO 43
<211> LENGTH: 64
<212> TYPE: DNA
<213> ORGANISM: Artificial sequence
<220> FEATURE:
<223> OTHER INFORMATION: Synthetic

<400> SEQUENCE: 43
atcacgcatg ggatacgtcg tggcagtaaa agggcttaaa tgccaacgac gcgtcccata    60
cgtt                                                                64

<210> SEQ ID NO 44
<211> LENGTH: 82
<212> TYPE: DNA
<213> ORGANISM: Artificial sequence
<220> FEATURE:
<223> OTHER INFORMATION: Synthetic

<400> SEQUENCE: 44
atgacgcatg ggatacgtcg tggcagtaaa agggcttaaa tgccaacgac gcgtcccata    60
cgttgttggc attttaagtc tt                                             82

<210> SEQ ID NO 45
<211> LENGTH: 106
<212> TYPE: DNA
<213> ORGANISM: Artificial sequence
<220> FEATURE:
<223> OTHER INFORMATION: Synthetic

<400> SEQUENCE: 45
cctgggtaaa ctaaaagtcc cctcgaggaa aggcccctaa agtgaaacag tgcaaaacgt    60
tcaaaaactg tctggcaata caagttccac tttgggacaa atcggc                   106

<210> SEQ ID NO 46
<211> LENGTH: 105
<212> TYPE: DNA
<213> ORGANISM: Artificial sequence
<220> FEATURE:
<223> OTHER INFORMATION: Synthetic

<400> SEQUENCE: 46
cctgggtaaa ctaaaagtcc cctcgaggaa aggcccctaa agtgaaacag tgcaaaacgt    60
tcaaaaactg tctggcaata caagttccac tttgaccaaa acggc                    105

<210> SEQ ID NO 47
<211> LENGTH: 589
<212> TYPE: PRT
<213> ORGANISM: Artificial sequence
<220> FEATURE:
<223> OTHER INFORMATION: Synthetic

<400> SEQUENCE: 47

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Thr Glu Glu Ser Trp Cys Ser Ser
        35                  40                  45

Ser Thr Val Ser Ala Leu Glu Glu Pro Met Gly Val Asp Glu Asp Val
    50                  55                  60

Asp Asp Leu Glu Asp Gln Glu Ala Gly Asp Arg Ala Asp Ala Ala Ala

```
                65                  70                  75                  80
Gly Gly Glu Pro Ala Trp Gly Pro Pro Cys Asn Phe Pro Pro Glu Ile
                    85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
                115                 120                 125

Asp Met Val Leu Tyr Thr Asn Val Tyr Ala Glu Gln Tyr Leu Thr Gln
            130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                    165                 170                 175

Ile Lys Ala Asn Ser Leu Glu Ser Tyr Trp Asp Thr Thr Val Leu
                180                 185                 190

Ser Ile Pro Val Phe Ser Ala Thr Met Ser Arg Asn Arg Tyr Gln Leu
                195                 200                 205

Leu Leu Arg Phe Leu His Phe Asn Asn Asn Ala Thr Ala Val Pro Pro
            210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                    245                 250                 255

Cys Ile Asp Glu Ser Leu Leu Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Gly Tyr Thr Ser Tyr Phe Leu Ile Tyr Glu
            290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                    325                 330                 335

Gly Phe His Leu Tyr Val Asp Asn Phe Tyr Ser Ser Ile Pro Leu Phe
                340                 345                 350

Thr Ala Leu Tyr Cys Leu Asp Thr Pro Ala Cys Gly Thr Ile Asn Arg
            355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
                    420                 425                 430

Cys Ser Lys Glu Tyr Ser Lys Tyr Met Gly Gly Val Asp Arg Thr Asp
                435                 440                 445

Gln Leu Gln His Tyr Tyr Asn Ala Thr Arg Lys Thr Arg Ala Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                    485                 490                 495
```

-continued

```
Tyr Gln Leu Gln Ile Leu Pro Ala Leu Leu Phe Gly Gly Val Glu Glu
                500                 505                 510

Gln Thr Val Pro Glu Met Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr
                580                 585

<210> SEQ ID NO 48
<211> LENGTH: 589
<212> TYPE: PRT
<213> ORGANISM: Artificial sequence
<220> FEATURE:
<223> OTHER INFORMATION: Synthetic

<400> SEQUENCE: 48

Met Ala Lys Arg Phe Tyr Ser Ala Glu Glu Ala Ala His Cys Met
1               5                   10                  15

Ala Pro Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asn Thr Thr Thr Val Leu
                180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Asp His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Arg Phe Arg
                260                 265                 270
```

Gln Tyr Ile Pro Ser Lys Arg Ala Arg Tyr Gly Ile Lys Phe Tyr Lys
        275                 280                 285

Leu Cys Glu Ser Ser Gly Tyr Thr Ser Tyr Phe Leu Ile Tyr Glu
    290                 295                 300

Gly Lys Asp Ser Lys Leu Asp Pro Pro Gly Cys Pro Asp Leu Thr
305                 310                 315                 320

Val Ser Gly Lys Ile Val Trp Glu Leu Ile Ser Pro Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
        355                 360                 365

Thr Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Ser Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Leu Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr
            580                 585

<210> SEQ ID NO 49
<211> LENGTH: 589
<212> TYPE: PRT
<213> ORGANISM: Artificial sequence
<220> FEATURE:
<223> OTHER INFORMATION: Synthetic

<400> SEQUENCE: 49

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
 50                  55                  60

Asp Asp Leu Glu Asp Gln Glu Ala Gly Asp Arg Ala Asp Ala Ala Ala
 65                  70                  75                  80

Gly Gly Glu Pro Ala Trp Gly Pro Pro Cys Asn Phe Pro Pro Glu Ile
                 85                  90                  95

Pro Pro Phe Thr Thr Val Pro Gly Val Lys Val Asp Thr Ser Asn Tyr
             100                 105                 110

Glu Pro Ile Asn Phe Phe Gln Leu Phe Met Thr Glu Ala Ile Leu Gln
             115                 120                 125

Asp Met Val Leu Tyr Thr Asn Val Tyr Ala Glu Gln Tyr Leu Thr Gln
             130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                 165                 170                 175

Ile Lys Ala Asn Ser Leu Glu Ser Tyr Trp Asp Thr Thr Val Leu
                 180                 185                 190

Ser Ile Pro Val Phe Ser Ala Thr Met Ser Arg Asn Arg Tyr Gln Leu
             195                 200                 205

Leu Leu Arg Phe Leu His Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                 245                 250                 255

Cys Ile Asp Glu Ser Leu Leu Leu Phe Lys Gly Arg Leu Gln Phe Arg
             260                 265                 270

Gln Tyr Ile Pro Ser Lys Arg Ala Arg Tyr Gly Ile Lys Phe Tyr Lys
             275                 280                 285

Leu Cys Glu Ser Ser Ser Gly Tyr Thr Ser Tyr Phe Leu Ile Tyr Glu
             290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                 325                 330                 335

Gly Phe His Leu Tyr Val Asp Asn Phe Tyr Ser Ser Ile Pro Leu Phe
             340                 345                 350

Thr Ala Leu Tyr Cys Leu Asp Thr Pro Ala Cys Gly Thr Ile Asn Arg
             355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                 405                 410                 415

Val Ile Arg Glu Gln Arg Val Gly Arg Pro Lys Asn Lys Pro Leu
             420                 425                 430

Cys Ser Lys Glu Tyr Ser Lys Tyr Met Gly Gly Val Asp Arg Thr Asp
             435                 440                 445

Gln Leu Gln His Tyr Tyr Asn Ala Thr Arg Lys Thr Arg Ala Trp Tyr
450                 455                 460

```
Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr
                580                 585

<210> SEQ ID NO 50
<211> LENGTH: 589
<212> TYPE: PRT
<213> ORGANISM: Artificial sequence
<220> FEATURE:
<223> OTHER INFORMATION: Synthetic

<400> SEQUENCE: 50

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
    130                 135                 140

Val Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Asn Ile Pro Val Phe Ser Ala Thr Met Ser Arg Asn Arg Tyr Gln Leu
        195                 200                 205

Leu Leu Arg Phe Leu Glu Phe Asn Asn Glu Ala Thr Ala Val Pro Pro
    210                 215                 220

Asp Gln Pro Gly His Asp Arg Leu His Lys Leu Arg Pro Leu Ile Asp
225                 230                 235                 240
```

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr
            580                 585

<210> SEQ ID NO 51
<211> LENGTH: 589
<212> TYPE: PRT
<213> ORGANISM: Artificial sequence
<220> FEATURE:
<223> OTHER INFORMATION: Synthetic

<400> SEQUENCE: 51

Met Ala Lys Arg Phe Tyr Ser Ala Glu Glu Ala Ala His Cys Met
1               5                   10                  15

```
Ala Ser Ser Gln Glu Glu Phe Ser Gly Ser Asp Ser Glu Tyr Val Pro
            20                  25                  30
Pro Ala Ser Glu Ser Asp Ser Ser Thr Glu Glu Ser Trp Cys Ser Ser
        35                  40                  45
Ser Thr Val Ser Ala Leu Glu Glu Pro Met Glu Val Asp Glu Asp Val
    50                  55                  60
Asp Asp Leu Glu Asp Gln Glu Ala Gly Asp Arg Ala Asp Ala Ala Ala
65                  70                  75                  80
Gly Gly Glu Pro Ala Trp Gly Pro Pro Cys Asn Phe Pro Pro Glu Ile
                85                  90                  95
Pro Pro Phe Thr Thr Val Pro Gly Val Lys Val Asp Thr Ser Asn Phe
            100                 105                 110
Glu Pro Ile Asn Phe Phe Gln Leu Phe Met Thr Glu Ala Ile Leu Gln
        115                 120                 125
Asp Met Val Leu Tyr Thr Asn Val Tyr Ala Glu Gln Tyr Leu Thr Gln
    130                 135                 140
Asn Pro Leu Thr Arg Tyr Ala Arg Ala His Ala Trp His Pro Thr Asp
145                 150                 155                 160
Ile Ala Glu Met Lys Arg Phe Val Gly Leu Thr Leu Ala Met Gly Leu
                165                 170                 175
Ile Lys Ala Asn Ser Leu Glu Ser Tyr Trp Asp Thr Thr Val Leu
            180                 185                 190
Ser Ile Pro Val Phe Gly Ala Thr Met Ser Arg Asn Arg Tyr Gln Leu
        195                 200                 205
Leu Leu Arg Phe Leu His Phe Asn Asn Asn Ala Thr Ala Val Pro Pro
    210                 215                 220
Asp Gln Pro Gly His Asp Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Leu Leu Phe Lys Gly Arg Leu Gln Phe Lys
            260                 265                 270
Gln Tyr Ile Pro Ser Lys Arg Ala Arg Tyr Gly Ile Lys Phe Tyr Lys
        275                 280                 285
Leu Cys Glu Ser Ser Ser Gly Tyr Thr Ser Tyr Phe Leu Ile Tyr Glu
    290                 295                 300
Gly Lys Asp Ser Lys Leu Asp Pro Pro Gly Cys Pro Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Cys Leu Asn Thr Pro Ala Cys Gly Thr Ile Asn Arg
        355                 360                 365
Asn Arg Lys Gly Leu Pro Arg Ala Leu Leu Asp Lys Leu Asn Arg
    370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Pro Pro Lys Asn Lys Pro Leu
            420                 425                 430
Cys Ser Lys Glu Tyr Ser Lys Tyr Met Gly Gly Val Asp Arg Thr Asp
```

```
                    435                 440                 445
Gln Leu Gln His Tyr Tyr Asn Ala Thr Arg Lys Thr Arg His Trp Tyr
    450                 455                 460

Lys Lys Val Gly Val Tyr Leu Ile Gln Met Ala Leu Arg Asn Ser Tyr
465                 470                 475                 480

Ile Val Tyr Lys Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Asp Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 52
<211> LENGTH: 589
<212> TYPE: PRT
<213> ORGANISM: Artificial sequence
<220> FEATURE:
<223> OTHER INFORMATION: Synthetic

<400> SEQUENCE: 52

Met Ala Lys Arg Phe Tyr Ser Ala Glu Glu Ala Ala His Cys Met
1               5                   10                  15

Ala Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
    130                 135                 140

Asn Pro Leu Thr Arg Tyr Ala Arg Ala His Ala Trp His Pro Thr Asp
145                 150                 155                 160

Ile Cys Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Gly Ala Thr Met Ser Arg Asn Arg Tyr Gln Leu
        195                 200                 205

Leu Leu Arg Phe Leu His Phe Asn Asn Asn Ala Thr Ala Val Pro Pro
```

```
            210                 215                 220
Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Thr Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Val Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Asp Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585
```

<210> SEQ ID NO 53
<211> LENGTH: 589
<212> TYPE: PRT
<213> ORGANISM: Artificial sequence
<220> FEATURE:
<223> OTHER INFORMATION: Synthetic

<400> SEQUENCE: 53

```
Met Ala Lys Arg Phe Tyr Ser Ala Glu Glu Ala Ala His Cys Met
1               5                   10                  15

Ala Ser Ser Glu Gln Thr Ser Gly Ser Asp Ser Glu Tyr Val Pro
            20                  25                  30

Pro Ala Ser Glu Ser Asp Ser Thr Glu Glu Ser Trp Cys Ser Ser
            35                  40                  45

Ser Thr Val Ser Ala Leu Glu Glu Pro Met Gly Val Asp Glu Asp Val
    50                  55                  60

Asp Asp Leu Glu Asp Gln Glu Ala Gly Asp Arg Ala Asp Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
            130                 135                 140

Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Ile Glu Ser Tyr Trp Asp Thr Thr Val Leu
                180                 185                 190

Ser Ile Pro Val Phe Gly Ala Thr Met Ser Arg Asn Arg Tyr Gln Leu
            195                 200                 205

Leu Leu Arg Phe Leu His Phe Asn Asn Asn Ala Thr Ala Val Pro Pro
            210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
            290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
            355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415
```

Val Ile Arg Glu Gln Arg Val Gly Arg Lys Pro Lys Asn Lys Pro Leu
            420                 425                 430

Cys Ser Lys Glu Tyr Ser Lys Tyr Met Gly Gly Val Asp Arg Thr Asp
            435                 440                 445

Gln Leu Gln His Tyr Tyr Asn Ala Thr Arg Lys Thr Arg His Trp Tyr
        450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
        530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 54
<211> LENGTH: 589
<212> TYPE: PRT
<213> ORGANISM: Artificial sequence
<220> FEATURE:
<223> OTHER INFORMATION: Synthetic

<400> SEQUENCE: 54

Met Ala Lys Arg Phe Tyr Ser Ala Glu Glu Ala Ala His Cys Ser
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
        50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
130                 135                 140

Asn Pro Leu Thr Arg Gly Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Gly Ala Thr Met Ser Arg Asn Arg Tyr Gln Leu
            195                 200                 205

Leu Leu Arg Phe Leu His Phe Asn Asn Asn Ala Thr Ala Val Pro Pro
        210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Met Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Thr Gly Tyr Thr Ser Tyr Phe Leu Ile Tyr Glu
        290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ile Pro Leu Phe
                340                 345                 350 Phe

Thr Ala Leu Tyr Cys Leu Asn Thr Pro Ala Cys Gly Thr Ile Asn Arg
            355                 360                 365

Asn Arg Lys Gly Leu Pro Arg Ala Leu Leu Asp Lys Lys Leu Asn Arg
        370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Val Glu Glu
            500                 505                 510 Glu

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 55
<211> LENGTH: 589

```
<212> TYPE: PRT
<213> ORGANISM: Artificial sequence
<220> FEATURE:
<223> OTHER INFORMATION: Synthetic

<400> SEQUENCE: 55

Met Ala Lys Arg Phe Tyr Ser Ala Glu Ala Ala His Cys Ser
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
50                  55                  60

Asp Asp Leu Glu Asp Gln Glu Ala His Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
130                 135                 140

Asn Pro Leu Thr Arg Gly Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Ile Glu Ser Tyr Trp Asp Thr Thr Thr Val Leu
            180                 185                 190

Ser Ile Pro Val Phe Gly Ala Thr Met Ser Arg Asn Arg Tyr Gln Leu
        195                 200                 205

Leu His Arg Phe Leu His Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Met Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Thr Gly Tyr Thr Ser Tyr Phe Leu Ile Tyr Glu
290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
        355                 360                 365

Asn Arg Lys Gly Leu Pro Arg Ala Leu Leu Asp Lys Lys Leu Asn Arg
370                 375                 380
```

Gly Glu Thr Tyr Ala Leu Arg Lys Asn Glu Leu Ala Ile Lys Phe
385                 390                 395                 400

Phe Asp Lys Lys Asn Val Phe Met Leu Thr Ser Ile His Asp Glu Ser
            405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Val Asp Arg Thr Asp
            435                 440                 445

Gln Leu Gln His Tyr Tyr Asn Ala Thr Arg Lys Thr Arg His Trp Tyr
        450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Ser Val Ala Arg Leu Ile
            515                 520                 525

Gly Lys His Phe Ile Asp Thr Leu Pro Pro Thr Pro Gly Lys Gln Arg
530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 56
<211> LENGTH: 589
<212> TYPE: PRT
<213> ORGANISM: Artificial sequence
<220> FEATURE:
<223> OTHER INFORMATION: Synthetic

<400> SEQUENCE: 56

Met Ala Lys Arg Phe Tyr Ser Ala Glu Glu Ala Ala His Cys Ser
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
    130                 135                 140

Asn Pro Leu Thr Arg Gly Ala Arg Ala His Ala Trp His Pro Thr Asp
145                 150                 155                 160

```
Ile Ala Glu Met Lys Arg Phe Val Gly Leu Thr Leu Ala Met Gly Leu
                165                 170                 175
Ile Lys Ala Asn Ser Ile Glu Ser Tyr Trp Asp Thr Thr Thr Val Leu
            180                 185                 190
Ser Ile Pro Val Phe Gly Ala Thr Met Ser Arg Asn Arg Tyr Gln Leu
        195                 200                 205
Leu Leu Arg Phe Leu His Phe Asn Asn Asn Ala Thr Ala Val Pro Pro
    210                 215                 220
Asp Gln Pro Gly His Asp Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Met Leu Phe Lys Gly Arg Leu Gln Phe Arg
            260                 265                 270
Gln Tyr Ile Pro Ser Lys Arg Ala Arg Tyr Gly Ile Lys Phe Tyr Lys
        275                 280                 285
Leu Cys Glu Ser Ser Thr Gly Tyr Thr Ser Tyr Phe Leu Ile Tyr Glu
    290                 295                 300
Gly Lys Asp Ser Lys Leu Asp Pro Pro Gly Cys Pro Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Cys Leu Asn Thr Pro Ala Cys Gly Thr Ile Asn Arg
        355                 360                 365
Asn Arg Lys Gly Leu Pro Arg Ala Leu Leu Asp Lys Lys Leu Asn Arg
    370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Pro Pro Lys Asn Lys Pro Leu
            420                 425                 430
Cys Ser Lys Glu Tyr Ser Lys Tyr Met Gly Gly Val Asp Arg Thr Asp
        435                 440                 445
Gln Leu Gln His Tyr Tyr Asn Ala Thr Arg Lys Thr Arg His Trp Tyr
    450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
            500                 505                 510
Gln Thr Val Pro Glu Met Pro Asp Ser Asp Asn Val Ala Arg Leu Ile
        515                 520                 525
Gly Lys His Phe Ile Asp Thr Leu Pro Pro Thr Pro Gly Lys Gln Arg
    530                 535                 540
Pro Gln Lys Gly Cys Lys Val Cys Arg Lys Arg Gly Ile Arg Arg Asp
545                 550                 555                 560
Thr Arg Tyr Tyr Cys Pro Lys Cys Pro Arg Asn Pro Gly Leu Cys Arg
                565                 570                 575
Lys Pro Cys Phe Glu Ile Tyr His Thr Gln Leu His Tyr
```

<210> SEQ ID NO 57
<211> LENGTH: 589
<212> TYPE: PRT
<213> ORGANISM: Artificial sequence
<220> FEATURE:
<223> OTHER INFORMATION: Synthetic

<400> SEQUENCE: 57

```
Met Ala Lys Arg Phe Tyr Ser Ala Glu Glu Ala Ala His Cys Ser
1               5                   10                  15

Ala Ser Ser Ser Glu Gln Phe Ser Gly Ser Asp Ser Glu Tyr Val Pro
            20                  25                  30

Pro Ala Ser Glu Ser Asp Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140

Asn Pro Leu Thr Arg Gly Ala Arg Ala His Ala Trp Tyr Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Ile Glu Ser Tyr Trp Asp Thr Thr Thr Val Leu
            180                 185                 190

Ser Ile Pro Val Phe Gly Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Met Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285

Leu Cys Glu Ser Ser Thr Gly Tyr Thr Ser Tyr Phe Leu Ile Tyr Glu
    290                 295                 300

Gly Lys Asp Ser Lys Leu Asp Pro Pro Gly Cys Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
```

355                 360                 365
Asn Arg Lys Gly Leu Pro Arg Ala Leu Leu Asp Lys Lys Leu Asn Arg
            370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Gly Asp
                435                 440                 445

Gln Leu Gln His Tyr Tyr Asn Ala Thr Arg Lys Thr Arg His Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Ser Asp Asn Val Ala Arg Leu Ile
            515                 520                 525

Gly Lys His Phe Ile Asp Thr Leu Pro Pro Thr Pro Gly Lys Gln Arg
            530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 58
<211> LENGTH: 589
<212> TYPE: PRT
<213> ORGANISM: Artificial sequence
<220> FEATURE:
<223> OTHER INFORMATION: Synthetic

<400> SEQUENCE: 58

Met Ala Lys Arg Phe Tyr Ser Ala Glu Glu Ala Ala His Cys Ser
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln

-continued

```
            130                 135                 140
Asn Pro Leu Thr Arg Gly Ala Arg Ala His Ala Trp His Pro Thr Asp
145                 150                 155                 160
Ile Ala Glu Met Lys Arg Phe Val Gly Leu Thr Leu Ala Met Gly Leu
                165                 170                 175
Ile Lys Ala Asn Ser Ile Glu Ser Tyr Trp Asp Thr Thr Val Leu
            180                 185                 190
Ser Ile Pro Val Phe Gly Ala Thr Met Ser Arg Asn Arg Tyr Gln Leu
            195                 200                 205
Leu Leu Arg Phe Leu His Phe Asn Asn Asn Ala Thr Ala Val Pro Pro
            210                 215                 220
Asp Gln Pro Gly His Asp Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Met Leu Phe Lys Gly Arg Leu Gln Phe Arg
                260                 265                 270
Gln Tyr Ile Pro Ser Lys Arg Ala Arg Tyr Gly Ile Lys Phe Tyr Lys
            275                 280                 285
Leu Cys Glu Ser Ser Thr Gly Tyr Met Ser Tyr Phe Leu Ile Tyr Glu
            290                 295                 300
Gly Lys Asp Ser Lys Leu Asp Pro Pro Gly Cys Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Cys Leu Asn Thr Pro Ala Cys Gly Thr Ile Asn Arg
            355                 360                 365
Asn Arg Lys Gly Leu Pro Arg Ala Leu Leu Asp Lys Lys Leu Asn Arg
370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Lys Pro Lys Asn Lys Pro Leu
                420                 425                 430
Cys Ser Lys Glu Tyr Ser Lys Tyr Met Gly Gly Val Asp Arg Thr Asp
                435                 440                 445
Gln Leu Gln His Tyr Tyr Asn Ala Thr Arg Lys Thr Arg His Trp Tyr
            450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
            500                 505                 510
Gln Thr Val Pro Glu Met Pro Pro Ser Asp Ser Val Ala Arg Leu Ile
            515                 520                 525
Gly Lys His Phe Ile Asp Thr Leu Pro Pro Thr Pro Gly Lys Gln Arg
            530                 535                 540
Pro Gln Lys Gly Cys Lys Val Cys Arg Lys Arg Gly Ile Arg Arg Asp
545                 550                 555                 560
```

```
Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 59
<211> LENGTH: 589
<212> TYPE: PRT
<213> ORGANISM: Artificial sequence
<220> FEATURE:
<223> OTHER INFORMATION: Synthetic

<400> SEQUENCE: 59

Met Ala Lys Arg Phe Tyr Ser Ala Glu Glu Ala Ala His Cys Met
1               5                  10                  15

Ala Ser Ser Ser Glu Glu Phe Tyr Gly Ser Asp Ser Glu Tyr Val Pro
                20                  25                  30

Pro Ala Ser Glu Ser Asp Ser Ser Thr Glu Glu Ser Trp Cys Ser Ser
                35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
                115                 120                 125

Asp Met Val Leu Tyr Thr Asn Val Tyr Ala Glu Gln Tyr Leu Thr Gln
            130                 135                 140

Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
                180                 185                 190

Ser Ile Pro Val Phe Gly Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Leu Leu Phe Lys Gly Arg Leu Gln Phe Lys
                260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335
```

Gly Phe His Leu Tyr Val Asp Asn Phe Tyr Ser Ser Ile Pro Leu Phe
                340                 345                 350

Thr Ala Leu Tyr Cys Leu Asn Thr Pro Ala Cys Gly Thr Ile Asn Arg
            355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Asp Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Ile Pro Cys Phe Glu Ile Tyr His Thr Gln Leu His Tyr
            580                 585

<210> SEQ ID NO 60
<211> LENGTH: 589
<212> TYPE: PRT
<213> ORGANISM: Artificial sequence
<220> FEATURE:
<223> OTHER INFORMATION: Synthetic

<400> SEQUENCE: 60

Met Ala Lys Arg Phe Tyr Ser Ala Glu Glu Ala Ala His Cys Ser
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

```
Glu Pro Ile Asn Phe Phe Gln Leu Phe Met Thr Glu Ala Ile Leu Gln
            115                 120                 125
Asp Met Val Leu Tyr Thr Asn Val Tyr Ala Glu Gln Tyr Leu Thr Gln
        130                 135                 140
Asn Pro Leu Thr Arg Tyr Ala Arg Ala His Ala Trp His Pro Thr Asp
145                 150                 155                 160
Ile Cys Glu Met Lys Arg Phe Val Gly Leu Thr Leu Ala Met Gly Leu
                165                 170                 175
Ile Lys Ala Asn Ser Ile Glu Ser Tyr Trp Asp Thr Thr Val Leu
            180                 185                 190
Ser Ile Pro Val Phe Gly Ala Thr Met Ser Arg Asn Arg Tyr Gln Leu
        195                 200                 205
Leu Leu Arg Phe Leu His Phe Asn Asn Asn Ala Thr Ala Val Pro Pro
    210                 215                 220
Asp Gln Pro Gly His Asp Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Met Leu Phe Lys Gly Arg Leu Gln Phe Arg
            260                 265                 270
Gln Tyr Ile Pro Ser Lys Arg Ala Arg Tyr Gly Ile Lys Phe Tyr Lys
        275                 280                 285
Leu Cys Glu Ser Ser Thr Gly Tyr Thr Ser Tyr Phe Leu Ile Tyr Glu
    290                 295                 300
Gly Lys Asp Ser Lys Leu Asp Pro Pro Gly Cys Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Val Leu Asn Thr Pro Ala Cys Gly Thr Ile Asn Arg
        355                 360                 365
Asn Arg Lys Gly Leu Pro Arg Ala Leu Leu Asp Lys Lys Leu Asn Arg
    370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Pro Pro Lys Asn Lys Pro Leu
            420                 425                 430
Cys Ser Lys Glu Tyr Ser Lys Tyr Met Gly Gly Val Asp Arg Thr Asp
        435                 440                 445
Gln Leu Gln His Tyr Tyr Asn Ala Thr Arg Lys Thr Arg His Trp Tyr
    450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
            500                 505                 510
Gln Thr Val Pro Glu Met Pro Pro Ser Asp Asn Val Ala Arg Leu Ile
        515                 520                 525
```

```
Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
                580                 585
```

<210> SEQ ID NO 61
<211> LENGTH: 589
<212> TYPE: PRT
<213> ORGANISM: Artificial sequence
<220> FEATURE:
<223> OTHER INFORMATION: Synthetic

<400> SEQUENCE: 61

```
Met Ala Lys Arg Phe Tyr Ser Ala Glu Glu Ala Ala His Cys Ser
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Gly Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140

Asn Pro Leu Thr Arg Tyr Ala Arg Ala His Ala Trp Tyr Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
                180                 185                 190

Ser Ile Pro Val Phe Gly Ala Thr Met Ser Arg Asn Arg Tyr Gln Leu
    195                 200                 205

Leu Leu Arg Phe Leu His Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Asn Val Tyr Thr Pro Cys Gln Asn Ile
                245                 250                 255

Cys Ile Asp Glu Ser Leu Met Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Thr Gly Tyr Thr Ser Tyr Phe Leu Ile Tyr Glu
    290                 295                 300
```

```
Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
            325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
            405                 410                 415

Val Ile Arg Glu Gln Arg Val Gly Arg Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
            485                 490                 495

Tyr Gln Leu Gln Ile Leu Pro Ala Leu Leu Phe Gly Gly Val Glu Glu
        500                 505                 510

Gln Thr Val Pro Glu Met Pro Pro Ser Asp Asn Val Ala Arg Leu Ile
    515                 520                 525

Gly Lys His Phe Ile Asp Thr Leu Pro Pro Thr Pro Gly Lys Gln Arg
530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
            565                 570                 575

Lys Pro Cys Phe Glu Ile Tyr His Thr Gln Leu His Tyr
            580                 585

<210> SEQ ID NO 62
<211> LENGTH: 589
<212> TYPE: PRT
<213> ORGANISM: Artificial sequence
<220> FEATURE:
<223> OTHER INFORMATION: Synthetic

<400> SEQUENCE: 62

Met Ala Lys Arg Phe Tyr Ser Ala Glu Glu Ala Ala His Cys Ser
1               5                   10                  15

Ala Ser Ser Ser Asp Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80
```

```
Gly Gly Glu Pro Ala Trp Gly Pro Pro Cys Asn Phe Pro Pro Glu Ile
                85                  90                  95
Pro Pro Phe Thr Thr Val Pro Gly Val Lys Val Asp Thr Ser Asn Phe
            100                 105                 110
Glu Pro Ile Asn Phe Phe Gln Leu Phe Met Thr Glu Ala Ile Leu Gln
            115                 120                 125
Asp Met Val Leu Tyr Thr Asn Val Tyr Ala Glu Gln Tyr Leu Thr Gln
            130                 135                 140
Asn Pro Leu Thr Arg Gly Ala Arg Ala His Ala Trp Tyr Pro Thr Asp
145                 150                 155                 160
Ile Ala Glu Met Lys Arg Phe Val Gly Leu Thr Leu Ala Met Gly Leu
                165                 170                 175
Ile Lys Ala Asn Ser Leu Glu Ser Tyr Trp Asp Thr Thr Val Leu
                180                 185                 190
Ser Ile Pro Val Phe Gly Ala Thr Met Ser Arg Asn Arg Tyr Gln Leu
                195                 200                 205
Leu Leu Arg Phe Leu His Phe Asn Asn Asn Ala Thr Ala Val Pro Pro
            210                 215                 220
Asp Gln Pro Gly His Asp Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Met Leu Phe Lys Gly Arg Leu Gln Phe Arg
                260                 265                 270
Gln Tyr Ile Pro Ser Lys Arg Ala Arg Tyr Gly Ile Lys Phe Tyr Lys
            275                 280                 285
Leu Cys Glu Ser Ser Thr Gly Tyr Thr Ser Tyr Phe Leu Ile Tyr Glu
            290                 295                 300
Gly Lys Asp Ser Lys Leu Asp Pro Pro Gly Cys Pro Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Cys Leu Asn Thr Pro Ala Cys Gly Thr Ile Asn Arg
            355                 360                 365
Asn Arg Lys Gly Leu Pro Arg Ala Leu Leu Asp Lys Lys Leu Asn Arg
            370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Lys Pro Lys Asn Lys Pro Leu
                420                 425                 430
Cys Ser Lys Glu Tyr Ser Lys Tyr Met Gly Gly Val Asp Arg Thr Asp
            435                 440                 445
Gln Leu Gln His Tyr Tyr Asn Ala Thr Arg Lys Thr Arg His Trp Tyr
450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
```

```
                500                 505                 510
Gln Thr Val Pro Glu Met Pro Pro Ser Asp Ser Val Ala Arg Leu Ile
            515                 520                 525
Gly Lys His Phe Ile Asp Thr Leu Pro Pro Thr Pro Gly Lys Gln Arg
        530                 535                 540
Pro Gln Lys Gly Cys Lys Val Cys Arg Lys Arg Gly Ile Arg Arg Asp
545                 550                 555                 560
Thr Arg Tyr Tyr Cys Pro Lys Cys Pro Arg Asn Pro Gly Leu Cys Arg
                565                 570                 575
Lys Pro Cys Phe Glu Ile Tyr His Thr Gln Leu His Tyr
            580                 585

<210> SEQ ID NO 63
<211> LENGTH: 589
<212> TYPE: PRT
<213> ORGANISM: Artificial sequence
<220> FEATURE:
<223> OTHER INFORMATION: Synthetic

<400> SEQUENCE: 63

Met Ala Lys Arg Phe Tyr Ser Ala Glu Glu Ala Ala His Cys Met
1               5                   10                  15
Ala Ser Ser Glu Glu Phe Ser Gly Ser Asp Ser Glu Tyr Val Pro
                20                  25                  30
Pro Ala Ser Glu Ser Asp Ser Thr Glu Glu Ser Trp Cys Ser Ser
            35                  40                  45
Ser Thr Val Ser Ala Leu Glu Glu Pro Met Glu Val Asp Glu Asp Val
50                  55                  60
Asp Asp Leu Glu Asp Gln Glu Ala Gly Asp Arg Ala Asp Ala Ala Ala
65                  70                  75                  80
Gly Gly Glu Pro Ala Trp Gly Pro Pro Cys Asn Phe Pro Pro Glu Ile
                85                  90                  95
Pro Pro Phe Thr Thr Val Pro Gly Val Lys Val Asp Thr Ser Asn Phe
            100                 105                 110
Glu Pro Ile Asn Phe Phe Gln Leu Phe Met Thr Glu Ala Ile Leu Gln
        115                 120                 125
Asp Met Val Leu Tyr Thr Asn Val Tyr Ala Glu Gln Tyr Leu Thr Gln
130                 135                 140
Asn Pro Leu Thr Arg Tyr Ala Arg Ala His Ala Trp His Pro Thr Asp
145                 150                 155                 160
Ile Ala Glu Met Lys Arg Phe Val Gly Leu Thr Leu Ala Met Gly Leu
                165                 170                 175
Ile Lys Ala Asn Ser Leu Glu Ser Tyr Trp Asp Thr Thr Thr Val Leu
            180                 185                 190
Ser Ile Pro Val Phe Gly Ala Thr Met Ser Arg Asn Arg Tyr Gln Leu
        195                 200                 205
Leu Leu Arg Phe Leu His Phe Asn Asn Ala Thr Ala Val Pro Pro
    210                 215                 220
Asp Gln Pro Gly His Ala Arg Leu His Lys Leu Arg Pro Leu Ile Asp
225                 230                 235                 240
Ser Leu Ser Glu Arg Phe Ala Asn Val Tyr Thr Pro Cys Gln Asn Ile
                245                 250                 255
Cys Ile Asp Glu Ser Leu Leu Leu Phe Lys Gly Arg Leu Gln Phe Arg
            260                 265                 270
Gln Tyr Ile Pro Ser Lys Arg Ala Arg Tyr Gly Ile Lys Phe Tyr Lys
```

|     |     |     |     | 275 |     |     |     | 280 |     |     |     | 285 |     |     |
| --- | --- | --- | --- | --- | --- | --- | --- | --- | --- | --- | --- | --- | --- | --- |

Leu Cys Glu Ser Ser Ser Gly Tyr Thr Ser Tyr Phe Leu Ile Tyr Glu
290 295 300

Gly Lys Asp Ser Lys Leu Asp Pro Pro Gly Cys Pro Pro Asp Leu Thr
305 310 315 320

Val Ser Gly Lys Ile Val Trp Glu Leu Ile Ser Pro Leu Leu Gly Gln
325 330 335

Gly Phe His Leu Tyr Val Asp Asn Phe Tyr Ser Ser Ile Pro Leu Phe
340 345 350

Thr Ala Leu Tyr Cys Leu Asn Thr Pro Ala Cys Gly Thr Ile Asn Arg
355 360 365

Asn Arg Lys Gly Leu Pro Arg Ala Leu Leu Asp Lys Lys Leu Asn Arg
370 375 380

Gly Glu Thr Tyr Ala Leu Arg Lys Asn Glu Leu Leu Ala Ile Lys Phe
385 390 395 400

Phe Asp Lys Lys Asn Val Phe Met Leu Thr Ser Ile His Asp Glu Ser
405 410 415

Val Ile Arg Glu Gln Arg Val Gly Arg Pro Pro Lys Asn Lys Pro Leu
420 425 430

Cys Ser Lys Glu Tyr Ser Lys Tyr Met Gly Gly Val Asp Arg Thr Asp
435 440 445

Gln Leu Gln His Tyr Tyr Asn Ala Thr Arg Lys Thr Arg His Trp Tyr
450 455 460

Lys Lys Val Gly Ile Tyr Leu Ile Gln Met Ala Leu Arg Asn Ser Tyr
465 470 475 480

Ile Val Tyr Lys Ala Ala Val Pro Gly Pro Lys Leu Ser Tyr Tyr Lys
485 490 495

Tyr Gln Leu Gln Ile Leu Pro Ala Leu Leu Phe Gly Gly Val Glu Glu
500 505 510

Gln Thr Val Pro Glu Met Pro Pro Ser Asp Asn Val Ala Arg Leu Ile
515 520 525

Gly Lys His Phe Ile Asp Thr Leu Pro Pro Thr Pro Gly Lys Gln Arg
530 535 540

Pro Gln Lys Gly Cys Lys Val Cys Arg Lys Arg Gly Ile Arg Arg Asp
545 550 555 560

Thr Arg Tyr Tyr Cys Pro Lys Cys Pro Arg Asn Pro Gly Leu Cys Arg
565 570 575

Lys Pro Cys Phe Glu Ile Tyr His Thr Gln Leu His Tyr
580 585

<210> SEQ ID NO 64
<211> LENGTH: 589
<212> TYPE: PRT
<213> ORGANISM: Artificial sequence
<220> FEATURE:
<223> OTHER INFORMATION: Synthetic

<400> SEQUENCE: 64

Met Ala Lys Arg Phe Tyr Ser Ala Glu Glu Ala Ala His Cys Met
1 5 10 15

Ala Ser Ser Ser Glu Glu Thr Ser Gly Ser Asp Ser Glu Tyr Val Pro
20 25 30

Pro Ala Ser Glu Ser Asp Ser Ser Thr Glu Glu Ser Trp Cys Ser Ser
35 40 45

Ser Thr Val Ser Ala Leu Glu Glu Pro Met Glu Val Asp Glu Asp Val

-continued

```
                50                  55                  60
Asp Asp Leu Glu Asp Gln Glu Ala Gly Asp Arg Ala Asp Ala Ala Ala
 65                  70                  75                  80
Gly Gly Glu Pro Ala Trp Gly Pro Pro Cys Asn Phe Pro Pro Glu Ile
                 85                  90                  95
Pro Pro Phe Thr Thr Val Pro Gly Val Lys Val Asp Thr Ser Asn Phe
                100                 105                 110
Glu Pro Ile Asn Phe Phe Gln Leu Phe Met Thr Glu Ala Ile Leu Gln
                115                 120                 125
Asp Met Val Leu Tyr Thr Asn Val Tyr Ala Glu Gln Tyr Leu Thr Gln
                130                 135                 140
Asn Pro Leu Thr Arg Tyr Ala Arg Ala His Ala Trp His Pro Thr Asp
145                 150                 155                 160
Ile Ala Glu Met Lys Arg Phe Val Gly Leu Thr Leu Ala Met Gly Leu
                165                 170                 175
Ile Lys Ala Asn Ser Leu Glu Ser Tyr Trp Asp Thr Thr Thr Val Leu
                180                 185                 190
Ser Ile Pro Val Phe Ser Ala Thr Met Ser Arg Asn Arg Tyr Gln Leu
                195                 200                 205
Leu Leu Arg Phe Leu His Phe Asn Asn Asn Ala Thr Ala Val Pro Pro
                210                 215                 220
Asp Gln Pro Gly His Asp Arg Leu His Lys Leu Arg Pro Leu Ile Asp
225                 230                 235                 240
Ser Leu Ser Glu Arg Phe Ala Ala Val Tyr Thr Pro Cys Gln Asn Ile
                245                 250                 255
Cys Ile Asp Glu Ser Leu Leu Leu Phe Lys Gly Arg Leu Gln Phe Arg
                260                 265                 270
Gln Tyr Ile Pro Ser Lys Arg Ala Arg Tyr Gly Ile Lys Phe Tyr Lys
                275                 280                 285
Leu Cys Glu Ser Ser Ser Gly Tyr Thr Ser Tyr Phe Leu Ile Tyr Glu
                290                 295                 300
Gly Lys Asp Ser Lys Leu Asp Pro Pro Gly Cys Pro Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
                340                 345                 350
Thr Ala Leu Tyr Cys Leu Asn Thr Pro Ala Cys Gly Thr Ile Asn Arg
                355                 360                 365
Asn Arg Lys Gly Leu Pro Arg Ala Leu Leu Asp Lys Lys Leu Asn Arg
                370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg His Gly Arg Pro Pro Lys Asn Lys Pro Leu
                420                 425                 430
Cys Ser Lys Glu Tyr Ser Lys Tyr Met Gly Gly Val Asp Arg Ala Asp
                435                 440                 445
Gln Leu Gln His Tyr Tyr Asn Ala Thr Arg Lys Thr Arg His Trp Tyr
                450                 455                 460
Lys Lys Val Gly Ile Tyr Leu Ile Gln Met Ala Leu Arg Asn Ser Tyr
465                 470                 475                 480
```

```
Ile Val Tyr Lys Ala Ala Val Pro Gly Pro Lys Leu Ser Tyr Tyr Lys
                485             490             495

Tyr Gln Leu Gln Ile Leu Pro Ala Leu Leu Phe Gly Gly Val Glu Glu
            500             505             510

Gln Thr Val Pro Glu Met Pro Pro Ser Asp Asn Val Ala Arg Leu Ile
            515             520             525

Gly Lys His Phe Ile Asp Thr Leu Pro Pro Thr Pro Gly Lys Gln Arg
        530             535             540

Pro Gln Lys Gly Cys Lys Val Cys Arg Lys Arg Gly Ile Arg Arg Asp
545             550             555             560

Thr Arg Tyr Tyr Cys Pro Lys Cys Pro Arg Asn Pro Gly Leu Cys Arg
                565             570             575

Lys Pro Cys Phe Glu Ile Tyr His Thr Gln Leu His Tyr
                580             585

<210> SEQ ID NO 65
<211> LENGTH: 589
<212> TYPE: PRT
<213> ORGANISM: Artificial sequence
<220> FEATURE:
<223> OTHER INFORMATION: Synthetic

<400> SEQUENCE: 65

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
130                 135                 140

Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Glu Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255
```

```
Cys Ile Asp Glu Ser Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ile Pro Leu Phe
            340                 345                 350

Thr Ala Leu Tyr Cys Leu Asn Thr Pro Ala Cys Gly Thr Ile Asn Arg
        355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
            420                 425                 430

Cys Ser Lys Glu Tyr Ser Lys Tyr Met Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 66
<211> LENGTH: 589
<212> TYPE: PRT
<213> ORGANISM: Artificial sequence
<220> FEATURE:
<223> OTHER INFORMATION: Synthetic

<400> SEQUENCE: 66

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
                20                  25                  30
```

-continued

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140

Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
                180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
    355                 360                 365

Asn Arg Lys Gly Leu Pro Arg Ala Leu Leu Asp Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
                420                 425                 430

Cys Ser Lys Glu Tyr Ser Lys Tyr Met Gly Gly Val Asp Arg Thr Asp
                435                 440                 445

Gln Leu Gln His Tyr Tyr Asn Ala Thr Arg Lys Thr Arg Ala Trp Tyr
        450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
                580                 585

<210> SEQ ID NO 67
<211> LENGTH: 589
<212> TYPE: PRT
<213> ORGANISM: Artificial sequence
<220> FEATURE:
<223> OTHER INFORMATION: Synthetic

<400> SEQUENCE: 67

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
    130                 135                 140

Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Asn Ala Thr Ala Val Pro Pro
    210                 215                 220

```
Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
            245                 250                 255

Cys Ile Asp Glu Ser Leu Leu Leu Phe Lys Gly Arg Leu Gln Phe Arg
        260                 265                 270

Gln Tyr Ile Pro Ser Lys Arg Ala Arg Tyr Gly Ile Lys Phe Tyr Lys
    275                 280                 285

Leu Cys Glu Ser Ser Ser Gly Tyr Thr Ser Tyr Phe Leu Ile Tyr Glu
290                 295                 300

Gly Lys Asp Ser Lys Leu Asp Pro Pro Gly Cys Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg His Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Arg
                565                 570                 575

Lys Pro Cys Phe Glu Ile Tyr His Thr Gln Leu His Tyr
            580                 585

<210> SEQ ID NO 68
<211> LENGTH: 589
<212> TYPE: PRT
<213> ORGANISM: Artificial sequence
<220> FEATURE:
<223> OTHER INFORMATION: Synthetic

<400> SEQUENCE: 68
```

-continued

```
Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
                35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
                115                 120                 125

Asp Met Val Leu Tyr Thr Asn Val Tyr Ala Glu Gln Tyr Leu Thr Gln
            130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
            180                 185                 190

Lys Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
            325                 330                 335

Gly Phe His Leu Tyr Val Asp Asn Phe Tyr Ser Ser Ile Pro Leu Phe
            340                 345                 350

Thr Ala Leu Tyr Cys Leu Asn Thr Pro Ala Cys Gly Thr Ile Asn Arg
            355                 360                 365

Asn Arg Lys Gly Leu Pro Arg Ala Leu Leu Asp Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
```

```
                420             425             430
Cys Ser Lys Glu Tyr Ser Lys Tyr Met Gly Val Asp Arg Thr Asp
        435             440             445

Gln Leu Gln His Tyr Tyr Asn Ala Thr Arg Lys Thr Arg His Trp Tyr
    450             455             460

Lys Lys Val Gly Ile Tyr Leu Ile Gln Met Ala Leu Arg Asn Ser Tyr
465             470             475             480

Ile Val Tyr Lys Ala Ala Val Pro Gly Pro Lys Leu Ser Tyr Tyr Lys
                485             490             495

Tyr Gln Leu Gln Ile Leu Pro Ala Leu Leu Phe Gly Gly Val Glu Glu
            500             505             510

Gln Thr Val Pro Glu Met Pro Pro Ser Asp Asn Val Ala Arg Leu Ile
            515             520             525

Gly Lys His Phe Ile Asp Thr Leu Pro Pro Thr Pro Gly Lys Gln Arg
        530             535             540

Pro Gln Lys Gly Cys Lys Val Cys Arg Lys Arg Gly Ile Arg Arg Asp
545             550             555             560

Thr Arg Tyr Tyr Cys Pro Lys Cys Pro Arg Asn Pro Gly Leu Cys Phe
                565             570             575

Lys Pro Cys Phe Glu Ile Tyr His Thr Gln Leu His Tyr
            580             585

<210> SEQ ID NO 69
<211> LENGTH: 589
<212> TYPE: PRT
<213> ORGANISM: Artificial sequence
<220> FEATURE:
<223> OTHER INFORMATION: Synthetic

<400> SEQUENCE: 69

Met Ala Lys Arg Phe Tyr Ser Ala Glu Glu Ala Ala His Cys Met
1               5               10              15

Ala Ser Ser Ser Glu Glu Phe Ser Gly Ser Asp Ser Glu Tyr Val Pro
            20              25              30

Pro Ala Ser Glu Ser Asp Ser Ser Thr Glu Glu Ser Trp Cys Ser Ser
        35              40              45

Ser Thr Val Ser Ala Leu Glu Glu Pro Met Glu Val Asp Glu Asp Val
    50              55              60

Asp Asp Leu Glu Asp Gln Ala Gly Asp Arg Ala Asp Ala Ala Ala
65              70              75              80

Gly Gly Glu Pro Ala Trp Gly Pro Pro Cys Asn Phe Pro Pro Glu Ile
                85              90              95

Pro Pro Phe Thr Thr Val Pro Gly Val Lys Val Asp Thr Ser Asn Phe
            100             105             110

Glu Pro Ile Asn Phe Phe Gln Leu Phe Met Thr Glu Ala Ile Leu Gln
        115             120             125

Asp Met Val Leu Tyr Thr Asn Val Tyr Ala Glu Gln Gln Leu Thr Gln
    130             135             140

Asn Pro Leu Pro Arg Tyr Ala Arg Ala His Ala Trp His Pro Thr Asp
145             150             155             160

Ile Ala Glu Met Lys Arg Phe Val Gly Leu Thr Leu Ala Met Gly Leu
                165             170             175

Ile Lys Ala Asn Ser Leu Glu Ser Tyr Trp Asp Thr Thr Thr Val Leu
            180             185             190

Ser Ile Pro Val Phe Ser Ala Thr Met Ser Arg Asn Arg Tyr Gln Leu
```

```
                195                 200                 205
Leu Leu Arg Phe Leu His Phe Asn Asn Asn Ala Thr Ala Val Pro Pro
    210                 215                 220
Asp Gln Pro Gly His Asp Arg Leu His Lys Leu Arg Pro Leu Ile Asp
225                 230                 235                 240
Ser Leu Ser Glu Arg Phe Ala Ala Val Tyr Thr Pro Cys Gln Asn Ile
                245                 250                 255
Cys Ile Asp Glu Ser Leu Leu Leu Phe Lys Gly Arg Leu Gln Phe Arg
            260                 265                 270
Gln Tyr Ile Pro Ser Lys Arg Ala Arg Tyr Gly Ile Lys Phe Tyr Lys
        275                 280                 285
Leu Cys Glu Ser Ser Ser Gly Tyr Thr Ser Tyr Phe Leu Ile Tyr Glu
    290                 295                 300
Gly Lys Asp Arg Lys Leu Asp Pro Pro Gly Cys Pro Pro Asp Leu Thr
305                 310                 315                 320
Val Ser Gly Lys Ile Val Trp Glu Leu Ile Ser Pro Leu Leu Gly Gln
                325                 330                 335
Gly Phe His Leu Tyr Val Asp Asn Phe Tyr Ser Ser Ile Pro Leu Phe
            340                 345                 350
Thr Ala Leu Tyr Cys Leu Asp Thr Pro Ala Cys Gly Thr Ile Asn Arg
        355                 360                 365
Asn Arg Lys Gly Leu Pro Arg Ala Leu Leu Asp Lys Lys Leu Asn Arg
    370                 375                 380
Gly Glu Thr Tyr Ala Leu Arg Lys Asn Glu Leu Leu Ala Ile Lys Phe
385                 390                 395                 400
Phe Asp Lys Lys Asn Val Phe Met Leu Thr Ser Ile His Asp Glu Ser
                405                 410                 415
Val Ile Arg Glu Gln Arg Val Gly Arg Pro Pro Lys Asn Lys Pro Leu
            420                 425                 430
Cys Ser Lys Glu Tyr Ser Lys Tyr Met Gly Gly Val Asp Arg Thr Asp
        435                 440                 445
Gln Leu Gln His Tyr Tyr Asn Ala Thr Arg Lys Thr Arg Ala Trp Tyr
    450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
            500                 505                 510
Gln Thr Val Pro Glu Met Pro Pro Ser Asp Asn Val Ala Arg Leu Ile
        515                 520                 525
Gly Lys His Phe Ile Asp Thr Leu Pro Pro Thr Pro Gly Lys Gln Arg
    530                 535                 540
Pro Gln Lys Gly Cys Lys Val Cys Arg Lys Arg Gly Ile Arg Arg Asp
545                 550                 555                 560
Thr Arg Tyr Tyr Cys Pro Lys Cys Pro Arg Asn Pro Gly Leu Cys Phe
                565                 570                 575
Lys Pro Cys Phe Glu Ile Tyr His Thr Gln Tyr His Tyr
            580                 585

<210> SEQ ID NO 70
<211> LENGTH: 589
<212> TYPE: PRT
<213> ORGANISM: Artificial sequence
```

<220> FEATURE:
<223> OTHER INFORMATION: Synthetic

<400> SEQUENCE: 70

```
Met Ala Lys Arg Phe Tyr Ser Ala Glu Ala Ala His Cys Met
1               5                   10                  15

Ala Ser Ser Glu Glu Pro Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                      45

Ser Thr Val Ser Ala Leu Glu Glu Pro Met Glu Val Asp Glu Asp Val
    50                      55                  60

Asp Asp Leu Glu Asp Gln Glu Ala Gly Asp Arg Ala Asp Ala Ala Ala
65                      70                  75                  80

Gly Gly Glu Pro Ala Trp Gly Pro Pro Cys Asn Phe Pro Pro Glu Ile
                85                      90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
        130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr His Leu Tyr Cys Leu Asp Thr Pro Ala Cys Gly Thr Ile Asn Arg
        355                 360                 365

Asn Arg Lys Gly Leu Pro Arg Ala Leu Leu Asp Lys Leu Asn Arg
    370                 375                 380

Gly Glu Thr Tyr Ala Leu Arg Lys Asn Glu Leu Leu Ala Ile Lys Phe
385                 390                 395                 400
```

-continued

```
Phe Asp Lys Lys Asn Val Phe Met Leu Thr Ser Ile His Asp Glu Ser
            405                 410                 415
Val Ile Arg Glu Gln Arg Val Gly Arg Pro Pro Lys Asn Lys Pro Leu
        420                 425                 430
Cys Ser Lys Glu Tyr Ser Lys Tyr Met Gly Gly Val Asp Arg Thr Asp
        435                 440                 445
Gln Leu Gln His Tyr Tyr Asn Ala Thr Arg Lys Thr Arg Ala Trp Tyr
    450                 455                 460
Lys Lys Val Gly Ile Tyr Leu Ile Gln Met Ala Leu Arg Asn Ser Tyr
465                 470                 475                 480
Ile Val Tyr Lys Ala Ala Val Pro Gly Pro Lys Leu Ser Tyr Tyr Lys
                485                 490                 495
Tyr Gln Leu Gln Ile Leu Pro Ala Leu Leu Phe Gly Gly Val Glu Glu
            500                 505                 510
Gln Thr Val Pro Glu Met Pro Pro Ser Asp Asn Val Ala Arg Leu Ile
        515                 520                 525
Gly Lys His Phe Ile Asp Thr Leu Pro Pro Thr Pro Gly Lys Gln Arg
        530                 535                 540
Pro Gln Lys Gly Cys Lys Val Cys Arg Lys Arg Gly Ile Arg Arg Asp
545                 550                 555                 560
Thr Arg Tyr Tyr Cys Pro Lys Cys Pro Arg Asn Pro Gly Leu Cys Phe
                565                 570                 575
Lys Pro Cys Phe Glu Ile Tyr His Thr Gln Tyr His Tyr
            580                 585

<210> SEQ ID NO 71
<211> LENGTH: 592
<212> TYPE: PRT
<213> ORGANISM: Artificial sequence
<220> FEATURE:
<223> OTHER INFORMATION: Synthetic

<400> SEQUENCE: 71

Met Ala Lys Arg Phe Tyr Ser Ala Glu Glu Ala Ala His Cys Met
1               5                   10                  15
Ala Ser Ser Gln Glu Glu Phe Ser Gly Ser Asp Ser Glu Tyr Val Pro
            20                  25                  30
Pro Ala Ser Glu Ser Asp Ser Ser Thr Glu Glu Ser Trp Cys Ser Ser
        35                  40                  45
Ser Thr Val Ser Ala Leu Glu Glu Pro Met Glu Val Asp Glu Asp Val
    50                  55                  60
Asp Asp Leu Glu Asp Gln Glu Ala Gly Asp Arg Val Asp Ala Ala Ala
65                  70                  75                  80
Gly Gly Glu Pro Ala Trp Gly Pro Pro Cys Asn Phe Pro Pro Glu Ile
                85                  90                  95
Pro Pro Phe Thr Thr Val Pro Gly Val Lys Val Asp Thr Ser Asn Phe
            100                 105                 110
Glu Pro Ile Asn Phe Phe Gln Leu Phe Met Thr Glu Ala Ile Leu Gln
        115                 120                 125
Asp Met Val Leu Tyr Thr Asn Val Tyr Ala Glu Gln Tyr Leu Thr Gln
    130                 135                 140
Asn Pro Leu Pro Arg Tyr Ala Arg Ala His Ala Trp His Pro Thr Asp
145                 150                 155                 160
Ile Ala Glu Met Lys Arg Phe Val Gly Leu Thr Leu Ala Met Gly Leu
                165                 170                 175
```

```
Ile Lys Lys Asn Ser Leu Glu Ser Tyr Trp Asp Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590
```

```
<210> SEQ ID NO 72
<211> LENGTH: 592
<212> TYPE: PRT
<213> ORGANISM: Artificial sequence
<220> FEATURE:
<223> OTHER INFORMATION: Synthetic

<400> SEQUENCE: 72

Met Ala Lys Arg Phe Tyr Ser Ala Glu Ala Ala His Cys Met
1               5                   10                  15

Ala Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
                115                 120                 125

Asp Met Val Leu Tyr Thr Asn Val Tyr Ala Glu Gln Tyr Leu Thr Gln
            130                 135                 140

Asn Lys Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Gly Thr Val His
                180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
                340                 345                 350

Thr Ala Leu Tyr Cys Leu Asp Thr Pro Ala Cys Gly Thr Ile Asn Arg
            355                 360                 365
```

```
Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
            420                 425                 430

Cys Ser Lys Glu Tyr Ser Lys Tyr Met Gly Gly Val Asp Arg Thr Asp
                435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
    500                 505                 510

Gln Thr Val Pro Glu Met Pro Pro Ser Asp Asn Val Ala Arg Leu Ile
    515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
                580                 585                 590

<210> SEQ ID NO 73
<211> LENGTH: 592
<212> TYPE: PRT
<213> ORGANISM: Artificial sequence
<220> FEATURE:
<223> OTHER INFORMATION: Synthetic

<400> SEQUENCE: 73

Met Ala Lys Arg Phe Cys Ser Ala Glu Ala Ala His Cys Met
1               5                   10                  15

Ala Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
                35                  40                  45

Ser Thr Val Ser Ala Leu Glu Glu Pro Met Gly Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
                100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140
```

```
Asn Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
            165                 170                 175

Ile Lys Ala Asn Ser Leu Glu Ser Tyr Trp Asp Thr Thr Val Leu
        180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
            245                 250                 255

Cys Ile Asp Glu Ser Leu Leu Leu Phe Lys Gly Arg Leu Gln Phe Arg
        260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
            325                 330                 335

Gly Phe His Leu Tyr Val Asp Asn Phe Tyr Ser Ser Ile Pro Leu Phe
        340                 345                 350

Thr Ala Leu Tyr Cys Leu Asp Thr Pro Ala Cys Gly Thr Ile Asn Arg
    355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
            405                 410                 415

Val Ile Arg Glu Gln Arg Val Gly Arg Pro Pro Lys Asn Lys Pro Leu
        420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
            485                 490                 495

Tyr Gln Leu Gln Ile Leu Pro Ala Leu Leu Phe Gly Gly Val Glu Glu
        500                 505                 510

Gln Thr Val Pro Glu Met Pro Pro Ser Asp Asn Val Ala Arg Leu Ile
        515                 520                 525

Gly Lys His Phe Ile Ala Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
```

```
                      565                 570                 575

Lys Pro Cys Phe Glu Ile Tyr His Thr Gln Leu His Tyr Gly Arg Arg
            580                 585                 590

<210> SEQ ID NO 74
<211> LENGTH: 592
<212> TYPE: PRT
<213> ORGANISM: Artificial sequence
<220> FEATURE:
<223> OTHER INFORMATION: Synthetic

<400> SEQUENCE: 74

Met Ala Lys Arg Phe Tyr Ser Ala Glu Ala Ala His Cys Met
1               5                   10                  15

Ala Ser Ser Glu Glu Phe Ser Gly Ser Asp Ser Glu Tyr Val Pro
                20                  25                  30

Pro Ala Ser Glu Ser Asp Ser Thr Glu Glu Ser Trp Cys Ser Ser
            35                  40                  45

Ser Thr Val Ser Ala Leu Glu Glu Pro Met Glu Val Asp Glu Asp Val
50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
130                 135                 140

Val Pro Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Lys Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
            290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
```

```
                    340                 345                 350
Thr Ala Leu Tyr Cys Leu Asp Thr Pro Ala Cys Gly Thr Ile Asn Arg
                355                 360                 365

Asn Arg Lys Gly Leu Pro Arg Ala Leu Leu Asp Lys Lys Leu Asn Arg
            370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
            420                 425                 430

Cys Ser Lys Glu Tyr Ser Lys Tyr Met Gly Gly Val Asp Arg Thr Asp
                435                 440                 445

Gln Leu Gln His Tyr Tyr Asn Ala Thr Arg Lys Thr Arg Ala Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
            530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590

<210> SEQ ID NO 75
<211> LENGTH: 592
<212> TYPE: PRT
<213> ORGANISM: Artificial sequence
<220> FEATURE:
<223> OTHER INFORMATION: Synthetic

<400> SEQUENCE: 75

Met Ala Lys Arg Phe Tyr Ser Ala Glu Glu Ala Ala His Cys Met
1               5                   10                  15

Ala Ser Ser Ser Glu Glu Phe Ser Gly Ser Asp Gln Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
        50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
```

```
            115                 120                 125
Asp Met Val Leu Tyr Thr Asn Val Tyr Ala Glu Gln Tyr Leu Thr Gln
    130                 135                 140

Asn Lys Leu Thr Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
                180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
                260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
                340                 345                 350

Thr Ala Leu Tyr Cys Leu Asp Thr Pro Ala Cys Gly Thr Ile Asn Arg
            355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
                420                 425                 430

Cys Ser Lys Glu Tyr Ser Lys Tyr Met Gly Gly Val Asp Arg Thr Asp
            435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
530                 535                 540
```

```
Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590
```

<210> SEQ ID NO 76
<211> LENGTH: 592
<212> TYPE: PRT
<213> ORGANISM: Artificial sequence
<220> FEATURE:
<223> OTHER INFORMATION: Synthetic

<400> SEQUENCE: 76

```
Met Ala Lys Arg Phe Tyr Ser Ala Glu Ala Ala His Cys Met
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
130                 135                 140

Asn Val Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Asp Ala Thr Ala Val Pro Pro
210                 215                 220

Asp Gln Pro Gly His Asp Arg Leu His Lys Leu Arg Pro Leu Ile Asp
225                 230                 235                 240

Ser Leu Thr Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Pro Asp Leu Thr
305                 310                 315                 320
```

Val Ser Gly Lys Ile Val Trp Glu Leu Ile Ser Pro Leu Leu Gly Gln
            325                 330                 335

Gly Phe His Leu Tyr Val Asp Asn Phe Tyr Ser Ile Pro Leu Phe
        340                 345                 350

Thr Ala Leu Tyr Cys Leu Asp Thr Pro Ala Cys Gly Thr Ile Asn Arg
        355                 360                 365

Asn Arg Lys Gly Leu Pro Arg Ala Leu Leu Asp Lys Lys Leu Asn Arg
    370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590

<210> SEQ ID NO 77
<211> LENGTH: 592
<212> TYPE: PRT
<213> ORGANISM: Artificial sequence
<220> FEATURE:
<223> OTHER INFORMATION: Synthetic

<400> SEQUENCE: 77

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
        35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Ala Asp Ala Ala Pro
65                  70                  75                  80

Gly Gly Glu Pro Ala Trp Gly Pro Cys Asn Phe Pro Pro Glu Ile
                85                  90                  95

```
Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
        130                 135                 140

Val Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
        195                 200                 205

Leu Leu Arg Phe Leu His Phe Asn Asn Glu Ala Thr Ala Val Pro Pro
    210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
        340                 345                 350

Thr Ala Leu Tyr Cys Leu Asp Thr Pro Ala Cys Gly Thr Ile Asn Arg
    355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
        420                 425                 430

Cys Ser Lys Glu Tyr Ser Lys Tyr Met Gly Gly Val Asp Arg Thr Asp
    435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
        500                 505                 510
```

```
Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
                580                 585                 590

<210> SEQ ID NO 78
<211> LENGTH: 592
<212> TYPE: PRT
<213> ORGANISM: Artificial sequence
<220> FEATURE:
<223> OTHER INFORMATION: Synthetic

<400> SEQUENCE: 78

Met Ala Lys Arg Phe Tyr Ser Ala Glu Glu Ala Ala His Cys Met
1               5                   10                  15

Ala Ser Ser Glu Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
    50                  55                  60

Asp Asp Leu Glu Asp Gln Glu Ala Gly Asp Arg Val Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
    130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Thr Val Leu
            180                 185                 190

Ser Ile Pro Val Phe Ser Ala Thr Met Ser Arg Asn Arg Tyr Gln Leu
    195                 200                 205

Leu Leu Lys Phe Leu His Phe Asn Asn Glu Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285
```

```
Leu Cys Glu Ser Ser Ser Gly Tyr Thr Ser Tyr Phe Leu Ile Tyr Glu
    290                 295                 300

Gly Lys Asp Ser Lys Leu Asp Pro Pro Gly Cys Pro Asp Leu Thr
305                 310                 315                 320

Val Ser Gly Lys Ile Val Trp Glu Leu Ile Ser Pro Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
        355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
        435                 440                 445

Gln Leu Gln His Tyr Tyr Asn Ala Thr Arg Lys Thr Arg Ala Trp Tyr
    450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
        515                 520                 525

Gly Lys His Phe Ile Asp Thr Leu Pro Pro Thr Pro Gly Lys Gln Arg
    530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590

<210> SEQ ID NO 79
<211> LENGTH: 592
<212> TYPE: PRT
<213> ORGANISM: Artificial sequence
<220> FEATURE:
<223> OTHER INFORMATION: Synthetic

<400> SEQUENCE: 79

Met Ala Lys Arg Phe Tyr Ser Ala Glu Glu Ala Ala His Cys Met
1               5                   10                  15

Ala Ser Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
        50                  55                  60
```

```
Asp Asp Leu Glu Asp Gln Glu Ala Gly Asp Arg Ala Asp Ala Ala Ala
 65                  70                  75                  80

Gly Gly Glu Pro Ala Trp Gly Pro Pro Cys Asn Phe Pro Pro Glu Ile
             85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
130                 135                 140

Val Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
                180                 185                 190

Asn Ile Pro Val Phe Ser Ala Thr Met Ser Arg Asn Arg Tyr Gln Leu
            195                 200                 205

Leu Leu Arg Phe Leu Glu Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
            275                 280                 285

Leu Cys Glu Ser Ser Ser Gly Tyr Thr Ser Tyr Phe Leu Ile Tyr Glu
            290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
            355                 360                 365

Asn Arg Lys Gly Leu Pro Arg Ala Leu Leu Asp Lys Lys Leu Asn Arg
            370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Lys Asn Lys Pro Leu
            420                 425                 430

Cys Ser Lys Glu Tyr Ser Lys Tyr Met Gly Gly Val Asp Arg Thr Asp
            435                 440                 445

Gln Leu Gln His Tyr Tyr Asn Ala Thr Arg Lys Thr Arg Ala Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
```

```
            485                 490                 495
Tyr Gln Leu Gln Ile Leu Pro Ala Leu Leu Phe Gly Gly Val Glu Glu
                500                 505                 510

Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
        530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr Gly Arg Arg
            580                 585                 590

<210> SEQ ID NO 80
<211> LENGTH: 16
<212> TYPE: DNA
<213> ORGANISM: Artificial sequence
<220> FEATURE:
<223> OTHER INFORMATION: Synthetic

<400> SEQUENCE: 80
cccggcgagc atgagg                                                       16

<210> SEQ ID NO 81
<211> LENGTH: 16
<212> TYPE: DNA
<213> ORGANISM: Artificial sequence
<220> FEATURE:
<223> OTHER INFORMATION: Synthetic

<400> SEQUENCE: 81
cctcatgctc gccggg                                                       16

<210> SEQ ID NO 82
<211> LENGTH: 205
<212> TYPE: DNA
<213> ORGANISM: Artificial sequence
<220> FEATURE:
<223> OTHER INFORMATION: Synthetic

<400> SEQUENCE: 82
cagggtatct catacccNgg taaaatttta aagttgtgta ttttataaaa ttttcgtctg        60
acaacactag cgcgctcagt agctggaggc aggagcgtgc gggaggggat agtggcgtga       120
tcgcagtgtg gcacgggaca ccggcgagat attcgtgtgc aaacctgttt cgggtatgtt       180
atacccNgcc tcattgttga cgtat                                             205

<210> SEQ ID NO 83
<211> LENGTH: 192
<212> TYPE: DNA
<213> ORGANISM: Artificial sequence
<220> FEATURE:
<223> OTHER INFORMATION: Synthetic

<400> SEQUENCE: 83
tttaagaaaa agattaataa ataataataa tttcataatt aaaaacttct ttcattgaat        60
gccattaaat aaaccattat tttacaaaat aagatcaaca taattgagta aataataata       120
agaacaatat tatagtacaa caaaatatgg gtatgtcata ccctgccaca ttcttgatgt       180 aactttttt ca                                                            192
```

<210> SEQ ID NO 84
<211> LENGTH: 610
<212> TYPE: PRT
<213> ORGANISM: Artificial sequence
<220> FEATURE:
<223> OTHER INFORMATION: Synthetic

<400> SEQUENCE: 84

```
Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Ala Leu Leu Tyr Leu Ala Gly Leu Ile Lys Ser Asn Arg
                195                 200                 205

Gln Ser Leu Lys Asp Leu Trp Arg Thr Asp Gly Thr Gly Val Asp Ile
                210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
                275                 280                 285

Leu Ser Phe Arg Gly Arg Cys Leu Phe Arg Val Tyr Ile Pro Asn Lys
                290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
                355                 360                 365
```

```
Thr Gly Tyr Glu Leu Met Leu His Leu Leu Asn Glu Tyr Arg Leu Thr
        370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
                420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
        450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
                500                 505                 510

Ile Lys Arg Thr Glu Phe Ile Arg Ser Leu Gly Leu Ser Met Ile Tyr
        515                 520                 525

Glu His Leu His Ser Arg Asn Lys Lys Asn Ile Pro Thr Tyr Leu
        530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
                580                 585                 590

Met Glu His Ala Lys Phe Leu Cys Glu Asn Cys Ala Glu Leu Asp Ser
                595                 600                 605

Ser Leu
    610

<210> SEQ ID NO 85
<211> LENGTH: 610
<212> TYPE: PRT
<213> ORGANISM: Artificial sequence
<220> FEATURE:
<223> OTHER INFORMATION: Synthetic

<400> SEQUENCE: 85

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
        50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110
```

```
Pro Asn Val Arg Leu Arg Ser Glu Asn Ile Val Thr Glu Gln Ala Gln
         115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Gly Leu Leu Tyr Ile Ala Gly Leu Ile Lys Ser Asn Arg
        195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Leu Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val His Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
        355                 360                 365

Thr Gly Tyr Glu Val Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
        435                 440                 445

Glu Lys Gln Lys Pro Glu Met Ile Thr Phe Tyr Asn Ser Thr Lys Ala
    450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
        515                 520                 525
```

-continued

Glu His Leu His Ser Arg Asn Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala His Leu Asp Ser
            595                 600                 605

Ser Leu
    610

<210> SEQ ID NO 86
<211> LENGTH: 610
<212> TYPE: PRT
<213> ORGANISM: Artificial sequence
<220> FEATURE:
<223> OTHER INFORMATION: Synthetic

<400> SEQUENCE: 86

Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
                35                  40                  45

Asp Ser Val Asp Val Pro Ser Asn Ser Arg Gln Glu Glu Ala Asn Ala
50                  55                  60

Ile Ile Ala Asn Glu Ser Asp Ser Asp Pro Asp Asp Asp Leu Pro Leu
65                  70                  75                  80

Ser Leu Val Arg Glu Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Gly Leu Leu Tyr Ile Ala Gly Leu Ile Lys Ser Asn Arg
                195                 200                 205

Gln Ser Leu Lys Asp Leu Trp Arg Thr Asp Gly Thr Gly Val Asp Ile
            210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
                260                 265                 270

```
Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
        290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
        355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
        435                 440                 445

Glu Lys Gln Lys Pro Glu Met Ile Thr Phe Tyr Asn Ser Thr Lys Ala
    450                 455                 460

Gly Val Asp Val Val Asp Glu Leu Gln Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Lys
        515                 520                 525

Glu His Leu His Ser Arg Asn Lys Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Ile
    610

<210> SEQ ID NO 87
<211> LENGTH: 610
<212> TYPE: PRT
<213> ORGANISM: Artificial sequence
<220> FEATURE:
<223> OTHER INFORMATION: Synthetic

<400> SEQUENCE: 87

Met Asp Ile Glu Arg Gln Glu Glu Arg Ile Arg Ala Met Leu Glu Glu
1               5                   10                  15
```

-continued

```
Glu Leu Ser Asp Tyr Ser Asp Glu Ser Ser Glu Asp Thr Asp
            20              25              30
His Cys Ser Glu His Glu Val Asn Tyr Asp Thr Glu Glu Arg Ile
        35              40              45
Asp Ser Val Asp Val Pro Ser Asn Ser Arg Gln Glu Glu Ala Asn Ala
    50              55              60
Ile Ile Ala Asn Glu Ser Asp Ser Asp Pro Asp Asp Leu Pro Leu
65              70              75              80
Ser Leu Val Arg Gln Arg Ala Ser Ala Ser Arg Ala Val Ser Gly Pro
                85              90              95
Phe Tyr Thr Ser Lys Asp Gly Thr Lys Trp Tyr Lys Asn Cys Gln Arg
            100             105             110
Pro Asn Val Arg Leu Arg Ser Glu Asn Ile Val Thr Glu Gln Ala Gln
            115             120             125
Val Lys Asn Ile Ala Arg Asp Ala Ser Thr Glu Tyr Glu Cys Trp Asn
        130             135             140
Ile Phe Val Thr Ser Asp Met Leu Gln Glu Ile Leu Thr His Thr Asn
145             150             155             160
Ser Ser Ile Arg His Arg Gln Thr Lys Thr Ala Ala Glu Asn Ser Ser
            165             170             175
Ala Glu Thr Ser Phe Tyr Met Gln Glu Thr Thr Leu Cys Glu Leu Lys
            180             185             190
Ala Leu Ile Gly Leu Leu Tyr Ile Ala Gly Leu Ile Lys Ser Asn Arg
            195             200             205
Gln Ser Leu Lys Asp Leu Trp Arg Thr Asp Gly Thr Gly Val Asp Ile
    210             215             220
Phe Arg Thr Thr Met Ser Leu Gln Arg Phe Gln Phe Leu Leu Asn Asn
225             230             235             240
Ile Arg Phe Asp Asp Lys Ser Thr Arg Asp Glu Arg Lys Gln Thr Asp
                245             250             255
Asn Met Ala Ala Phe Arg Ser Ile Phe Asp Gln Phe Val Gln Ser Cys
            260             265             270
Gln Asn Ala Tyr Ser Pro Ser Glu Phe Leu Thr Ile Asp Glu Met Leu
        275             280             285
Leu Ser Phe Arg Gly Arg Cys Leu Phe Arg Val Tyr Ile Pro Asn Lys
    290             295             300
Pro Ala Lys Tyr Gly Ile Lys Ile Leu Ala Leu Val Asp Ala Lys Asn
305             310             315             320
Phe Tyr Val Lys Asn Leu Glu Val Tyr Ala Gly Lys Gln Pro Ser Gly
            325             330             335
Pro Tyr Ala Val Ser Asn Arg Pro Phe Glu Val Val Glu Arg Leu Ile
            340             345             350
Gln Pro Val Ala Arg Ser His Arg Asn Val Thr Phe Asp Asn Trp Phe
        355             360             365
Thr Gly Tyr Glu Leu Met Leu His Leu Leu Asn Glu Tyr Arg Leu Thr
    370             375             380
Ser Val Gly Thr Val Arg Lys Asn Lys Arg Gln Ile Pro Glu Ser Phe
385             390             395             400
Ile Arg Thr Asp Arg Gln Pro Asn Ser Ser Val Phe Gly Phe Gln Lys
                405             410             415
Asp Ile Thr Leu Val Ser Tyr Ala Pro Lys Lys Asn Lys Val Val Val
            420             425             430
Val Met Ser Thr Met His His Asp Asn Ser Ile Asp Glu Ser Thr Gly
```

```
              435                 440                 445
Glu Lys Gln Lys Pro Glu Met Ile Thr Phe Tyr Asn Ser Thr Lys Ala
450                 455                 460
Gly Val Asp Val Val Asp Glu Leu Cys Ala Asn Tyr Asn Val Ser Arg
465                 470                 475                 480
Asn Ser Lys Arg Trp Pro Met Thr Leu Phe Tyr Gly Val Leu Asn Met
                485                 490                 495
Ala Ala Ile Asn Ala Cys Ile Ile Tyr Arg Cys Asn Lys Asn Val Thr
                500                 505                 510
Ile Lys Arg Thr Glu Phe Ile Arg Ser Leu Gly Leu Ser Met Ile Tyr
                515                 520                 525
Glu His Leu His Ser Arg Asn Lys Lys Asn Ile Pro Thr Tyr Leu
530                 535                 540
Arg Gln Arg Ile Glu Lys Gln Leu Gly Glu Pro Ser Pro Arg His Val
545                 550                 555                 560
Asn Val Pro Gly Arg Tyr Val Arg Cys Gln Asp Cys Pro Tyr Lys Lys
                565                 570                 575
Asp Arg Lys Thr Lys Arg Ser Cys Asn Ala Cys Ala Lys Pro Ile Cys
                580                 585                 590
Met Glu His Ala Lys Phe Leu Cys Glu Asn Cys Ala Glu Leu Asp Ser
                595                 600                 605
Ser Leu
    610

<210> SEQ ID NO 88
<211> LENGTH: 610
<212> TYPE: PRT
<213> ORGANISM: Artificial sequence
<220> FEATURE:
<223> OTHER INFORMATION: Synthetic

<400> SEQUENCE: 88

Met Asp Ile Glu Arg Gln Glu Glu Arg Ile Arg Ala Met Leu Glu Glu
1               5                   10                  15
Glu Leu Ser Asp Tyr Ser Asp Glu Ser Ser Ser Glu Asp Glu Thr Asp
                20                  25                  30
His Cys Ser Glu His Glu Val Asn Tyr Asp Thr Glu Glu Glu Arg Ile
                35                  40                  45
Asp Ser Val Asp Val Pro Ser Asn Ser Arg Gln Glu Glu Ala Asn Ala
                50                  55                  60
Ile Ile Ala Asn Glu Ser Asp Ser Asp Pro Asp Asp Leu Pro Leu
65                  70                  75                  80
Ser Leu Val Arg Gln Arg Ala Ser Ala Ser Arg Gln Met Ser Gly Pro
                85                  90                  95
His Tyr Thr Ser Lys Asp Gly Thr Lys Trp Tyr Lys Asn Cys Gln Arg
                100                 105                 110
Pro Asn Val Arg Leu Arg Ser Glu Asn Ile Val Thr Glu Gln Ala Gln
                115                 120                 125
Val Lys Asn Ile Ala Arg Asp Ala Ser Thr Glu Tyr Glu Cys Trp Asn
130                 135                 140
Ile Phe Val Thr Ser Asp Met Leu Gln Glu Ile Leu Thr His Thr Asn
145                 150                 155                 160
Ser Ser Ile Arg Trp Arg Gln Thr Lys Thr Ala Ala Glu Asn Ser Ser
                165                 170                 175
Ala Ser Thr Ser Phe Tyr Met Gln Glu Thr Thr Leu Cys Glu Leu Lys
```

```
                180                 185                 190
Ala Leu Ile Gly Leu Leu Tyr Ile Ala Gly Leu Ile Lys Ser Asn Arg
            195                 200                 205

Gln Ser Leu Lys Asp Leu Trp Arg Thr Asp Thr Gly Val Asp Ile
        210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
                260                 265                 270

Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
        290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
        370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
                420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
        450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
                500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
        530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605
```

His Leu
    610

<210> SEQ ID NO 89
<211> LENGTH: 610
<212> TYPE: PRT
<213> ORGANISM: Artificial sequence
<220> FEATURE:
<223> OTHER INFORMATION: Synthetic

<400> SEQUENCE: 89

Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
        50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Ser Thr Ser Phe Tyr Met Gln Glu Thr Thr Leu Cys Glu Leu Lys
                180                 185                 190

Ala Leu Ile Gly Leu Leu Tyr Ile Ala Gly Leu Ile Lys Ser Asn Arg
                195                 200                 205

Gln Ser Leu Lys Asp Leu Trp Arg Thr Asp Gly Thr Gly Val Asp Ile
        210                 215                 220

Phe Arg Thr Thr Met Ser Leu Gln Arg Phe Gln Phe Leu Leu Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Asp Gln Phe Val Gln Ser Cys
                260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
        290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
            530                 535                 540

Arg Gln Arg Ile Ala Met Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
            595                 600                 605

Ser Leu
    610

<210> SEQ ID NO 90
<211> LENGTH: 610
<212> TYPE: PRT
<213> ORGANISM: Artificial sequence
<220> FEATURE:
<223> OTHER INFORMATION: Synthetic

<400> SEQUENCE: 90

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Glu Arg Ile
            35                  40                  45

Asp Ser Val Asp Val Pro Ser Asn Ser Arg Gln Glu Glu Ala Asn Ala
            50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

```
Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Gly Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Gly Leu Leu Tyr Ile Ala Gly Leu Ile Lys Ser Asn Arg
            195                 200                 205

Gln Ser Leu Lys Asp Leu Trp Arg Thr Asp Gly Thr Gly Val Asp Ile
            210                 215                 220

Phe Arg Thr Thr Met Ser Leu Gln Arg Phe Gln Phe Leu Leu Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
            290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
            370                 375                 380

Ser Val Gly Thr Val Arg Lys Asn Lys Thr Gln Ile Pro Glu Asn Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Val Asp Glu Leu Gln Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510
```

```
Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
                580                 585                 590

Met Glu His Ala Lys Phe Leu Cys Glu Asn Cys Ala Glu Leu Asp Ser
                595                 600                 605

Ser Leu
    610

<210> SEQ ID NO 91
<211> LENGTH: 610
<212> TYPE: PRT
<213> ORGANISM: Artificial sequence
<220> FEATURE:
<223> OTHER INFORMATION: Synthetic

<400> SEQUENCE: 91

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Gly Leu Leu Tyr Leu Ala Gly Leu Ile Lys Ser Asn Arg
            195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255
```

```
Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
        370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
        435                 440                 445

Glu Lys Gln Lys Pro Glu Met Ile Thr Phe Tyr Asn Ser Thr Lys Ala
450                 455                 460

Gly Val Asp Val Val Asp Glu Leu Gln Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Lys
        515                 520                 525

Glu His Leu His Ser Arg Asn Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Tyr Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 92
<211> LENGTH: 610
<212> TYPE: PRT
<213> ORGANISM: Artificial sequence
<220> FEATURE:
<223> OTHER INFORMATION: Synthetic

<400> SEQUENCE: 92
```

```
Met Asp Ile Glu Arg Gln Glu Glu Arg Ile Arg Ala Met Leu Glu Glu
1               5                   10                  15

Glu Leu Ser Asp Tyr Ser Asp Ser Ser Glu Asp Glu Thr Asp
            20                  25                  30

His Cys Ser Glu His Glu Val Asn Tyr Asp Thr Glu Glu Arg Ile
        35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg Trp Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Gly Leu Leu Tyr Ile Ala Gly Leu Ile Lys Ser Asn Arg
                195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
                260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
    355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
```

```
                420             425             430
    Val Met Ser Thr Met His His Asp Asn Ser Ile Asp Glu Ser Thr Gly
                435             440             445

Glu Lys Gln Lys Pro Glu Met Ile Thr Phe Tyr Asn Ser Thr Lys Ala
                450             455             460

Gly Val Asp Val Val Asp Glu Leu Cys Ala Asn Tyr Asn Val Ser Arg
    465             470             475             480

Asn Ser Lys Arg Trp Pro Met Thr Leu Phe Tyr Gly Val Leu Asn Met
                485             490             495

Ala Ala Ile Asn Ala Cys Ile Ile Tyr Arg Thr Asn Lys Asn Val Thr
                500             505             510

Ile Lys Arg Thr Glu Phe Ile Arg Ser Leu Gly Leu Ser Met Ile Tyr
                515             520             525

Glu His Leu His Ser Arg Asn Lys Lys Asn Ile Pro Thr Tyr Leu
                530             535             540

Arg Gln Arg Ile Glu Lys Gln Leu Gly Glu Pro Ser Pro Arg His Val
    545             550             555             560

Asn Val Pro Gly Arg Tyr Val Arg Cys Gln Asp Cys Pro Tyr Lys Lys
                565             570             575

Asp Arg Lys Thr Lys Arg Ser Cys Asn Ala Cys Ala Lys Pro Ile Cys
                580             585             590

Met Glu His Ala Lys Phe Leu Cys Glu Asn Cys Ala Glu Leu Asp Ser
                595             600             605

Ser Leu
        610

<210> SEQ ID NO 93
<211> LENGTH: 610
<212> TYPE: PRT
<213> ORGANISM: Artificial sequence
<220> FEATURE:
<223> OTHER INFORMATION: Synthetic

<400> SEQUENCE: 93

Met Asp Ile Glu Arg Gln Glu Glu Arg Ile Arg Ala Met Leu Glu Glu
    1               5               10              15

Glu Leu Ser Asp Tyr Ser Asp Glu Ser Ser Ser Glu Asp Glu Thr Asp
                20              25              30

His Cys Ser Glu His Glu Val Asn Tyr Asp Thr Glu Glu Glu Arg Ile
                35              40              45

Asp Ser Val Asp Val Pro Ser Asn Ser Arg Gln Glu Glu Ala Asn Ala
    50              55              60

Ile Ile Ala Asn Glu Ser Asp Ser Asp Pro Asp Asp Leu Pro Leu
    65              70              75              80

Ser Leu Val Arg Gln Arg Ala Ser Ala Ser Arg Gln Val Ser Gly Pro
                85              90              95

Phe Tyr Thr Ser Lys Asp Gly Thr Lys Trp Tyr Lys Asn Cys Gln Arg
                100             105             110

Pro Asn Val Arg Leu Arg Ser Glu Asn Ile Val Thr Glu Gln Ala Gln
                115             120             125

Val Lys Asn Ile Ala Arg Asp Ala Ser Thr Glu Tyr Glu Cys Trp Asn
                130             135             140

Ile Phe Val Thr Ser Asp Met Leu Gln Glu Ile Leu Thr His Thr Asn
    145             150             155             160

Ser Ser Ile Arg Trp Arg Gln Thr Lys Thr Ala Ala Glu Asn Ser Ser
```

```
            165                 170                 175
Ala Glu Thr Ser Phe Tyr Met Gln Glu Thr Thr Leu Cys Glu Leu Lys
            180                 185                 190
Ala Leu Ile Gly Leu Leu Tyr Leu Ala Gly Leu Ile Lys Ser Asn Arg
            195                 200                 205
Gln Ser Leu Lys Asp Leu Trp Arg Thr Asp Gly Thr Gly Val Asp Ile
            210                 215                 220
Phe Arg Thr Thr Met Ser Leu Gln Arg Phe Gln Phe Leu Gln Asn Asn
225                 230                 235                 240
Ile Arg Phe Asp Asp Lys Ser Thr Arg Asp Glu Arg Lys Gln Thr Asp
            245                 250                 255
Asn Met Ala Ala Phe Arg Ser Ile Phe Asp Gln Phe Val Gln Ser Cys
            260                 265                 270
Gln Asn Ala Tyr Ser Pro Ser Glu Phe Leu Thr Ile Asp Glu Met Leu
            275                 280                 285
Leu Ser Phe Arg Gly Arg Cys Leu Phe Arg Val Tyr Ile Pro Asn Lys
            290                 295                 300
Pro Ala Lys Tyr Gly Ile Lys Ile Leu Ala Leu Val Asp Ala Lys Asn
305                 310                 315                 320
Phe Tyr Val Val Asn Leu Glu Val Tyr Ala Gly Lys Gln Pro Ser Gly
            325                 330                 335
Pro Tyr Ala Val Ser Asn Arg Pro Phe Glu Val Val Arg Leu Ile
            340                 345                 350
Gln Pro Val Ala Arg Ser His Arg Asn Val Thr Phe Asp Asn Trp Phe
            355                 360                 365
Thr Gly Tyr Glu Leu Met Leu His Leu Leu Asn Glu Tyr Arg Leu Thr
            370                 375                 380
Ser Val Gly Thr Val Arg Lys Asn Lys Arg Gln Ile Pro Glu Ser Phe
385                 390                 395                 400
Ile Arg Thr Asp Arg Gln Pro Asn Ser Ser Val Phe Gly Phe Gln Lys
            405                 410                 415
Asp Ile Thr Leu Val Ser Tyr Ala Pro Lys Lys Asn Lys Val Val Val
            420                 425                 430
Val Met Ser Thr Met His His Asp Asn Ser Ile Asp Glu Ser Thr Gly
            435                 440                 445
Glu Lys Gln Lys Pro Glu Met Ile Thr Phe Tyr Asn Ser Thr Lys Ala
            450                 455                 460
Gly Val Asp Val Val Asp Glu Leu Cys Ala Asn Tyr Asn Val Ser Arg
465                 470                 475                 480
Asn Ser Lys Arg Trp Pro Met Thr Leu Phe Tyr Gly Val Leu Asn Met
            485                 490                 495
Ala Ala Ile Asn Ala Cys Ile Ile Tyr Arg Thr Asn Lys Asn Val Thr
            500                 505                 510
Ile Lys Arg Thr Glu Phe Ile Arg Ser Leu Gly Leu Ser Met Ile Lys
            515                 520                 525
Glu His Leu His Ser Arg Asn Lys Lys Asn Ile Pro Thr Tyr Leu
            530                 535                 540
Arg Gln Arg Ile Glu Lys Gln Leu Gly Glu Pro Ser Pro Arg His Val
545                 550                 555                 560
Asn Tyr Pro Gly Arg Tyr Val Arg Cys Gln Asp Cys Pro Tyr Lys Lys
            565                 570                 575
Asp Arg Lys Thr Lys Arg Ser Cys Asn Ala Cys Ala Lys Pro Ile Cys
            580                 585                 590
```

```
Met Glu His Ala Lys Phe Leu Cys Glu Asn Cys Ala Glu Leu His Ser
            595                 600                 605

Ser Leu
    610

<210> SEQ ID NO 94
<211> LENGTH: 610
<212> TYPE: PRT
<213> ORGANISM: Artificial sequence
<220> FEATURE:
<223> OTHER INFORMATION: Synthetic

<400> SEQUENCE: 94

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Arg Ile
        35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
        115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Gly Leu Leu Tyr Leu Ala Gly Leu Ile Lys Ser Asn Arg
        195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
                325                 330                 335
```

```
Pro Tyr Ala Val Ser Asn Arg Pro Phe Glu Val Glu Arg Leu Ile
            340                 345                 350

Gln Pro Val Ala Arg Ser His Arg Asn Val Thr Phe Asp Asn Trp Phe
        355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Ser Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
        515                 520                 525

Glu His Leu His Ser Arg Asn Lys Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 95
<211> LENGTH: 610
<212> TYPE: PRT
<213> ORGANISM: Artificial sequence
<220> FEATURE:
<223> OTHER INFORMATION: Synthetic

<400> SEQUENCE: 95

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Glu Arg Ile
        35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80
```

-continued

```
Ser Leu Val Arg Gln Arg Ala Ser Ala Ser Arg Gln Val Ser Gly Pro
            85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
            165                 170                 175

Ala Glu Thr Ser Phe Tyr Met Gln Glu Thr Thr Leu Cys Glu Leu Lys
            180                 185                 190

Ala Leu Ile Gly Leu Leu Tyr Ile Ala Gly Leu Ile Lys Ser Asn Arg
            195                 200                 205

Gln Ser Leu Lys Asp Leu Trp Arg Thr Asp Gly Thr Gly Val Asp Ile
            210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
            245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
            290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Ala Gly Lys Gln Pro Ser Gly
            325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
            370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
            405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
            485                 490                 495
```

Ala Ala Ile Asn Ala Cys Ile Ile Tyr Arg Thr Asn Lys Asn Val Thr
                500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
        530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 96
<211> LENGTH: 610
<212> TYPE: PRT
<213> ORGANISM: Artificial sequence
<220> FEATURE:
<223> OTHER INFORMATION: Synthetic

<400> SEQUENCE: 96

Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Glu Arg Ile
        35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
        115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Gly Leu Leu Tyr Ile Ala Gly Leu Ile Lys Ser Asn Arg
        195                 200                 205

Gln Ser Leu Lys Asp Leu Tyr Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

```
Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
        355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
        435                 440                 445

Glu Lys Gln Lys Pro Glu Met Ile Thr Phe Tyr Asn Ser Thr Lys Ala
    450                 455                 460

Gly Val Asp Val Val Asp Glu Leu Gln Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
        515                 520                 525

Glu His Leu His Ser Arg Asn Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Tyr Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 97
<211> LENGTH: 610
<212> TYPE: PRT
<213> ORGANISM: Artificial sequence
<220> FEATURE:
<223> OTHER INFORMATION: Synthetic
```

<400> SEQUENCE: 97

```
Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Ala Leu Leu Tyr Ile Ala Gly Leu Ile Lys Ser Asn Arg
            195                 200                 205

Gln Ser Leu Lys Asp Leu Trp Arg Lys Asp Gly Thr Gly Val Asp Ile
    210                 215                 220

Phe Arg Thr Thr Met Ser Leu Gln Arg Phe Gln Phe Leu Leu Asn Asn
225                 230                 235                 240

Ile Arg Phe Asp Asp Ile Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val His Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
    355                 360                 365

Thr Gly Tyr Glu Leu Met Leu His Leu Leu Asn Glu Tyr Arg Leu Thr
                370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
```

```
                        405                 410                 415
Asp Ile Thr Leu Val Ser Tyr Ala Pro Lys Lys Asn Lys Val Val Val
                    420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480

Asn Ser Lys Lys Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
            530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Gly Asn Cys Ala Glu Leu Asp Ser
            595                 600                 605

Ser Leu
    610

<210> SEQ ID NO 98
<211> LENGTH: 610
<212> TYPE: PRT
<213> ORGANISM: Artificial sequence
<220> FEATURE:
<223> OTHER INFORMATION: Synthetic

<400> SEQUENCE: 98

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Glu Arg Ile
            35                  40                  45

Asp Ser Val Asp Val Pro Ser Asn Ser Arg Gln Glu Glu Ala Asn Ala
        50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Gly Tyr Glu Cys Trp Asn
        130                 135                 140

Ile Phe Val Thr Ser Asp Met Leu Gln Glu Ile Leu Thr His Thr Asn
```

```
            145                 150                 155                 160
        Ser Ser Ile Arg His Arg Gln Thr Lys Thr Ala Ala Glu Asn Ser Ser
                        165                 170                 175
        Ala Glu Thr Ser Phe Tyr Met Gln Glu Thr Thr Leu Cys Glu Leu Lys
                        180                 185                 190
        Ala Leu Ile Ala Leu Leu Tyr Ile Ala Gly Leu Ile Lys Ser Asn Arg
                        195                 200                 205
        Gln Ser Leu Lys Asp Leu Trp Arg Thr Asp Gly Thr Gly Val Asp Ile
                210                 215                 220
        Phe Arg Thr Thr Met Ser Leu Gln Arg Phe Gln Phe Leu Ile Asn Asn
        225                 230                 235                 240
        Ile Arg Phe Asp Asp Lys Ser Thr Arg Asp Glu Arg Lys Gln Thr Asp
                        245                 250                 255
        Asn Met Ala Ala Phe Arg Ser Ile Phe Asp Gln Phe Val Gln Cys Cys
                        260                 265                 270
        Gln Asn Ala Tyr Ser Pro Ser Glu Phe Leu Thr Ile Asp Glu Met Leu
                        275                 280                 285
        Leu Ser Phe Arg Gly Arg Cys Leu Phe Arg Val Tyr Ile Pro Asn Lys
                290                 295                 300
        Pro Ala Lys Tyr Gly Ile Lys Ile Leu Ala Leu Val Asp Ala Lys Asn
        305                 310                 315                 320
        Trp Tyr Val Val Asn Leu Glu Val Tyr Ala Gly Lys Gln Pro Ser Gly
                        325                 330                 335
        Pro Tyr Ala Val Ser Asn Arg Pro Phe Glu Val Val Glu Arg Leu Ile
                        340                 345                 350
        Gln Pro Val Ala Arg Ser His Arg Asn Val Thr Phe Asp Asn Trp Phe
                        355                 360                 365
        Thr Gly Tyr Glu Leu Met Leu His Leu Leu Asn Glu Tyr Arg Leu Thr
                370                 375                 380
        Ser Val Gly Thr Val Arg Lys Asn Lys Arg Gln Ile Pro Glu Ser Phe
        385                 390                 395                 400
        Ile Arg Thr Asp Arg Gln Pro Asn Ser Ser Val Phe Gly Phe Gln Lys
                        405                 410                 415
        Asp Ile Thr Leu Val Ser Tyr Ala Pro Lys Lys Asn Lys Val Val Val
                        420                 425                 430
        Val Met Ser Thr Met His His Asp Asn Ser Ile Asp Glu Ser Thr Gly
                        435                 440                 445
        Glu Lys Gln Lys Pro Glu Met Ile Thr Phe Tyr Asn Ser Thr Lys Ala
                450                 455                 460
        Gly Val Asp Val Val Asp Glu Leu Cys Ala Asn Tyr Asn Val Ser Arg
        465                 470                 475                 480
        Asn Ser Lys Arg Trp Pro Met Thr Leu Phe Tyr Gly Val Leu Asn Met
                        485                 490                 495
        Ala Ala Ile Asn Ala Cys Ile Ile Tyr Arg Thr Asn Lys Asn Val Thr
                        500                 505                 510
        Ile Lys Arg Thr Glu Phe Ile Arg Ser Leu Gly Leu Ser Met Ile Tyr
                        515                 520                 525
        Glu His Leu His Ser Arg Asn Lys Lys Asn Ile Pro Thr Tyr Leu
                530                 535                 540
        Arg Gln Arg Ile Glu Lys Gln Leu Gly Glu Pro Ser Pro Arg His Val
        545                 550                 555                 560
        Asn Val Pro Gly Arg Tyr Val Arg Cys Gln Asp Cys Pro Tyr Lys Lys
                        565                 570                 575
```

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
            595                 600                 605

Ser Leu
    610

<210> SEQ ID NO 99
<211> LENGTH: 610
<212> TYPE: PRT
<213> ORGANISM: Artificial sequence
<220> FEATURE:
<223> OTHER INFORMATION: Synthetic

<400> SEQUENCE: 99

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
            85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
            165                 170                 175

Ala Glu Thr Ser Phe Tyr Met Gln Glu Thr Thr Leu Cys Glu Leu Lys
            180                 185                 190

Ala Leu Ile Ala Leu Leu Tyr Leu Ala Gly Leu Ile Lys Ser Asn Arg
            195                 200                 205

Gln Ser Ala Lys Asp Leu Trp Arg Thr Asp Gly Thr Gly Val Asp Ile
    210                 215                 220

Phe Arg Thr Thr Met Ser Leu Gln Arg Phe Tyr Phe Leu Gln Asn Asn
225                 230                 235                 240

Ile Arg Phe Asp Asp Lys Ser Thr Arg Asp Glu Arg Lys Gln Thr Asp
            245                 250                 255

Asn Met Ala Ala Phe Arg Ser Ile Phe Asp Gln Phe Val Gln Cys Cys
            260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
            290                 295                 300

Pro Ala Lys Tyr Gly Ile Lys Ile Leu Ala Leu Val Asp Ala Lys Asn
305                 310                 315                 320

-continued

```
Phe Tyr Val Lys Asn Leu Glu Val Tyr Ala Gly Lys Gln Pro Ser Gly
            325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
            370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
            405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
            485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Asn Ile Pro Thr Tyr Leu
            530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
            565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
            595                 600                 605

Ser Leu
    610

<210> SEQ ID NO 100
<211> LENGTH: 610
<212> TYPE: PRT
<213> ORGANISM: Artificial sequence
<220> FEATURE:
<223> OTHER INFORMATION: Synthetic

<400> SEQUENCE: 100

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Glu Arg Ile
            35                  40                  45

Asp Ser Val Asp Val Pro Ser Asn Ser Arg Gln Glu Glu Ala Asn Ala
        50                  55                  60
```

```
Ile Ile Ala Asn Glu Ser Asp Ser Asp Pro Asp Asp Leu Pro Leu
 65                  70                  75                  80

Ser Leu Val Arg Gln Arg Ala Ser Ala Ser Arg Gln Val Ser Gly Pro
             85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Thr Thr Leu Pro Glu Leu Lys
            180                 185                 190

Ala Leu Ile Ala Leu Leu Tyr Leu Ala Gly Leu Ile Lys Ser Asn Arg
            195                 200                 205

Gln Ser Leu Lys Asp Leu Trp Arg Thr Asp Thr Gly Val Asp Val
210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
            275                 280                 285

Leu Ser Phe Arg Gly Arg Cys Leu Phe Arg Val Tyr Ile Pro Asn Lys
290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Val Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
            405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480
```

```
Asn Ser Lys Arg Trp Pro Met Thr Leu Phe Tyr Gly Val Leu Asn Met
            485                 490                 495

Ala Ala Ile Asn Ala Cys Ile Ile Tyr Arg Thr Asn Lys Asn Val Thr
        500                 505                 510

Ile Lys Arg Thr Glu Phe Ile Arg Ser Leu Gly Leu Ser Met Ile Tyr
        515                 520                 525

Glu His Leu His Ser Arg Asn Lys Lys Asn Ile Pro Thr Tyr Leu
        530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 101
<211> LENGTH: 610
<212> TYPE: PRT
<213> ORGANISM: Artificial sequence
<220> FEATURE:
<223> OTHER INFORMATION: Synthetic

<400> SEQUENCE: 101

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Ser Glu Asp Glu Thr Asp
            20                  25                  30

His Cys Ser Glu His Glu Val Asn Tyr Asp Thr Glu Glu Glu Arg Ile
        35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
        115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg Glu Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Ala Leu Leu Tyr Leu Ala Gly Leu Ile Lys Ser Asn Arg
        195                 200                 205

Gln Ser Leu Lys Asp Leu Trp Arg Thr Asp Gly Thr Gly Val Asp Ile
    210                 215                 220
```

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
            245                 250                 255

Asn Met Ala Ala Phe Arg Ser Ile Phe Asp Gln Phe Val Gln Cys Cys
        260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
290                 295                 300

Pro Ala Lys Tyr Gly Ile Lys Ile Leu Ala Leu Val Asp Ala Lys Asn
305                 310                 315                 320

Phe Tyr Val Lys Asn Leu Glu Val Tyr Val Gly Lys Gln Pro Ser Gly
            325                 330                 335

Pro Tyr Ala Val Ser Asn Arg Pro Phe Glu Val Val Glu Arg Leu Ile
        340                 345                 350

Gln Pro Val Ala Arg Ser His Arg Asn Val Thr Phe Asp Asn Trp Phe
    355                 360                 365

Thr Gly Tyr Glu Leu Met Leu His Leu Leu Asn Glu Tyr Arg Leu Thr
370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
            405                 410                 415

Asp Ile Thr Leu Val Ser Tyr Ala Pro Lys Lys Asn Lys Val Val Val
        420                 425                 430

Val Met Ser Thr Met His His Asp Asn Ser Ile Asp Glu Ser Thr Gly
    435                 440                 445

Glu Lys Gln Lys Pro Glu Met Ile Thr Phe Tyr Asn Ser Thr Lys Ala
450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
            485                 490                 495

Ala Ala Ile Asn Ala Cys Ile Ile Tyr Arg Thr Asn Lys Asn Val Thr
        500                 505                 510

Ile Lys Arg Thr Glu Phe Ile Arg Ser Leu Gly Leu Ser Met Ile Tyr
    515                 520                 525

Glu His Leu His Ser Arg Asn Lys Lys Asn Ile Pro Thr Tyr Leu
530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
            565                 570                 575

Asp Arg Lys Thr Lys Arg Ser Cys Asn Ala Cys Ala Lys Pro Ile Cys
        580                 585                 590

Met Glu His Ala Lys Phe Leu Cys Glu Asn Cys Ala Glu Leu Asp Ser
    595                 600                 605

Ser Leu
    610

<210> SEQ ID NO 102
<211> LENGTH: 610
<212> TYPE: PRT

<213> ORGANISM: Artificial sequence
<220> FEATURE:
<223> OTHER INFORMATION: Synthetic

<400> SEQUENCE: 102

```
Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Ala Leu Leu Tyr Leu Ala Gly Leu Ile Lys Ser Asn Arg
                195                 200                 205

Gln Ser Leu Lys Asp Leu Trp Arg Thr Asp Gly Thr Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Ile Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
290                 295                 300

Pro Ala Lys Tyr Gly Ile Lys Ile Leu Ala Leu Val Asp Ala Lys Asn
305                 310                 315                 320

Asp Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
                355                 360                 365

Thr Gly Tyr Glu Leu Met Leu His Leu Leu Asn Glu Tyr Arg Leu Thr
370                 375                 380

Ser Val Gly Thr Val Arg Lys Asn Lys Arg Gln Ile Pro Glu Ser Phe
```

```
                385                 390                 395                 400
Ile Arg Thr Asp Arg Gln Pro Asn Ser Ser Val Phe Gly Phe Gln Lys
                    405                 410                 415

Asp Ile Thr Leu Val Ser Tyr Ala Pro Lys Lys Asn Lys Val Val Val
                420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
        450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
                    500                 505                 510

Ile Lys Arg Thr Glu Phe Ile Arg Ser Leu Gly Leu Ser Met Ile Tyr
                515                 520                 525

Glu His Leu His Ser Arg Asn Lys Lys Asn Ile Pro Thr Tyr Leu
        530                 535                 540

Arg Gln Arg Ile Glu Lys Gln Leu Gly Glu Pro Ser Pro Arg His Val
545                 550                 555                 560

Asn Tyr Pro Gly Arg Tyr Val Arg Cys Gln Asp Cys Pro Tyr Lys Lys
                    565                 570                 575

Asp Arg Lys Thr Lys Arg Ser Cys Asn Ala Cys Ala Lys Pro Ile Cys
                580                 585                 590

Met Glu His Ala Lys Phe Leu Cys Glu Asn Cys Ala Glu Leu Asp Ser
            595                 600                 605

Ser Leu
    610

<210> SEQ ID NO 103
<211> LENGTH: 610
<212> TYPE: PRT
<213> ORGANISM: Artificial sequence
<220> FEATURE:
<223> OTHER INFORMATION: Synthetic

<400> SEQUENCE: 103

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
```

```
                130             135             140
Ile Phe Val Thr Ser Asp Met Leu Gln Glu Ile Leu Thr His Thr Asn
145             150             155             160

Ser Ser Ile Arg His Arg Gln Thr Lys Thr Ala Ala Glu Asn Ser Ser
            165             170             175

Ala Glu Thr Ser Phe Tyr Met Gln Glu Thr Thr Leu Cys Glu Leu Lys
        180             185             190

Ala Leu Ile Gly Leu Leu Tyr Leu Ala Gly Leu Ile Lys Ser Asn Arg
            195             200             205

Gln Ser Leu Lys Asp Leu Tyr Arg Thr Asp Gly Thr Gly Val Asp Ile
        210             215             220

Phe Arg Thr Thr Met Ser Leu Gln Arg Phe Gly Phe Leu Gln Asn Asn
225             230             235             240

Ile Arg Phe Asp Asp Lys Ser Thr Arg Asp Glu Arg Lys Gln Thr Asp
            245             250             255

Asn Met Ala Ala Phe Arg Ser Ile Phe Asp Gln Phe Val Gln Cys Cys
        260             265             270

Gln Asn Ala Tyr Ser Pro Ser Glu Phe Leu Thr Ile Asp Glu Met Leu
        275             280             285

Leu Ser Phe Arg Gly Arg Cys Leu Phe Arg Val Tyr Ile Pro Asn Lys
        290             295             300

Pro Ala Lys Tyr Gly Ile Lys Ile Leu Ala Leu Val Asp Ala Lys Asn
305             310             315             320

Phe Tyr Val Val Asn Leu Glu Val Tyr Ala Gly Lys Gln Pro Ser Gly
            325             330             335

Pro Tyr Ala Val Ser Asn Arg Pro Phe Glu Val Val Glu Arg Leu Ile
            340             345             350

Gln Pro Val Ala Arg Ser His Arg Asn Val Thr Phe Asp Asn Trp Phe
            355             360             365

Thr Gly Tyr Glu Leu Met Leu His Leu Leu Asn Glu Tyr Arg Leu Thr
            370             375             380

Ser Val Gly Thr Val Arg Lys Asn Lys Arg Gln Ile Pro Glu Ser Phe
385             390             395             400

Ile Arg Thr Asp Arg Gln Pro Asn Ser Ser Val Phe Gly Phe Gln Lys
            405             410             415

Asp Ile Thr Leu Val Ser Tyr Ala Pro Lys Lys Asn Lys Val Val Val
            420             425             430

Val Met Ser Thr Met His His Asp Asn Ser Ile Asp Glu Ser Thr Gly
            435             440             445

Glu Lys Gln Lys Pro Glu Met Ile Thr Phe Tyr Asn Ser Thr Lys Ala
450             455             460

Gly Val Asp Val Val Asp Glu Leu Cys Ala Asn Tyr Asn Val Ser Arg
465             470             475             480

Asn Ser Lys Arg Trp Pro Met Thr Leu Phe Tyr Gly Val Leu Asn Met
            485             490             495

Ala Ala Ile Asn Ala Cys Ile Ile Tyr Arg Thr Asn Lys Asn Val Thr
            500             505             510

Ile Lys Arg Thr Glu Phe Ile Arg Ser Leu Gly Leu Ser Met Ile Tyr
            515             520             525

Glu His Leu His Ser Arg Asn Lys Lys Asn Ile Pro Thr Tyr Leu
            530             535             540

Arg Gln Arg Ile Glu Lys Gln Leu Gly Glu Pro Ser Pro Arg His Val
545             550             555             560
```

```
Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
                580                 585                 590

Met Glu His Ala Lys Phe Leu Cys Glu Asn Cys Ala Glu Leu Asp Ser
                595                 600                 605

Ser Leu
    610

<210> SEQ ID NO 104
<211> LENGTH: 610
<212> TYPE: PRT
<213> ORGANISM: Artificial sequence
<220> FEATURE:
<223> OTHER INFORMATION: Synthetic

<400> SEQUENCE: 104

Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
                20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
        50                  55                  60

Ile Ile Ala Asn Glu Ser Asp Ser Asp Pro Asp Asp Leu Pro Leu
65                  70                  75              80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Gly Leu Leu Tyr Leu Ala Gly Leu Ile Lys Ser Asn Arg
        195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300
```

```
Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
            325                 330                 335

Pro Tyr Ala Val Ser Asn Arg Pro Phe Glu Val Val Arg Leu Ile
            340                 345                 350

Gln Pro Val Ala Arg Ser His Arg Asn Val Thr Phe Asp Asn Trp Phe
            355                 360                 365

Thr Gly Tyr Glu Leu Met Leu His Leu Leu Asn Glu Tyr Arg Leu Thr
            370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
            405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
            435                 440                 445

Glu Lys Gln Lys Pro Glu Met Ile Thr Phe Tyr Asn Ser Thr Lys Ala
            450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
            485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
            515                 520                 525

Glu His Leu His Ser Arg Asn Lys Lys Lys Asn Ile Pro Thr Ile Leu
            530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
            565                 570                 575

Asp Arg Lys Thr Lys Arg Ser Cys Asn Ala Cys Ala Lys Pro Ile Cys
            580                 585                 590

Met Glu His Ala Lys Phe Leu Cys Val Asn Cys Ala Glu Leu Asp Ser
            595                 600                 605

Ser Leu
    610
```

<210> SEQ ID NO 105
<211> LENGTH: 610
<212> TYPE: PRT
<213> ORGANISM: Artificial sequence
<220> FEATURE:
<223> OTHER INFORMATION: Synthetic

<400> SEQUENCE: 105

```
Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Glu Arg Ile
            35                  40                  45
```

```
Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Gly Leu Leu Tyr Leu Ala Gly Leu Ile Lys Ser Asn Arg
                195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Ser Cys
            260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
    355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
    450                 455                 460
```

```
Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
            485                 490                 495

Ala Ala Ile Asn Ala Cys Ile Ile Tyr Arg Thr Asn Lys Asn Val Thr
        500                 505                 510

Ile Lys Arg Thr Glu Phe Ile Arg Ser Leu Gly Leu Ser Met Ile Tyr
    515                 520                 525

Glu His Leu His Ser Arg Asn Lys Lys Asn Ile Pro Thr Tyr Leu
530                 535                 540

Arg Gln Arg Ile Glu Lys Gln Leu Gly Glu Pro Ser Pro Arg His Val
545             550                 555                 560

Asn Tyr Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
            595                 600                 605

Ser Leu
610
```

<210> SEQ ID NO 106
<211> LENGTH: 610
<212> TYPE: PRT
<213> ORGANISM: Artificial sequence
<220> FEATURE:
<223> OTHER INFORMATION: Synthetic

<400> SEQUENCE: 106

```
Met Asp Ile Glu Arg Gln Glu Glu Arg Ile Arg Ala Met Leu Glu Glu
1               5                   10                  15

Glu Leu Ser Asp Tyr Ser Asp Glu Ser Ser Glu Asp Glu Thr Asp Asp
                20                  25                  30

His Cys Ser Glu His Glu Val Asn Tyr Asp Thr Glu Glu Glu Arg Ile
            35                  40                  45

Asp Ser Val Asp Val Pro Ser Asn Ser Arg Gln Glu Glu Ala Asn Ala
        50                  55                  60

Ile Ile Ala Asn Glu Ser Asp Ser Asp Pro Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Ala Leu Leu Tyr Leu Ala Gly Leu Ile Lys Ser Asn Arg
        195                 200                 205
```

```
Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
                275                 280                 285

Leu Ser Phe Arg Gly Arg Cys Leu Phe Arg Val Tyr Ile Pro Asn Lys
290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
                355                 360                 365

Thr Gly Tyr Glu Cys Met Leu His Leu Leu Asn Glu Tyr Arg Leu Thr
                370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
                420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
                450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
                500                 505                 510

Ile Lys Arg Thr Glu Phe Ile Arg Ser Leu Gly Leu Ser Met Ile Tyr
                515                 520                 525

Glu His Leu His Ser Arg Asn Lys Lys Lys Asn Ile Pro Thr Tyr Leu
                530                 535                 540

Arg Gln Arg Ile Glu Met Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
                580                 585                 590

Met Glu His Ala Lys Phe Leu Cys Glu Asn Cys Ala Glu Leu Lys Ser
                595                 600                 605

Ser Leu
    610
```

```
<210> SEQ ID NO 107
<211> LENGTH: 15
<212> TYPE: DNA
<213> ORGANISM: Artificial sequence
<220> FEATURE:
<223> OTHER INFORMATION: Synthetic

<400> SEQUENCE: 107
cacttggatt gcggg                                                    15

<210> SEQ ID NO 108
<211> LENGTH: 15
<212> TYPE: DNA
<213> ORGANISM: Artificial sequence
<220> FEATURE:
<223> OTHER INFORMATION: Synthetic

<400> SEQUENCE: 108
cccgacaccg tagtg                                                    15

<210> SEQ ID NO 109
<211> LENGTH: 262
<212> TYPE: DNA
<213> ORGANISM: Artificial sequence
<220> FEATURE:
<223> OTHER INFORMATION: Synthetic

<400> SEQUENCE: 109
aaacgagtta agtcggctcg cgtgaattgc gcgtactccg cgggagccgt cttaactcgg    60
ttcatataga tttgcggtgg agtgcgggaa acgtgtaaac tcgggccgat tgtaactgcg   120
tattaccaaa tatttgtttc caagcttggt accgagctcg gatcccgtac gctgcaggtc   180
gacggatccc cgggttaatt aaggcgcgcc agatctgttt agcttgcctc gtccccgccg   240
ggtcacccgg ccagcgacat gg                                           262

<210> SEQ ID NO 110
<211> LENGTH: 227
<212> TYPE: DNA
<213> ORGANISM: Artificial sequence
<220> FEATURE:
<223> OTHER INFORMATION: Synthetic

<400> SEQUENCE: 110
tgtcgaagaa ttcggcggcc gcatgcatct agagaattat ttatgtactg aatagataaa    60
aaaatgtctg tgattgaata aattttcatt ttttacacaa gaaaccgaaa atttcatttc   120
aatcgaaccc atacttcaaa agatataggc attttaaact aactctgatt ttgcgcggga   180
aacctaaata attgcccgcg ccatcttata ttttggcggg aaattca                227

<210> SEQ ID NO 111
<211> LENGTH: 567
<212> TYPE: PRT
<213> ORGANISM: Artificial sequence
<220> FEATURE:
<223> OTHER INFORMATION: Synthetic

<400> SEQUENCE: 111

Met Ser Gln His Ser Asp Tyr Ser Asp Asp Glu Phe Cys Ala Asp Lys
1               5                   10                  15

Leu Ser Asn Tyr Ser Cys Asp Ser Asp Leu Glu Asn Ala Ser Thr Ser
            20                  25                  30

Asp Glu Asp Ser Ser Asp Asp Glu Val Met Val Arg Pro Arg Thr Leu
        35                  40                  45
```

```
Arg Arg Arg Arg Ile Ser Ser Ser Ser Asp Ser Glu Ser Asp Ile
 50                  55                  60

Glu Gly Gly Arg Glu Glu Trp Ser His Val Asp Asn Pro Pro Val Leu
 65                  70                  75                  80

Glu Asp Phe Leu Gly His Gln Gly Leu Asn Thr Asp Ala Val Ile Asn
                     85                  90                  95

Asn Ile Glu Asp Ala Val Lys Leu Phe Ile Gly Asp Phe Phe Glu
            100                 105                 110

Phe Leu Val Glu Glu Ser Asn Arg Tyr Tyr Asn Gln Asn Arg Asn Asn
            115                 120                 125

Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
    195                 200                 205

Arg Leu Cys Lys Val Arg Pro Val Leu Asp Tyr Phe Val Pro Lys Phe
210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
            245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285

Leu Glu Thr Ile Gln Thr Trp Ser Pro Tyr Thr Asp Ser Trp Tyr His
    290                 295                 300

Ile Tyr Met Asp Asn Tyr Tyr Asn Ser Val Ala Asn Cys Glu Ala Leu
305                 310                 315                 320

Met Lys Asn Lys Phe Arg Ile Cys Gly Thr Ile Arg Lys Asn Arg Gly
            325                 330                 335

Ile Pro Lys Asp Phe Gln Thr Ile Ser Leu Lys Lys Gly Glu Thr Lys
            340                 345                 350

Phe Ile Arg Lys Asn Asp Ile Leu Leu Gln Val Trp Gln Ser Lys Lys
    355                 360                 365

Pro Val Tyr Leu Ile Ser Ser His Ser Ala Glu Met Glu Glu Ser Gln
    370                 375                 380

Asn Ile Asp Arg Thr Ser Lys Lys Ile Val Lys Pro Asn Ala Leu
385                 390                 395                 400

Ile Asp Tyr Asn Lys His Met Lys Gly Val Asp Arg Ala Asp Gln Tyr
                405                 410                 415

Leu Ser Tyr Tyr Ser Ile Leu Arg Arg Trp Lys Trp Thr Lys Arg Leu
            420                 425                 430

Ala Met Tyr Met Ile Asn Cys Ala Leu Phe Asn Ser Tyr Ala Val Tyr
        435                 440                 445

Lys Ser Val Arg Gln Arg Lys Met Gly Phe Lys Met Phe Leu Lys Gln
    450                 455                 460
```

```
Thr Ala His Trp Leu Thr Asp Asp Ile Pro Glu Asp Met Asp Ile Val
465                 470                 475                 480

Pro Asp Leu Gln Pro Val Pro Ser Thr Ser Gly Met Arg Ala Lys Pro
            485                 490                 495

Pro Thr Ser Asp Pro Pro Cys Arg Leu Ser Met Asp Met Arg Lys His
        500                 505                 510

Thr Leu Gln Ala Ile Val Gly Ser Gly Lys Lys Asn Ile Leu Arg
    515                 520                 525

Arg Cys Arg Val Cys Ser Val His Lys Leu Arg Ser Glu Thr Arg Tyr
    530                 535                 540

Met Cys Lys Phe Cys Asn Ile Pro Leu His Lys Gly Ala Cys Phe Glu
545                 550                 555                 560

Lys Tyr His Thr Leu Lys Asn
                565

<210> SEQ ID NO 112
<211> LENGTH: 13
<212> TYPE: DNA
<213> ORGANISM: Artificial sequence
<220> FEATURE:
<223> OTHER INFORMATION: Synthetic

<400> SEQUENCE: 112
ccctagaaag ata                                                              13

<210> SEQ ID NO 113
<211> LENGTH: 13
<212> TYPE: DNA
<213> ORGANISM: Artificial sequence
<220> FEATURE:
<223> OTHER INFORMATION: Synthetic

<400> SEQUENCE: 113
tatctttcta ggg                                                              13

<210> SEQ ID NO 114
<211> LENGTH: 296
<212> TYPE: DNA
<213> ORGANISM: Artificial sequence
<220> FEATURE:
<223> OTHER INFORMATION: Synthetic

<400> SEQUENCE: 114
gtctgcgtaa aattgacgca tgcattcttg aaatattgct ctctctttct aaatagcgcg          60
aatccgtcgc tgtgcattta ggacatctca gtcgccgctt ggagctcccg tgaggcgtgc         120
ttgtcaatgc ggtaagtgtc actgattttg aactataacg accgcgtgag tcaaaatgac         180
gcatgattat cttttacgtg acttttaaga tttaactcat acgataatta tattgttatt         240
tcatgttcta cttacgtgat aacttattat atatatattt tcttgttata gatatc            296

<210> SEQ ID NO 115
<211> LENGTH: 218
<212> TYPE: DNA
<213> ORGANISM: Artificial sequence
<220> FEATURE:
<223> OTHER INFORMATION: Synthetic

<400> SEQUENCE: 115
tttgttactt tatagaagaa attttgagtt tttgtttttt tttaataaat aaataaacat          60
aaataaattg tttgttgaat ttattattag tatgtaagtg taaatataat aaaacttaat         120
```

```
atctattcaa attaataaat aaacctcgat atacagaccg ataaaacaca tgcgtcaatt      180
ttacgcatga ttatctttaa cgtacgtcac aatatgat                              218
```

<210> SEQ ID NO 116
<211> LENGTH: 594
<212> TYPE: PRT
<213> ORGANISM: Artificial sequence
<220> FEATURE:
<223> OTHER INFORMATION: Synthetic

<400> SEQUENCE: 116

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350
```

```
Pro Leu Ala Lys Asn Leu Leu Gln Glu Pro Tyr Lys Leu Thr Ile Val
            355                 360                 365
Gly Thr Val Arg Ser Asn Lys Arg Glu Ile Pro Glu Val Leu Lys Asn
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
            405                 410                 415
Leu Ser Ser Cys Asp Glu Asp Ala Ser Ile Asn Glu Ser Thr Gly Lys
        420                 425                 430
Pro Gln Met Val Met Tyr Tyr Asn Gln Thr Lys Gly Gly Val Asp Thr
            435                 440                 445
Leu Asp Gln Met Cys Ser Val Met Thr Cys Ser Arg Lys Thr Asn Arg
        450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
            485                 490                 495
Gln Ser Arg Lys Lys Phe Met Arg Asn Leu Tyr Met Ser Leu Thr Ser
        500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Lys Glu Val Pro Gly Thr Ser
        530                 535                 540
Asp Asp Ser Thr Glu Glu Pro Val Met Lys Lys Arg Thr Tyr Cys Thr
545                 550                 555                 560
Tyr Cys Pro Ser Lys Ile Arg Arg Lys Ala Asn Ala Ser Cys Lys Lys
            565                 570                 575
Cys Lys Lys Val Ile Cys Arg Glu His Asn Ile Asp Met Cys Gln Ser
        580                 585                 590
Cys Phe

<210> SEQ ID NO 117
<211> LENGTH: 18
<212> TYPE: DNA
<213> ORGANISM: Artificial sequence
<220> FEATURE:
<223> OTHER INFORMATION: Synthetic

<400> SEQUENCE: 117
cccttgrcat gcctggta                                                     18

<210> SEQ ID NO 118
<211> LENGTH: 18
<212> TYPE: DNA
<213> ORGANISM: Artificial sequence
<220> FEATURE:
<223> OTHER INFORMATION: Synthetic

<400> SEQUENCE: 118
taccaggcat gycaaggg                                                     18

<210> SEQ ID NO 119
<211> LENGTH: 297
<212> TYPE: DNA
<213> ORGANISM: Artificial sequence
<220> FEATURE:
<223> OTHER INFORMATION: Synthetic
```

<400> SEQUENCE: 119

```
gggtttatta gacccaccac tttgaaaaac ctatgatatt tttttaaatt gaaggctatt    60
gttgacgtgt gttatagtag cttcgcgcaa taaaccggcg gccatttga cgagcgaact    120
tcagtctcac gtgagcgtgc gtgcgagtag cacgtgtgta aagtgcgcgc gggcccgtgg   180
gaccctacca ggcatacaac gtaacattct gtcggtaaga atattttctt tattttttgg   240
catttctttg tttaatgtgt taaattataa tacgaaaaaa atattgttgc agtagaa      297
```

<210> SEQ ID NO 120
<211> LENGTH: 337
<212> TYPE: DNA
<213> ORGANISM: Artificial sequence
<220> FEATURE:
<223> OTHER INFORMATION: Synthetic

<400> SEQUENCE: 120

```
atcttttcga ttatccaaag ataatagtat tttagttgat ttattagtgc cttaaattaa    60
tgaaagtctg acttcgatct ctgcattata tgtaagattg ttaattatag aactaagagt   120
ttaatttctg ttaattaaaa ttaagcgatt ttgaataatt gttaaataaa gatattttca   180
catacattta catattttat ttattatctg taataataat acattctaaa agacataaat   240
ataaaacaaa attttcctag cttgttcatt tgtgtaaaac atgtattttc aatatcgggt   300
ttgacagacc caccaggcat gccgtgtgat ttttatg                            337
```

<210> SEQ ID NO 121
<211> LENGTH: 588
<212> TYPE: PRT
<213> ORGANISM: Artificial sequence
<220> FEATURE:
<223> OTHER INFORMATION: Synthetic

<400> SEQUENCE: 121

Met Ala Arg Gly Leu Thr Asp Leu Glu Ile Asn Gln Ile Leu Glu Leu
1               5                   10                  15

Glu Asp Val Glu Asn Asp Val Ile Phe Asp Glu Ser Gly Asp Glu Ser
                20                  25                  30

Asp His Val Ser Ile Arg Val Glu Ser Asp Thr Glu Glu Val Glu Ile
            35                  40                  45

Pro Thr Leu Glu Pro Gln Gln Gly Ser Ser Asp Ser Glu Asn Asp Gln
        50                  55                  60

Pro Leu Ser Asn Leu Ala Arg Arg Ser Phe Tyr Lys Gly Lys Asp Asn
65                  70                  75                  80

Thr Ile Trp Asn Arg Ala Pro Asn Pro Arg Val Arg Thr Arg Ser
                85                  90                  95

Glu Asn Ile Val Thr Gly Thr Pro Gly Val Lys Arg Gln Ala Lys Asn
                100                 105                 110

Ala Leu Leu Glu Leu Asp Cys Phe His Leu Phe Val Asn Glu Ser Ile
            115                 120                 125

Leu Ser Val Ile Leu Glu His Thr Asn His Lys Ile Arg Ser Glu Arg
        130                 135                 140

Gln Gly Lys Asn Thr Ser Asn Glu Tyr Ala Tyr Ser Glu Thr Thr Leu
145                 150                 155                 160

Thr Glu Leu Arg Ala Val Ile Gly Leu Leu Tyr Leu Ala Gly Leu Phe
                165                 170                 175

Lys Ser Gly Arg Gln Asn Leu Gln Asp Leu Trp Ala Ser Asp Gly Thr

```
                180                 185                 190
Gly Ile Glu Ile Phe Pro Met Thr Met Ser Leu Arg Arg Phe Ala Phe
            195                 200                 205

Ile Val Asn Cys Leu Arg Phe Asp Asp Ser Asp Thr Arg Glu Glu Arg
        210                 215                 220

Ala Ala Ile Asp Arg Leu Ala Pro Ile Arg Gln Ile Tyr Glu Glu Phe
225                 230                 235                 240

Val Lys Asn Cys Lys Asp Val Tyr Thr Pro Tyr Glu Asn Leu Thr Ile
                245                 250                 255

Asp Glu Glu Leu Val Ala Phe Arg Gly Arg Cys Lys Phe Arg Gln Tyr
            260                 265                 270

Leu Pro Asn Lys Pro Ala Lys Tyr Gly Ile Lys Ile Ala Leu Val
        275                 280                 285

Asp Ala Tyr Thr Tyr Tyr Ser Leu Asn Met Glu Ile Tyr Ala Gly Asp
        290                 295                 300

Gln Pro Asp Gly Pro Tyr Lys Val Ser Asn Lys Pro His Asp Val Val
305                 310                 315                 320

Asp Arg Ile Val Gln Pro Ile Ser Gln Thr Gly Arg Asn Val Thr Met
                325                 330                 335

Asp Asn Trp Phe Thr Ser Tyr Pro Thr Tyr Ala His Leu Leu Lys Asn
            340                 345                 350

His Lys Leu Thr Ala Val Gly Thr Met Lys Ser Asn Lys Thr Cys Ile
        355                 360                 365

Pro Pro Lys Phe Arg Glu Arg Glu Ile Asn Thr Ser Leu Phe Gly
        370                 375                 380

Phe Gln Asp Asp Phe Thr Ile Val Ser Tyr Ile Pro Lys Arg Asn Lys
385                 390                 395                 400

Asn Val Phe Met Leu Ser Ser Leu His His Asp Ser Glu Ile Asp Ser
                405                 410                 415

Glu Thr Gly Glu Gln Gln Lys Pro Ser Ile Ile Thr Phe Tyr Asn Lys
            420                 425                 430

Thr Lys Ser Gly Val Asp Asn Val Asp Lys Leu Ile Arg Thr Tyr Asp
        435                 440                 445

Val Ser Arg Asn Ser Arg Arg Trp Pro Leu Thr Ile Phe Phe Trp Ile
    450                 455                 460

Leu Asn Thr Ala Gly Ile Asn Ala Lys Ile Val Gln Met Leu Asn Ser
465                 470                 475                 480

Ser Asp Asn Thr Pro Thr Arg Arg Ala Phe Ile Lys Lys Leu Gly Met
                485                 490                 495

Ser Leu Ile Ala Pro His Gln Ala Glu Arg Lys Thr Asn Ser Lys Ile
            500                 505                 510

Pro Val Ser Leu Arg Lys Arg Ile Gly Ser His Leu Gly Glu Ser Ser
        515                 520                 525

Ala Ser Pro Ala Lys Ile Pro Asn Val Gly Val Lys Lys Arg Cys Tyr
        530                 535                 540

Ile Cys Pro Val Lys Lys Asp Arg Lys Ser Lys Tyr Ile Cys Ile Ser
545                 550                 555                 560

Cys Thr Ser His Ile Cys Leu Glu His Ala Asn Phe Val Cys Glu Asn
                565                 570                 575

Cys Arg Arg Asn Glu Glu Glu Asn Ser Asp Ser Ser
            580                 585

<210> SEQ ID NO 122
```

```
<211> LENGTH: 19
<212> TYPE: DNA
<213> ORGANISM: Artificial sequence
<220> FEATURE:
<223> OTHER INFORMATION: Synthetic

<400> SEQUENCE: 122
cctttarctr ctgaggtgg                                                  19

<210> SEQ ID NO 123
<211> LENGTH: 19
<212> TYPE: DNA
<213> ORGANISM: Artificial sequence
<220> FEATURE:
<223> OTHER INFORMATION: Synthetic

<400> SEQUENCE: 123
ccacctcagy agytaaagg                                                  19

<210> SEQ ID NO 124
<211> LENGTH: 273
<212> TYPE: DNA
<213> ORGANISM: Artificial sequence
<220> FEATURE:
<223> OTHER INFORMATION: Synthetic

<400> SEQUENCE: 124
gggcttttcg agcctagcga aagtgaaatt gttcccctcc tcccttcccc cgcgcgcgac     60
aaacccgtaa cttctagtag cttcgatgtt agttgcgcct aggccgtcag aagcttcgca    120
cgtgttttcg tgcgcaattc ggtaagtaaa ttcaatttga aatttgtcgc gggcttctta    180
ggccccacct cagtgtttac gtaacttttt tgtaaatagt ttcgattaag ttattgtgtt    240 tttttttgc agtagcttga aaacgtttga aaa                                  273

<210> SEQ ID NO 125
<211> LENGTH: 370
<212> TYPE: DNA
<213> ORGANISM: Artificial sequence
<220> FEATURE:
<223> OTHER INFORMATION: Synthetic

<400> SEQUENCE: 125
ttttggtgct tgtattttt ttcttcccat aatacaaaga taattatgaa tgtgcctaat      60 gctaaaaga ctgttaaaaa ttaatatttt atgtaagttt gttgattatt tctaatattt    120
taatgaatac tttgtgattt ttgatctcat gtgattttgc caaaaatttt gctaagtgtt    180
ttttaaaaac actcaaaagt taattataaa taaaaaaatt aaacaaaaaa catttttattt   240 tatttaaaat ctatccacaa aagcttatta ttatacaata aaacctaaaa acccccaaata  300 ttttaaaata tgaacattta tatacacggg ccgcggaggc ccccacgtca gtacttacgt   360
gaaaataatt                                                          370

<210> SEQ ID NO 126
<211> LENGTH: 613
<212> TYPE: PRT
<213> ORGANISM: Artificial sequence
<220> FEATURE:
<223> OTHER INFORMATION: Synthetic

<400> SEQUENCE: 126

Met Glu Pro Ser Thr Ser Ser Gly Arg Lys Arg Ser Ile Gly Asn Val
1               5                   10                  15
```

-continued

His Asn Gln Arg Ala Ala Lys Asn Arg Arg Ala Val Val Pro Gly Thr
                20                  25                  30

Arg Asp Phe Gly Thr Thr Leu Thr Ser Trp Leu Asp Asn Glu Asp Ser
             35                  40                  45

Ser Gly Ser Glu Val Glu Asp Ile Gly Asp Asn Phe Thr Pro Glu Arg
         50                  55                  60

His Glu Ile Glu Ser Asp Thr Ile Ser Gln Ser Glu Ser Glu Glu Gln
 65                  70                  75                  80

Val Ala Asp His Val Thr Glu Glu His Asn Met Ser Ser Asp Asp Asp
                 85                  90                  95

Ala Pro Leu Ser Thr Arg Arg Ser Phe Tyr Gly Lys Asn Arg Tyr Lys
            100                 105                 110

Trp Ala Cys Gln Pro Leu Ser Arg Ala Val Arg Val Pro Gln His Asn
        115                 120                 125

Ile Ile Gln Arg Thr Asn Val Ser Asn Leu Thr Glu Asp Asp Pro Lys
    130                 135                 140

Asp Pro Phe Ser Ile Trp Asn Lys Leu Met Asp Asp Glu Ile Leu Gln
145                 150                 155                 160

Glu Thr Leu Lys Trp Thr Asn Glu Lys Ile Ile Gln Tyr Arg Ser Lys
                165                 170                 175

Phe Ser Asp Lys Asp Arg Pro Glu Leu Arg Asn Leu Asp Met Val Glu
            180                 185                 190

Leu His Ala Phe Ile Gly Leu Leu Leu Phe Thr Ala Val Phe Lys Ser
        195                 200                 205

Asn His Glu Asn Val Asn Tyr Leu Phe Ala Thr Asp Gly Thr Gly Arg
    210                 215                 220

Glu Ile Phe Arg Cys Val Met Ser Lys Asn Arg Phe Leu Val Ile Leu
225                 230                 235                 240

His Cys Leu Arg Phe Asp Asn Pro Asp Asp Arg Glu Glu Arg Arg Glu
                245                 250                 255

Ser Asp Lys Ile Ala Ala Ile Ser Tyr Ile Phe Thr Lys Phe Val Gly
            260                 265                 270

Asn Cys Gln Lys Ile Tyr Asn Val Cys Glu Tyr Ala Thr Val Asp Glu
        275                 280                 285

Met Leu Val Pro Phe Arg Gly Arg Thr His Leu Met Ile Tyr Met Pro
    290                 295                 300

Met Lys Pro Ala Lys Tyr Gly Leu Lys Leu Met Cys Leu Cys Asp Ala
305                 310                 315                 320

Asn Asn Gly Tyr Phe Tyr Asn Cys Tyr Ile Tyr Thr Gly Arg Gly Ser
                325                 330                 335

Asp Gly Ala Gly Leu Thr Glu Glu Lys Lys Phe Met Val Pro Thr
            340                 345                 350

Gln Ser Val Ile His Leu Ala Lys Pro Leu Phe Gly Ser Asn Arg Asn
        355                 360                 365

Ile Thr Cys Asp Asn Trp Phe Thr Ser Ile Glu Leu Ile Glu Tyr Leu
    370                 375                 380

Lys Lys Lys Gly Leu Thr Cys Val Gly Thr Met Lys Lys Asn Lys Arg
385                 390                 395                 400

Glu Ile Pro Lys Glu Phe Leu Pro Ser Lys Gln Arg Asp Val Gly Ser
                405                 410                 415

Ser Leu Tyr Gly Tyr Ala Gly Gln Asn Thr Ile Leu Ser His Val Pro
            420                 425                 430

Lys Lys Asn Lys Ala Val Ile Leu Leu Ser Ser Met His His Ala Glu

```
              435                 440                 445
Ala Val Asp Glu Thr Thr Gly Lys Pro Glu Ile Ile Gly Phe Tyr Asn
    450                 455                 460

Lys Thr Lys Gly Gly Val Asp Glu Ile Asp Lys Lys Cys Ala Ile Tyr
465                 470                 475                 480

Thr Ser Ser Arg Arg Thr Arg Arg Trp Pro Met Val Val Phe Tyr Arg
                485                 490                 495

Met Leu Asp Ile Ser Thr Val Asn Ser His Leu Ile Tyr Asp Ile His
                500                 505                 510

His Asp Lys Thr Thr Glu Arg Gly Met Phe Leu Lys Gln Leu Ala Arg
            515                 520                 525

Thr Leu Val Leu Pro Gln Met Lys Arg Arg Ala Leu Asn Glu Arg Leu
530                 535                 540

Pro Arg Glu Leu Arg Leu Ser Leu Ala Arg Val Leu Gly Pro Asp Met
545                 550                 555                 560

Pro Val Pro Asp Pro Gln Glu Val Asp Glu Thr Phe Lys Thr Arg Arg
                565                 570                 575

Arg Cys His Thr Cys Pro Leu Lys Leu Gln Arg Lys Ser Thr His Thr
                580                 585                 590

Cys Tyr Thr Cys Lys Lys His Val Cys Leu Gln Cys Ala Lys Gln Val
                595                 600                 605

Cys Ala Asp Cys Val
    610

<210> SEQ ID NO 127
<211> LENGTH: 15
<212> TYPE: DNA
<213> ORGANISM: Artificial sequence
<220> FEATURE:
<223> OTHER INFORMATION: Synthetic

<400> SEQUENCE: 127
ccctcrtatt atgtt                                                          15

<210> SEQ ID NO 128
<211> LENGTH: 15
<212> TYPE: DNA
<213> ORGANISM: Artificial sequence
<220> FEATURE:
<223> OTHER INFORMATION: Synthetic

<400> SEQUENCE: 128
aacataatay gaggg                                                          15

<210> SEQ ID NO 129
<211> LENGTH: 401
<212> TYPE: DNA
<213> ORGANISM: Artificial sequence
<220> FEATURE:
<223> OTHER INFORMATION: Synthetic

<400> SEQUENCE: 129
aagggtcaat ttgacccatt tcagtttttg gtttgaccaa agaactggtt atcctttctt         60
tttcttcacg aaagttggtg acttttcctc atctagggtc atgaacttgt gtgtaaaatc        120
tggatactgt gaagtgtcgt ggaatgtctg tgaacagttt gtatacaaag atgatgttgc        180
gggtcatttt gacccacaca ctttgatgtg agcaagtagc tgtccagatc cgaaataaac        240
atgtctcttt gatgcacttt attttgattg ctaaattatt tatattttga ctgtctctga        300
```

```
atagaccttc agatcagaga cccaggtgtg tgtgggggag gagctttctc tcccttgtcc    360
ttgtcactgt tctcgtgtca tctctttgag aaacagcaaa a                       401
```

<210> SEQ ID NO 130
<211> LENGTH: 247
<212> TYPE: DNA
<213> ORGANISM: Artificial sequence
<220> FEATURE:
<223> OTHER INFORMATION: Synthetic

<400> SEQUENCE: 130

```
agatactgaa tattgaaaat ctcagaaaat gtgacaagtt aaattacaaa aaaaaagtgt    60
ttgtgaagga aaaaatatt aaatatagtg ttggaataaa aaaatagtat tgtttgtctc    120
tttcctaaat gttgaaatat tctaaaataa agttgatatc agtttaacct gttttttat    180 tgttttgagt ggatttacac agtatgggtc aaaatgaccc gcaacataat caaggtaatt   240
tttttc                                                              247
```

<210> SEQ ID NO 131
<211> LENGTH: 579
<212> TYPE: PRT
<213> ORGANISM: Artificial sequence
<220> FEATURE:
<223> OTHER INFORMATION: Synthetic

<400> SEQUENCE: 131

```
Met Ser Ser Arg Arg Phe Thr Ala Glu Glu Ala Leu Leu Leu Phe Phe
1               5                   10                  15

Asp Ser Asp Ala Glu Glu Glu Ile Ser Glu Ile Glu Asp Leu Ser Asp
            20                  25                  30

Ala Glu Asp Asn Asp Ile Asp Asp Pro Asp Phe Gln Phe Ser Asp Asp
        35                  40                  45

Glu Glu Asp Ser Glu Asp Glu Ser Ala Val Val Ser Pro Ser Asp Glu
    50                  55                  60

Asn Leu Gly Met Glu Gln Ser Ser Ser Thr Glu Gly Thr Trp Ala Ser
65                  70                  75                  80

Lys Asp Gly Asn Ile Lys Trp Ser Thr Ser Pro His Gln Ser Arg Gly
                85                  90                  95

Arg Leu Ser Ser Ser Asn Ile Ile Lys Met Thr Pro Gly Pro Thr Arg
            100                 105                 110

Phe Ala Val Thr Arg Val Asp Asp Ile Gln Ser Ala Phe Gln Leu Phe
        115                 120                 125

Ile Ser Gln Pro Ile Glu Arg Ile Leu Asp Met Thr Asn Leu Glu
    130                 135                 140

Gly Arg Arg Val Phe Gln Glu Lys Trp Lys Ser Leu Asp Gln Thr Asp
145                 150                 155                 160

Leu Asn Ala Tyr Ile Gly Ile Leu Ile Leu Ala Gly Val Tyr Arg Ser
                165                 170                 175

Lys Gly Glu Ala Thr Ser Ser Leu Trp Asn Glu Glu Asn Gly Arg Pro
            180                 185                 190

Ile Phe Arg Ala Thr Met Ser Leu Glu Thr Phe His Met Ile Ser Arg
        195                 200                 205

Val Ile Arg Phe Asp Asn Arg Asp Thr Arg Val Gly Arg Arg Glu Ser
    210                 215                 220

Asp Lys Leu Ala Ala Ile Arg Asp Val Trp Asp Lys Trp Val Glu Ile
225                 230                 235                 240
```

```
Leu Pro Leu Leu Tyr Asn Pro Gly Pro His Val Thr Val Asp Glu Arg
            245                 250                 255
Leu Val Pro Phe Arg Gly Arg Cys Pro Phe Arg Gln Tyr Met Pro Asn
        260                 265                 270
Lys Pro Ala Lys Tyr Gly Ile Lys Ile Trp Ala Ala Cys Asp Ala Lys
    275                 280                 285
Ser Ser Tyr Ala Trp Lys Met Gln Val Tyr Thr Gly Lys Ser Pro Gly
290                 295                 300
Gly Ala Pro Glu Lys Asn Gln Gly Met Arg Val Leu Glu Met Ser
305                 310                 315                 320
Glu Gly Leu Gln Gly His Asn Ile Thr Cys Asp Asn Phe Phe Thr Ser
                325                 330                 335
Tyr Arg Leu Gly Glu Glu Leu Gln Lys Arg Lys Leu Thr Met Leu Gly
            340                 345                 350
Thr Val Arg Arg Asn Lys Pro Glu Leu Pro Ser Glu Ile Leu Lys Ile
        355                 360                 365
Gln Gly Arg Pro Met His Ser Ser Ile Phe Ala Phe Thr Glu Lys Ala
    370                 375                 380
Thr Val Val Ser Tyr Cys Pro Lys Arg Asn Lys Asn Val Leu Val Met
385                 390                 395                 400
Ser Thr Met His Thr Asp Ala Ser Leu Ser Thr Arg Asp Asp Met Lys
                405                 410                 415
Pro Gln Met Ile Leu Asp Tyr Asn Ser Thr Lys Gly Val Asp Asn
            420                 425                 430
Leu Asp Lys Val Thr Ala Thr Tyr Ser Cys Gln Arg Lys Thr Ala Arg
        435                 440                 445
Trp Pro Met Ala Ile Phe Phe Asn Ile Val Asp Val Ser Ala Tyr Asn
    450                 455                 460
Ala Tyr Val Leu Trp Ser Glu Ile Asn Gln Glu Trp Asn Ala Gly Lys
465                 470                 475                 480
Leu Tyr Arg Arg Arg Leu Phe Leu Glu Glu Leu Gly Lys Ala Leu Ile
                485                 490                 495
Thr Pro Lys Ile Gln Arg Arg Ala Arg Pro Ala Arg Ser Pro Ala Ala
            500                 505                 510
Ala Ala Val Ile Glu Lys Ile Lys Phe Arg Thr Ser Asn Gln Phe Ala
        515                 520                 525
Met Asp Pro Val Asp Thr Asp Val Lys Lys Arg Lys Arg Cys Gln Val
    530                 535                 540
Cys Pro Ser Arg Asp Asp Ser Leu Thr Ser Thr Ser Cys Val Lys Cys
545                 550                 555                 560
Lys Asn Phe Ile Cys Arg Lys His Thr Val Thr Phe Cys Pro Ser Cys
                565                 570                 575
Gly Glu His

<210> SEQ ID NO 132
<211> LENGTH: 16
<212> TYPE: DNA
<213> ORGANISM: Artificial sequence
<220> FEATURE:
<223> OTHER INFORMATION: Synthetic

<400> SEQUENCE: 132
ccctagaagc ccaatc                                                    16

<210> SEQ ID NO 133
```

```
<211> LENGTH: 16
<212> TYPE: DNA
<213> ORGANISM: Artificial sequence
<220> FEATURE:
<223> OTHER INFORMATION: Synthetic

<400> SEQUENCE: 133
gattgggctt ctaggg                                                         16

<210> SEQ ID NO 134
<211> LENGTH: 303
<212> TYPE: DNA
<213> ORGANISM: Artificial sequence
<220> FEATURE:
<223> OTHER INFORMATION: Synthetic

<400> SEQUENCE: 134
tacgtaaatt tgacgtatac cgcggcgaaa tatatctgtc tctttcacgt ttaccgtcgg          60
attcccgcta acttcggaac caactcagta gccattgaga actcccagga cacagttgcg        120
tcatctcggt aagtgccgcc attttgttgt aatagacagg ttgcacgtca ttttgacgta        180
taattgggct tgtgtaact tttgaaatta tttataattt ttattgatgt gatttatttg         240
agttaatcgt attgtttcgt tacatttttc atatgatatt aatattttca gattgaatat        300
aaa                                                                      303

<210> SEQ ID NO 135
<211> LENGTH: 347
<212> TYPE: DNA
<213> ORGANISM: Artificial sequence
<220> FEATURE:
<223> OTHER INFORMATION: Synthetic

<400> SEQUENCE: 135
agactgtttt ttttaaaagg cttataaagt attactattg cgtgatttaa ttttataaaa         60
atatttaaaa ccagttgatt tttttaataa ttacctaatt ttaagaaaaa atgttagaag        120
cttgatattt ttgttgattt ttttctaaga tttgattaaa aggccataat tgtattaata        180
aagagtattt ttaacttcaa atttatttta tttattaatt aaaacttcaa ttatgataat        240
acatgcaaaa atatagttca tcaacagaaa aatataggaa aactctaata gtttttatttt       300 tacacgtcat ttttacgtat gattgggctt tatagctagt caaatat                      347

<210> SEQ ID NO 136
<211> LENGTH: 598
<212> TYPE: PRT
<213> ORGANISM: Artificial sequence
<220> FEATURE:
<223> OTHER INFORMATION: Synthetic

<400> SEQUENCE: 136

Met Glu Ser Arg Gln Arg Leu Asn Gln Asp Glu Ile Ala Thr Ile Leu
1               5                   10                  15

Glu Asn Asp Asp Asp Tyr Ser Pro Leu Asp Ser Asp Ser Glu Ala Glu
                20                  25                  30

Asp Arg Val Val Glu Asp Val Trp Ser Asp Asn Glu Asp Ala Met
        35                  40                  45

Ile Asp Tyr Val Glu Asp Thr Ser Arg Gln Glu Asp Pro Asp Asn Asn
    50                  55                  60

Ile Ala Ser Gln Glu Ser Ala Asn Leu Glu Val Thr Ser Leu Thr Ser
65                  70                  75                  80
```

```
His Arg Ile Ile Ser Leu Pro Gln Arg Ser Ile Cys Gly Lys Asn Asn
                85                  90                  95
His Val Trp Ser Thr Thr Lys Gly Arg Thr Thr Gly Arg Thr Ser Ala
            100                 105                 110
Ile Asn Ile Ile Arg Thr Asn Arg Gly Pro Thr Arg Met Cys Arg Asn
            115                 120                 125
Ile Val Asp Pro Leu Leu Cys Phe Gln Leu Phe Ile Thr Asp Glu Ile
            130                 135                 140
Ile His Glu Ile Val Lys Trp Thr Asn Val Glu Met Ile Val Lys Arg
145                 150                 155                 160
Gln Asn Leu Ile Asp Ile Ser Ala Ser Tyr Arg Asp Thr Asn Thr Met
                165                 170                 175
Glu Met Trp Ala Leu Val Gly Ile Leu Thr Leu Thr Ala Val Met Lys
            180                 185                 190
Asp Asn His Leu Ser Thr Asp Glu Leu Phe Asp Ala Thr Phe Ser Gly
            195                 200                 205
Thr Arg Tyr Val Ser Val Met Ser Arg Glu Arg Phe Glu Phe Leu Ile
            210                 215                 220
Arg Cys Met Arg Met Asp Asp Lys Thr Leu Arg Pro Thr Leu Arg Ser
225                 230                 235                 240
Asp Asp Ala Phe Ile Pro Val Arg Lys Leu Trp Glu Ile Phe Ile Asn
                245                 250                 255
Gln Cys Arg Leu Asn Tyr Val Pro Gly Gly Asn Leu Thr Val Asp Glu
                260                 265                 270
Gln Leu Leu Gly Phe Arg Gly Arg Cys Pro Phe Arg Met Tyr Ile Pro
            275                 280                 285
Asn Lys Pro Asp Lys Tyr Gly Ile Arg Phe Pro Met Met Cys Asp Ala
            290                 295                 300
Ala Thr Lys Tyr Met Ile Asp Ala Ile Pro Tyr Leu Gly Lys Ser Thr
305                 310                 315                 320
Lys Thr Asn Gly Leu Pro Leu Gly Glu Phe Tyr Val Lys Glu Leu Thr
                325                 330                 335
Lys Thr Val His Gly Thr Asn Arg Asn Val Thr Cys Asp Asn Trp Phe
            340                 345                 350
Thr Ser Ile Pro Leu Ala Lys Asn Met Leu Gln Ala Pro Tyr Asn Leu
            355                 360                 365
Thr Ile Val Gly Thr Ile Arg Ser Asn Lys Arg Glu Ile Pro Glu Glu
            370                 375                 380
Ile Lys Asn Ser Arg Ser Arg Pro Val Gly Ser Ser Met Phe Cys Phe
385                 390                 395                 400
Asp Gly Pro Leu Thr Leu Val Ser Tyr Lys Pro Lys Pro Ser Arg Met
                405                 410                 415
Val Phe Leu Leu Ser Ser Cys Asp Glu Asn Ala Val Ile Asn Glu Ser
            420                 425                 430
Asn Gly Lys Pro Asp Met Ile Leu Phe Tyr Asn Gln Thr Lys Gly Gly
            435                 440                 445
Val Asp Ser Phe Asp Gln Met Cys Lys Ser Met Ser Ala Asn Arg Lys
            450                 455                 460
Thr Asn Arg Trp Pro Met Ala Val Phe Tyr Gly Met Leu Asn Met Ala
465                 470                 475                 480
Phe Val Asn Ser Tyr Ile Ile Tyr Cys His Asn Lys Ile Asn Lys Gln
                485                 490                 495
Lys Lys Pro Ile Asn Arg Lys Glu Phe Met Lys Asn Leu Ser Thr Asp
```

```
                500             505             510
Leu Thr Thr Pro Trp Met Gln Glu Arg Leu Lys Ala Pro Thr Leu Lys
        515                 520                 525

Arg Thr Leu Arg Asp Asn Ile Thr Asn Val Leu Lys Asn Val Val Pro
        530                 535                 540

Pro Ser Pro Ala Asn Asn Ser Glu Glu Pro Gly Pro Lys Lys Arg Ser
545                 550                 555                 560

Tyr Cys Gly Phe Cys Ser Tyr Lys Lys Arg Arg Met Thr Lys Thr Gln
                565                 570                 575

Phe Tyr Lys Cys Lys Lys Ala Ile Cys Gly Glu His Asn Ile Asp Val
                580                 585                 590

Cys Gln Asp Cys Val Gly
        595
```

<210> SEQ ID NO 137
<211> LENGTH: 16
<212> TYPE: DNA
<213> ORGANISM: Artificial sequence
<220> FEATURE:
<223> OTHER INFORMATION: Synthetic

<400> SEQUENCE: 137
ccctagaagc ccaatc                                                       16

<210> SEQ ID NO 138
<211> LENGTH: 16
<212> TYPE: DNA
<213> ORGANISM: Artificial sequence
<220> FEATURE:
<223> OTHER INFORMATION: Synthetic

<400> SEQUENCE: 138
gattgggctt ctaggg                                                       16

<210> SEQ ID NO 139
<211> LENGTH: 304
<212> TYPE: DNA
<213> ORGANISM: Artificial sequence
<220> FEATURE:
<223> OTHER INFORMATION: Synthetic

<400> SEQUENCE: 139
tacgtaaatt tgacgtatac cgcggcgaaa tatctctgtt actttcacgt ttaacgtcgg       60
atcgccgcta acttctgaac caactcagta gccattggga cctcgcagga cacagttgca      120
tcatctcggt aagtgccgcc attttgttgt aatagagagg ttgcacgtca ttttgacgta      180
taattgggct tgtgtaact tttgaaattg tttaaatttt tttaaatttg tgatttattt       240
gagttaatcg tattgtttcg ttacatttta catgtaatat taatatttc aggttgaata       300 caaa                                                                   304

<210> SEQ ID NO 140
<211> LENGTH: 370
<212> TYPE: DNA
<213> ORGANISM: Artificial sequence
<220> FEATURE:
<223> OTHER INFORMATION: Synthetic

<400> SEQUENCE: 140
tgtttgtcaa gactgtatat aaagactgtt ttttctaag aaacttataa aatattatta       60
caagttgatt taattttatg aaaaaattta aaactagttg atttttttta taattacata     120

```
attttaagaa aaagtgttag aggcttgatt tttttgtttt ttttttttcta aggtttgatt      180 gaaatgccat aatagtatta ataaagagta ttttttaact taaaatctat tttatttatt      240
aattaaaact tcaattatga taactcatgc aaaaatatag ttcattaaca gaaaaatctt      300
ggaaaactct gaagttttat ttttacacgt cattttttacg tatgattggg ctttataact    360
agttaaatat                                                              370
```

<210> SEQ ID NO 141
<211> LENGTH: 598
<212> TYPE: PRT
<213> ORGANISM: Artificial sequence
<220> FEATURE:
<223> OTHER INFORMATION: Synthetic

<400> SEQUENCE: 141

Met Ala Ser Arg Gln Arg Leu Asn His Asp Glu Ile Ala Thr Ile Leu
1               5                   10                  15

Glu Asn Asp Asp Asp Tyr Ser Pro Leu Asp Ser Glu Ser Glu Lys Glu
            20                  25                  30

Asp Cys Val Val Glu Asp Val Trp Ser Asp Asn Glu Asp Ala Ile
        35                  40                  45

Val Asp Phe Val Glu Asp Thr Ser Ala Gln Glu Asp Pro Asp Asn Asn
    50                  55                  60

Ile Ala Ser Arg Glu Ser Pro Asn Leu Glu Val Thr Ser Leu Thr Ser
65                  70                  75                  80

His Arg Ile Ile Thr Leu Pro Gln Arg Ser Ile Arg Gly Lys Asn Asn
                85                  90                  95

His Val Trp Ser Thr Thr Lys Gly Arg Thr Gly Arg Thr Ser Ala
            100                 105                 110

Ile Asn Ile Ile Arg Thr Asn Arg Gly Pro Thr Arg Met Cys Arg Asn
        115                 120                 125

Ile Val Asp Pro Leu Leu Cys Phe Gln Leu Phe Ile Thr Asp Glu Ile
    130                 135                 140

Ile His Glu Ile Val Lys Trp Thr Asn Val Glu Ile Ile Val Lys Arg
145                 150                 155                 160

Gln Asn Leu Lys Asp Ile Ser Ala Ser Tyr Arg Asp Thr Asn Thr Met
                165                 170                 175

Glu Ile Trp Ala Leu Val Gly Ile Leu Thr Leu Thr Ala Val Met Lys
            180                 185                 190

Asp Asn His Leu Ser Thr Asp Glu Leu Phe Asp Ala Thr Phe Ser Gly
        195                 200                 205

Thr Arg Tyr Val Ser Val Met Ser Arg Glu Arg Phe Glu Phe Leu Ile
    210                 215                 220

Arg Cys Ile Arg Met Asp Asp Lys Thr Leu Arg Pro Thr Leu Arg Ser
225                 230                 235                 240

Asp Asp Ala Phe Leu Pro Val Arg Lys Ile Trp Glu Ile Phe Ile Asn
                245                 250                 255

Gln Cys Arg Gln Asn His Val Pro Gly Ser Asn Leu Thr Val Asp Glu
            260                 265                 270

Gln Leu Leu Gly Phe Arg Gly Arg Cys Pro Phe Arg Met Tyr Ile Pro
        275                 280                 285

Asn Lys Pro Asp Lys Tyr Gly Ile Lys Phe Pro Met Met Cys Ala Ala
    290                 295                 300

Ala Thr Lys Tyr Met Ile Asp Ala Ile Pro Tyr Leu Gly Lys Ser Thr

```
            305                 310                 315                 320
Lys Thr Asn Gly Leu Pro Leu Gly Glu Phe Tyr Val Lys Asp Leu Thr
                325                 330                 335
Lys Thr Val His Gly Thr Asn Arg Asn Ile Thr Cys Asp Asn Trp Phe
                340                 345                 350
Thr Ser Ile Pro Leu Ala Lys Asn Met Leu Gln Ala Pro Tyr Asn Leu
                355                 360                 365
Thr Ile Val Gly Thr Ile Arg Ser Asn Lys Arg Glu Met Pro Glu Glu
                370                 375                 380
Ile Lys Asn Ser Arg Ser Arg Pro Val Gly Ser Ser Met Phe Cys Phe
385                 390                 395                 400
Asp Gly Pro Leu Thr Leu Val Ser Tyr Lys Pro Lys Pro Ser Lys Met
                405                 410                 415
Val Phe Leu Leu Ser Ser Cys Asp Glu Asn Ala Val Ile Asn Glu Ser
                420                 425                 430
Asn Gly Lys Pro Asp Met Ile Leu Phe Tyr Asn Gln Thr Lys Gly Gly
                435                 440                 445
Val Asp Ser Phe Asp Gln Met Cys Lys Ser Met Ser Ala Asn Arg Lys
                450                 455                 460
Thr Asn Arg Trp Pro Met Ala Val Phe Tyr Gly Met Leu Asn Met Ala
465                 470                 475                 480
Phe Val Asn Ser Tyr Ile Ile Tyr Cys His Asn Lys Ile Asn Lys Gln
                485                 490                 495
Glu Lys Pro Ile Ser Arg Lys Glu Phe Met Lys Lys Leu Ser Ile Gln
                500                 505                 510
Leu Thr Thr Pro Trp Met Gln Glu Arg Leu Gln Ala Pro Thr Leu Lys
                515                 520                 525
Arg Thr Leu Arg Asp Asn Ile Thr Asn Val Leu Lys Asn Val Val Pro
                530                 535                 540
Ala Ser Ser Glu Asn Ile Ser Asn Glu Pro Glu Pro Lys Lys Arg Arg
545                 550                 555                 560
Tyr Cys Gly Val Cys Ser Tyr Lys Lys Arg Arg Met Thr Lys Ala Gln
                565                 570                 575
Cys Cys Lys Cys Lys Lys Ala Ile Cys Gly Glu His Asn Ile Asp Val
                580                 585                 590
Cys Gln Asp Cys Ile Gly
        595

<210> SEQ ID NO 142
<211> LENGTH: 32
<212> TYPE: DNA
<213> ORGANISM: Artificial sequence
<220> FEATURE:
<223> OTHER INFORMATION: Synthetic

<400> SEQUENCE: 142
cagttgaagt cggaagttta catacactta ag                                  32

<210> SEQ ID NO 143
<211> LENGTH: 32
<212> TYPE: DNA
<213> ORGANISM: Artificial sequence
<220> FEATURE:
<223> OTHER INFORMATION: Synthetic

<400> SEQUENCE: 143
ctaaggtgta tgtaaacttc cgacttcaac tg                                  32
```

<210> SEQ ID NO 144
<211> LENGTH: 227
<212> TYPE: DNA
<213> ORGANISM: Artificial sequence
<220> FEATURE:
<223> OTHER INFORMATION: Synthetic

<400> SEQUENCE: 144

```
cagttgaagt cggaagttta catacactta agttggagtc attaaaactc gttttcaac      60
tacaccacaa atttcttgtt aacaaacaat agttttggca agtcagttag acatctact     120
ttgtgcatga cacaagtcat ttttccaaca attgtttaca gacagattat ttcacttata    180
attcactgta tcacaattcc agtgggtcag aagtttacat acactaa                  227
```

<210> SEQ ID NO 145
<211> LENGTH: 229
<212> TYPE: DNA
<213> ORGANISM: Artificial sequence
<220> FEATURE:
<223> OTHER INFORMATION: Synthetic

<400> SEQUENCE: 145

```
ttgagtgtat gttaacttct gacccactgg gaatgtgatg aaagaaataa aagctgaaat     60
gaatcattct ctctactatt attctgatat ttcacattct taaataaag tggtgatcct    120
aactgacctt aagacaggga atctttactc ggattaaatg tcaggaattg tgaaaaagtg   180
agtttaaatg tatttggcta aggtgtatgt aaacttccga cttcaactg                229
```

<210> SEQ ID NO 146
<211> LENGTH: 340
<212> TYPE: PRT
<213> ORGANISM: Artificial sequence
<220> FEATURE:
<223> OTHER INFORMATION: Synthetic

<400> SEQUENCE: 146

```
Met Gly Lys Ser Lys Glu Ile Ser Gln Asp Leu Arg Lys Arg Ile Val
1               5                  10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175
```

```
Lys Pro Lys Asn Thr Ile Pro Thr Val Lys His Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Gln Phe Lys Gly Asn
                325                 330                 335

Ala Thr Lys Tyr
            340

<210> SEQ ID NO 147
<211> LENGTH: 16
<212> TYPE: DNA
<213> ORGANISM: Artificial sequence
<220> FEATURE:
<223> OTHER INFORMATION: Synthetic

<400> SEQUENCE: 147
cagtgttctt caacct                                                   16

<210> SEQ ID NO 148
<211> LENGTH: 16
<212> TYPE: DNA
<213> ORGANISM: Artificial sequence
<220> FEATURE:
<223> OTHER INFORMATION: Synthetic

<400> SEQUENCE: 148
aggttgaaga acactg                                                   16

<210> SEQ ID NO 149
<211> LENGTH: 328
<212> TYPE: DNA
<213> ORGANISM: Artificial sequence
<220> FEATURE:
<223> OTHER INFORMATION: Synthetic

<400> SEQUENCE: 149
cagtgttctt caacctgtgt tccgcggaac cctagggttc cacccaaagg ctttcggggt    60
tccgcgagtc attgcttcaa ttcgagagac gtcggccgcg ccgctcttca gaatgcacat   120
gcgtcaatcg gagtttcatg ttgaaacatg ttatccattc gcatagttga cttacactgc   180
acttaacctt aattttcaaa aatatgtaac tgtacttgtg gtcgtagttt tgttgttgtt   240
ttaggtttag acaagcaaag gtaagttaac ttacagtttt aaaataaatt gtattttgtt   300
tgatcctaac ctagaatcgt tcagaaat                                     328
```

<210> SEQ ID NO 150
<211> LENGTH: 145
<212> TYPE: DNA
<213> ORGANISM: Artificial sequence
<220> FEATURE:
<223> OTHER INFORMATION: Synthetic

<400> SEQUENCE: 150

```
ccaaagcacg ggctcacctt gttcgtaaca agtcaacgca gctgtcccta aaatctcatc      60
tgggtgtatt actaaatgaa gggttccata aaaaaaaata tctcgacaaa gggttccgcc     120
ggatggcaaa ggttgaagaa cactg                                           145
```

<210> SEQ ID NO 151
<211> LENGTH: 636
<212> TYPE: PRT
<213> ORGANISM: Artificial sequence
<220> FEATURE:
<223> OTHER INFORMATION: Synthetic

<400> SEQUENCE: 151

```
Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Asp Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
```

```
                    275                 280                 285
        Asp Gly Ala Lys Ala Met Val Gly Val Ile Lys Gly Val Ile Ala Arg
            290                 295                 300

Ile Lys Lys Leu Val Pro Asp Ile Lys Ala Ser His Cys Cys Leu His
        305                 310                 315                 320

Arg His Ala Leu Ala Val Lys Arg Ile Pro Asn Ala Leu His Glu Val
                        325                 330                 335

Leu Asn Asp Ala Val Lys Met Ile Asn Phe Ile Lys Ser Arg Pro Leu
                    340                 345                 350

Asn Ala Arg Val Phe Ala Leu Leu Cys Asp Asp Leu Gly Ser Leu His
                355                 360                 365

Lys Asn Leu Leu Leu His Thr Glu Val Arg Trp Leu Ser Arg Gly Lys
            370                 375                 380

Val Leu Thr Arg Phe Trp Glu Leu Arg Asp Glu Ile Arg Ile Phe Phe
        385                 390                 395                 400

Asn Glu Arg Glu Phe Ala Gly Lys Leu Asn Asp Thr Ser Trp Leu Gln
                        405                 410                 415

Asn Leu Ala Tyr Ile Ala Asp Ile Phe Ser Tyr Leu Asn Glu Val Asn
                    420                 425                 430

Leu Ser Leu Gln Gly Pro Asn Ser Thr Ile Phe Lys Val Asn Ser Arg
                435                 440                 445

Ile Asn Ser Ile Lys Ser Lys Leu Lys Leu Trp Glu Glu Cys Ile Thr
            450                 455                 460

Lys Asn Asn Thr Glu Cys Phe Ala Asn Leu Asn Asp Phe Leu Glu Thr
        465                 470                 475                 480

Ser Asn Thr Ala Leu Asp Pro Asn Leu Lys Ser Asn Ile Leu Glu His
                        485                 490                 495

Leu Asn Gly Leu Lys Asn Thr Phe Leu Glu Tyr Phe Pro Pro Thr Cys
                    500                 505                 510

Asn Asn Ile Ser Trp Val Glu Asn Pro Phe Asn Glu Cys Gly Asn Val
                515                 520                 525

Asp Thr Leu Pro Ile Lys Glu Arg Glu Gln Leu Ile Asp Ile Arg Thr
            530                 535                 540

Asp Thr Thr Leu Lys Ser Ser Phe Val Pro Asp Gly Ile Gly Pro Phe
        545                 550                 555                 560

Trp Ile Lys Leu Met Asp Glu Phe Pro Glu Ile Ser Lys Arg Ala Val
                        565                 570                 575

Lys Glu Leu Met Pro Phe Val Thr Thr Tyr Leu Cys Glu Lys Ser Phe
                    580                 585                 590

Ser Val Tyr Val Ala Thr Lys Thr Lys Tyr Arg Asn Arg Leu Asp Ala
                595                 600                 605

Glu Asp Asp Met Arg Leu Gln Leu Thr Thr Ile His Pro Asp Ile Asp
            610                 615                 620

Asn Leu Cys Asn Asn Lys Gln Ala Gln Lys Ser His
        625                 630                 635

<210> SEQ ID NO 152
<211> LENGTH: 211
<212> TYPE: DNA
<213> ORGANISM: Artificial sequence
<220> FEATURE:
<223> OTHER INFORMATION: Synthetic

<400> SEQUENCE: 152
tccctatcag tgatagagag tctagtctgc ataccttccc tatcagtgat agagagacaa       60
```

```
ctccttatag gttccctatc agtgatagag agtaaactgg tcataccttc cctatcagtg      120
atagagagta aactgtagat accttcccta tcagtgatag agtaaaact ggatataggt      180 tccctatcag tgatagagaa agcttatacc t                                    211
```

<210> SEQ ID NO 153
<211> LENGTH: 103
<212> TYPE: DNA
<213> ORGANISM: Artificial sequence
<220> FEATURE:
<223> OTHER INFORMATION: Synthetic

<400> SEQUENCE: 153

```
tccctatcag tgatagagag taaactgtag ataccttccc tatcagtgat agagagtaaa      60
ctggatatag gttccctatc agtgatagag aaagcttata cct                       103
```

<210> SEQ ID NO 154
<211> LENGTH: 467
<212> TYPE: PRT
<213> ORGANISM: Artificial sequence
<220> FEATURE:
<223> OTHER INFORMATION: Synthetic

<400> SEQUENCE: 154

```
Met Gly Val Lys Val Leu Phe Ala Leu Ile Cys Ile Ala Val Ala Glu
1               5                   10                  15

Ala Glu Val Gln Leu Val Glu Ser Gly Gly Leu Val Gln Pro Gly
            20                  25                  30

Gly Ser Leu Arg Leu Ser Cys Ala Ala Ser Gly Phe Asn Ile Lys Asp
        35                  40                  45

Thr Tyr Ile His Trp Val Arg Gln Ala Pro Gly Lys Gly Leu Glu Trp
    50                  55                  60

Val Ala Arg Ile Tyr Pro Thr Asn Gly Tyr Thr Arg Tyr Ala Asp Ser
65                  70                  75                  80

Val Lys Gly Arg Phe Thr Ile Ser Ala Asp Thr Ser Lys Asn Thr Ala
                85                  90                  95

Tyr Leu Gln Met Asn Ser Leu Arg Ala Glu Asp Thr Ala Val Tyr Tyr
            100                 105                 110

Cys Ser Arg Trp Gly Gly Asp Gly Phe Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255
```

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 155
<211> LENGTH: 236
<212> TYPE: PRT
<213> ORGANISM: Artificial sequence
<220> FEATURE:
<223> OTHER INFORMATION: Synthetic

<400> SEQUENCE: 155

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

```
<210> SEQ ID NO 156
<211> LENGTH: 26
<212> TYPE: DNA
<213> ORGANISM: Artificial sequence
<220> FEATURE:
<223> OTHER INFORMATION: Synthetic

<400> SEQUENCE: 156
agaaacaaac caacctgtct gtatta                                          26

<210> SEQ ID NO 157
<211> LENGTH: 28
<212> TYPE: DNA
<213> ORGANISM: Artificial sequence
<220> FEATURE:
<223> OTHER INFORMATION: Synthetic

<400> SEQUENCE: 157
aacaaacaga caatctggtc tgtttgta                                        28

<210> SEQ ID NO 158
<211> LENGTH: 43
<212> TYPE: DNA
<213> ORGANISM: Artificial sequence
<220> FEATURE:
<223> OTHER INFORMATION: Synthetic

<400> SEQUENCE: 158
ttgaaaacaa acagacaatc tggtctgttt gtattataag taa                       43

<210> SEQ ID NO 159
<211> LENGTH: 30
<212> TYPE: DNA
<213> ORGANISM: Artificial sequence
<220> FEATURE:
<223> OTHER INFORMATION: Synthetic

<400> SEQUENCE: 159
aaagaaacaa accaacctgt ctgtattatc                                      30

<210> SEQ ID NO 160
<211> LENGTH: 28
<212> TYPE: DNA
<213> ORGANISM: Artificial sequence
<220> FEATURE:
<223> OTHER INFORMATION: Synthetic

<400> SEQUENCE: 160
aagaaacaaa ccaacctgtc tgtattat                                        28
```

```
<210> SEQ ID NO 161
<211> LENGTH: 301
<212> TYPE: DNA
<213> ORGANISM: Artificial sequence
<220> FEATURE:
<223> OTHER INFORMATION: Synthetic

<400> SEQUENCE: 161
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctcagaaa caaaccaacc tgtctgtatt   300
a                                                                   301

<210> SEQ ID NO 162
<211> LENGTH: 303
<212> TYPE: DNA
<213> ORGANISM: Artificial sequence
<220> FEATURE:
<223> OTHER INFORMATION: Synthetic

<400> SEQUENCE: 162
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctcaacaa acagacaatc tggtctgttt   300
gta                                                                 303

<210> SEQ ID NO 163
<211> LENGTH: 303
<212> TYPE: DNA
<213> ORGANISM: Artificial sequence
<220> FEATURE:
<223> OTHER INFORMATION: Synthetic

<400> SEQUENCE: 163
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctcaacaa acagacaatc tggtctgttt   300
gta                                                                 303

<210> SEQ ID NO 164
<211> LENGTH: 231
<212> TYPE: DNA
<213> ORGANISM: Artificial sequence
<220> FEATURE:
<223> OTHER INFORMATION: Synthetic

<400> SEQUENCE: 164
aaagaaacaa accaacctgt ctgtattatc aaagaaacaa accaacctgt ctgtattatc    60
aaagaaacaa accaacctgt ctgtattatc aaagaaacaa accaacctgt ctgtattatc   120
```

```
aaagaaacaa accaacctgt ctgtattatc aaagaaacaa accaacctgt ctgtattatc      180
taggcgtgcc ctatgggcgg tctatataag cagagcccgt ttagtgaacc g               231

<210> SEQ ID NO 165
<211> LENGTH: 231
<212> TYPE: DNA
<213> ORGANISM: Artificial sequence
<220> FEATURE:
<223> OTHER INFORMATION: Synthetic

<400> SEQUENCE: 165
aaacaaacag acaatctggt ctgtttgtat aaacaaacag acaatctggt ctgtttgtat      60
aaacaaacag acaatctggt ctgtttgtat aaacaaacag acaatctggt ctgtttgtat      120
aaacaaacag acaatctggt ctgtttgtat aaacaaacag acaatctggt ctgtttgtat      180
taggcgtgcc ctatgggcgg tctatataag cagagcccgt ttagtgaacc g               231

<210> SEQ ID NO 166
<211> LENGTH: 309
<212> TYPE: DNA
<213> ORGANISM: Artificial sequence
<220> FEATURE:
<223> OTHER INFORMATION: Synthetic

<400> SEQUENCE: 166
ttgaaaacaa acagacaatc tggtctgttt gtattataag taattgaaaa caaacagaca      60
atctggtctg tttgtattat aagtaattga aacaaacag acaatctggt ctgtttgtat       120
tataagtaat tgaaaacaaa cagacaatct ggtctgtttg tattataagt aattgaaaac      180
aaacagacaa tctggtctgt ttgtattata agtaattgaa aacaaacaga caatctggtc      240
tgtttgtatt ataagtaata ggcgtgccct atgggcggtc tatataagca gagcccgttt      300
agtgaaccg                                                              309

<210> SEQ ID NO 167
<211> LENGTH: 331
<212> TYPE: DNA
<213> ORGANISM: Artificial sequence
<220> FEATURE:
<223> OTHER INFORMATION: Synthetic

<400> SEQUENCE: 167
aaagaaacaa accaacctgt ctgtattatc aaagaaacaa accaacctgt ctgtattatc      60
aaagaaacaa accaacctgt ctgtattatc aaagaaacaa accaacctgt ctgtattatc      120
aaagaaacaa accaacctgt ctgtattatc aaagaaacaa accaacctgt ctgtattatc      180
taggcgtgcc ctatgggcgg tctatataag cagagcccgt ttagtgaacc gtcagatcgc      240
ctggagaggc catccaacgt ctctggggtg agacagcttg cttgttcttt ttgcagaagc      300
tcagaataaa cgctcaactt tggccgccac c                                     331

<210> SEQ ID NO 168
<211> LENGTH: 331
<212> TYPE: DNA
<213> ORGANISM: Artificial sequence
<220> FEATURE:
<223> OTHER INFORMATION: Synthetic

<400> SEQUENCE: 168
aaacaaacag acaatctggt ctgtttgtat aaacaaacag acaatctggt ctgtttgtat      60
aaacaaacag acaatctggt ctgtttgtat aaacaaacag acaatctggt ctgtttgtat      120
```

-continued

```
aaacaaacag acaatctggt ctgtttgtat aaacaaacag acaatctggt ctgtttgtat      180
taggcgtgcc ctatgggcgg tctatataag cagagcccgt ttagtgaacc gtcagatcgc      240
ctggagaggc catccaacgt ctctggggtg agacagcttg cttgttcttt ttgcagaagc      300
tcagaataaa cgctcaactt tggccgccac c                                    331
```

<210> SEQ ID NO 169
<211> LENGTH: 409
<212> TYPE: DNA
<213> ORGANISM: Artificial sequence
<220> FEATURE:
<223> OTHER INFORMATION: Synthetic

<400> SEQUENCE: 169

```
ttgaaaacaa acagacaatc tggtctgttt gtattataag taattgaaaa caaacagaca       60
atctggtctg tttgtattat aagtaattga aaacaaacag acaatctggt ctgtttgtat      120
tataagtaat tgaaaacaaa cagacaatct ggtctgtttg tattataagt aattgaaaac      180
aaacagacaa tctggtctgt tgtattata agtaattgaa acaaacaga caatctggtc       240 tgtttgtatt ataagtaata ggcgtgccct atgggcggtc tatataagca gagcccgttt      300
agtgaaccgt cagatcgcct ggagaggcca tccaacgtct ctggggtgag acagcttgct      360
tgttcttttt gcagaagctc agaataaacg ctcaactttg ccgccacc                   409
```

<210> SEQ ID NO 170
<211> LENGTH: 206
<212> TYPE: PRT
<213> ORGANISM: Artificial sequence
<220> FEATURE:
<223> OTHER INFORMATION: Synthetic

<400> SEQUENCE: 170

```
Met Val Ile Met Ser Pro Lys Arg Arg Thr Gln Ala Glu Arg Ala Met
1               5                   10                  15

Glu Thr Gln Gly Lys Leu Ile Ala Ala Ala Leu Gly Val Leu Arg Glu
                20                  25                  30

Lys Gly Tyr Ala Gly Phe Arg Ile Ala Asp Val Pro Gly Ala Ala Gly
            35                  40                  45

Val Ser Arg Gly Ala Gln Ser His His Phe Pro Thr Lys Leu Glu Leu
        50                  55                  60

Leu Leu Ala Thr Phe Glu Trp Leu Tyr Glu Gln Ile Thr Glu Arg Ser
65                  70                  75                  80

Arg Ala Arg Leu Ala Lys Leu Lys Pro Glu Asp Val Ile Gln Gln
                85                  90                  95

Met Leu Asp Asp Ala Ala Glu Phe Phe Leu Asp Asp Phe Ser Ile
                100                 105                 110

Ser Leu Asp Leu Ile Val Ala Ala Asp Arg Asp Pro Ala Leu Arg Glu
        115                 120                 125

Gly Ile Gln Arg Thr Val Glu Arg Asn Arg Phe Val Val Glu Asp Met
    130                 135                 140

Trp Leu Gly Val Leu Val Ser Arg Gly Leu Ser Arg Asp Asp Ala Glu
145                 150                 155                 160

Asp Ile Leu Trp Leu Ile Phe Asn Ser Val Arg Gly Leu Ala Val Arg
                165                 170                 175

Ser Leu Trp Gln Lys Asp Lys Glu Arg Phe Glu Arg Val Arg Asn Ser
            180                 185                 190
```

Thr Leu Glu Ile Ala Arg Glu Arg Tyr Ala Lys Phe Lys Arg
          195                 200                 205

<210> SEQ ID NO 171
<211> LENGTH: 206
<212> TYPE: PRT
<213> ORGANISM: Artificial sequence
<220> FEATURE:
<223> OTHER INFORMATION: Synthetic

<400> SEQUENCE: 171

Met Val Ile Met Ser Pro Lys Arg Arg Thr Gln Ala Glu Arg Ala Met
1               5                   10                  15

Glu Thr Gln Gly Lys Leu Ile Ala Ala Leu Gly Val Leu Arg Glu
            20                  25                  30

Lys Gly Tyr Ala Gly Phe Arg Ile Ala Asp Val Pro Gly Ala Ala Gly
            35                  40                  45

Val Ser Arg Gly Ala Gln Ser His His Phe Pro Thr Lys Leu Glu Leu
        50                  55                  60

Leu Leu Ala Thr Phe Glu Trp Leu Tyr Glu Gln Ile Thr Glu Arg Ser
65                  70                  75                  80

Arg Ala Arg Leu Ala Lys Leu Lys Pro Glu Asp Asp Val Ile Gln Gln
                85                  90                  95

Met Leu Asp Asp Ala Ala Glu Phe Phe Leu Asp Asp Phe Ser Ile
            100                 105                 110

Ser Leu Asp Leu Ile Val Ala Ala Asp Arg Asp Pro Val Leu Arg Glu
        115                 120                 125

Gly Ile Gln Arg Thr Val Glu Arg Asn Arg Phe Val Val Gly Asp Ile
    130                 135                 140

Trp Leu Gly Val Leu Val Ser Arg Gly Leu Ser Arg Asp Asp Ala Glu
145                 150                 155                 160

Asp Ile Leu Trp Leu Ile Phe Asn Ser Val Arg Gly Leu Ala Val Arg
                165                 170                 175

Ser Leu Trp Gln Lys Asp Lys Glu Arg Phe Glu Arg Val Arg Asn Ser
            180                 185                 190

Thr Leu Glu Ile Ala Arg Glu Arg Tyr Ala Lys Phe Lys Arg
          195                 200                 205

<210> SEQ ID NO 172
<211> LENGTH: 272
<212> TYPE: PRT
<213> ORGANISM: Artificial sequence
<220> FEATURE:
<223> OTHER INFORMATION: Synthetic

<400> SEQUENCE: 172

Met Val Ile Met Ser Pro Lys Arg Arg Thr Gln Ala Glu Arg Ala Met
1               5                   10                  15

Glu Thr Gln Gly Lys Leu Ile Ala Ala Leu Gly Val Leu Arg Glu
            20                  25                  30

Lys Gly Tyr Ala Gly Phe Arg Ile Ala Asp Val Pro Gly Ala Ala Gly
            35                  40                  45

Val Ser Arg Gly Ala Gln Ser His His Phe Pro Thr Lys Leu Glu Leu
        50                  55                  60

Leu Leu Ala Thr Phe Glu Trp Leu Tyr Glu Gln Ile Thr Glu Arg Ser
65                  70                  75                  80

Arg Ala Arg Leu Ala Lys Leu Lys Pro Glu Asp Asp Val Ile Gln Gln
                85                  90                  95

-continued

```
Met Leu Asp Asp Ala Ala Glu Phe Phe Leu Asp Asp Phe Ser Ile
            100                 105                 110

Ser Leu Asp Leu Ile Val Ala Ala Asp Arg Asp Pro Val Leu Arg Glu
            115                 120                 125

Gly Ile Gln Arg Thr Val Glu Arg Asn Arg Phe Val Val Gly Asp Ile
            130                 135                 140

Trp Leu Gly Val Leu Val Ser Arg Gly Leu Ser Arg Asp Asp Ala Glu
145                 150                 155                 160

Asp Ile Leu Trp Leu Ile Phe Asn Ser Val Arg Gly Leu Ala Val Arg
                165                 170                 175

Ser Leu Trp Gln Lys Asp Lys Glu Arg Phe Glu Arg Val Arg Asn Ser
            180                 185                 190

Thr Leu Glu Ile Ala Arg Glu Arg Tyr Ala Lys Phe Lys Arg Ala Tyr
            195                 200                 205

Ser Arg Ala Arg Thr Lys Asn Asn Tyr Gly Ser Thr Ile Glu Gly Leu
            210                 215                 220

Leu Asp Leu Pro Asp Asp Asp Pro Thr Asp Ala Leu Asp Asp Phe Asp
225                 230                 235                 240

Leu Asp Met Leu Pro Ala Asp Ala Leu Asp Asp Phe Asp Leu Asp Met
                245                 250                 255

Leu Pro Ala Asp Ala Leu Asp Asp Phe Asp Leu Asp Met Leu Pro Gly
                260                 265                 270
```